US011312760B1

(12) United States Patent
Li et al.

(10) Patent No.: US 11,312,760 B1
(45) Date of Patent: Apr. 26, 2022

(54) EXPRESSION VECTOR FOR ANTI-SARS-COV-2 NEUTRALIZING ANTIBODIES

(71) Applicant: NEWSOARA BIOPHARMA CO., LTD., Shanghai (CN)

(72) Inventors: Yuannian Li, Shanghai (CN); Wenyi Wang, Shanghai (CN)

(73) Assignee: NEWSOARA BIOPHARMA CO., LTD., Shanghai (CN)

( * ) Notice: Subject to any disclaimer, the term of this patent is extended or adjusted under 35 U.S.C. 154(b) by 0 days.

(21) Appl. No.: 17/391,262

(22) Filed: Aug. 2, 2021

(30) Foreign Application Priority Data

Jan. 19, 2021 (CN) ................. PCT/CN2021/072629

(51) Int. Cl.

| | |
|---|---|
| ***C07K 16/10*** | (2006.01) |
| ***A61P 31/14*** | (2006.01) |
| ***C12N 15/86*** | (2006.01) |
| ***A61K 39/42*** | (2006.01) |

(52) U.S. Cl.

CPC .............. *C07K 16/10* (2013.01); *A61K 39/42* (2013.01); *A61P 31/14* (2018.01); *C12N 15/86* (2013.01); *C07K 2317/56* (2013.01)

(58) Field of Classification Search

CPC ......... C07K 16/10; A61K 39/42; A61P 31/14; C12N 15/86

USPC .............. 424/199.1, 139.1, 147.1; 514/44 R; 530/388.3; 435/320.1, 331, 339

See application file for complete search history.

(56) References Cited

U.S. PATENT DOCUMENTS

2019/0216949 A1 7/2019 Wootton et al.

FOREIGN PATENT DOCUMENTS

| | | | |
|---|---|---|---|
| CN | 111303280 | A | 6/2020 |
| CN | 111423508 | A | 7/2020 |
| CN | 111592594 | A | 8/2020 |
| CN | 111592595 | A | 8/2020 |
| CN | 111690058 | A | 9/2020 |
| CN | 111825762 | A | 10/2020 |
| CN | 111995674 | A | 11/2020 |
| CN | 112010963 | A | 12/2020 |
| CN | 112094340 | A | 12/2020 |
| CN | 112175073 | A | 1/2021 |
| CN | 112225797 | A | 1/2021 |
| CN | 112225806 | A | 1/2021 |
| CN | 112300274 | A | 2/2021 |
| CN | 112442120 | A | 3/2021 |
| CN | 112552399 | A | 3/2021 |
| WO | 2005060520 | A2 | 7/2005 |

OTHER PUBLICATIONS

Vajdos et al. (2002) J. Mol. Biol., vol. 320, 415-428.*

Chen et al. (1992) J. Exp. Med., vol. 176, 855-866.*

Sela-Culang et al. (2013) Frontiers in Immunology, vol. 4, pp. 1-13.*

Wang et al., "A human monoclonal antibody blocking SARS-CoV-2 infection," Nature Communications vol. 11, Article No. 2251, May 4, 2020.

The Australian Examination Report, dated Sep. 10, 2021, in the related Australian Appl. No. 2021209287.

Ju et al., "Potent human neutralizing antibodies elicited by SARS-CoV-2 infection," BioRxiv preprint, posted online Mar. 26, 2020.

Liu et al., "Potent Neutralizing Monoclonal Antibodies Directed to Multiple Epitopes on the SARS-CoV-2 Spike," BioRxiv preprint, posted online Jun. 18, 2020, URL: https://doi.org/101101/2020.06.17.153486.

Rogers et al., "Rapid isolation of potent SARS-CoV-2 neutralizing antibodies and protection in a small animal model," BioRxiv preprint, posted online May 15, 2020, URL: https://doi.org/10.1101/2020.05.11.088674.

Zhang et al., "Protein and Enzyme Engineering," Hefei University of Technology Press, 1st edition, Chapter 10, pp. 201-206, Sep. 2015. The English concise explanation of the relevance included.

* cited by examiner

*Primary Examiner* — Anne Marie S Wehbe

(57) ABSTRACT

The present disclosure provides recombinant expression vectors expressing a novel neutralizing antibodies against SARS-COV-2, or the antigen binding fragments thereof. Pharmaceutical composition and kits comprising the same, and the uses thereof are also provided.

18 Claims, 4 Drawing Sheets

Specification includes a Sequence Listing.

SEQUENCE LISTING

```
<160> NUMBER OF SEQ ID NOS: 63

<210> SEQ ID NO 1
<211> LENGTH: 5
<212> TYPE: PRT
<213> ORGANISM: Homo sapiens
<220> FEATURE:
<221> NAME/KEY: 15A7 HCDR1
<222> LOCATION: (1)..(5)

<400> SEQUENCE: 1

Ser Tyr Asp Ile Asn
1               5


<210> SEQ ID NO 2
<211> LENGTH: 17
<212> TYPE: PRT
<213> ORGANISM: Homo sapiens
<220> FEATURE:
<221> NAME/KEY: 15A7 HCDR2
<222> LOCATION: (1)..(17)

<400> SEQUENCE: 2

Trp Met Asn Pro Asn Ser Ala Asn Pro Gly Tyr Ala Gln Lys Phe Gln
1               5                   10                  15

Gly


<210> SEQ ID NO 3
<211> LENGTH: 20
<212> TYPE: PRT
<213> ORGANISM: Homo sapiens
<220> FEATURE:
<221> NAME/KEY: 15A7 HCDR3
<222> LOCATION: (1)..(20)

<400> SEQUENCE: 3

Ala Arg Val Thr Ile His Tyr Asp Ile Leu Thr Gly Tyr Tyr Ser Asn
1               5                   10                  15

Ala Phe Asp Ile
            20


<210> SEQ ID NO 4
<211> LENGTH: 11
<212> TYPE: PRT
<213> ORGANISM: Homo sapiens
<220> FEATURE:
<221> NAME/KEY: 15A7 LCDR1
<222> LOCATION: (1)..(11)

<400> SEQUENCE: 4

Arg Ala Ser Gln Thr Ile Ser Ser Tyr Leu Asn
1               5                   10


<210> SEQ ID NO 5
<211> LENGTH: 7
<212> TYPE: PRT
<213> ORGANISM: Homo sapiens
<220> FEATURE:
<221> NAME/KEY: 15A7 LCDR2
<222> LOCATION: (1)..(7)

<400> SEQUENCE: 5

Ala Ala Ser Ser Leu Gln Ser
1               5


<210> SEQ ID NO 6
```

```
<211> LENGTH: 10
<212> TYPE: PRT
<213> ORGANISM: Homo sapiens
<220> FEATURE:
<221> NAME/KEY: 15A7 LCDR3
<222> LOCATION: (1)..(10)

<400> SEQUENCE: 6

Gln Gln Ser Tyr Thr Thr Phe Met Tyr Thr
1               5                   10


<210> SEQ ID NO 7
<211> LENGTH: 129
<212> TYPE: PRT
<213> ORGANISM: Homo sapiens
<220> FEATURE:
<221> NAME/KEY: 15A7 VH
<222> LOCATION: (1)..(129)

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Ser Gly Gln Gly Leu Glu Trp Met
        35                  40                  45

Gly Trp Met Asn Pro Asn Ser Ala Asn Pro Gly Tyr Ala Gln Lys Phe
    50                  55                  60

Gln Gly Arg Val Thr Met Thr Arg Asn Thr Ser Ile Ser Thr Ala Phe
65                  70                  75                  80

Met Glu Leu Ser Ser Leu Arg Ser Asp Asp Thr Ala Val Tyr Tyr Cys
                85                  90                  95

Ala Arg Ala Arg Val Thr Ile His Tyr Asp Ile Leu Thr Gly Tyr Tyr
            100                 105                 110

Ser Asn Ala Phe Asp Ile Trp Gly Gln Gly Thr Met Val Ala Val Ser
        115                 120                 125

Ser


<210> SEQ ID NO 8
<211> LENGTH: 108
<212> TYPE: PRT
<213> ORGANISM: Homo sapiens
<220> FEATURE:
<221> NAME/KEY: 15A7 VL
<222> LOCATION: (1)..(108)

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Phe Met
                85                  90                  95

Tyr Thr Phe Gly Gln Gly Thr Met Leu Glu Ile Lys
```

100 105

<210> SEQ ID NO 9
<211> LENGTH: 387
<212> TYPE: DNA
<213> ORGANISM: Homo sapiens
<220> FEATURE:
<221> NAME/KEY: 15A7 VH
<222> LOCATION: (1)..(387)

<400> SEQUENCE: 9

```
caggtgcagc tggtgcagtc tggggctgag gtgaagaagc ctggggcctc agtgaaggtc     60

tcctgcaagg cttctggata caccttcacc agttatgata tcaactgggt gcgacaggcc    120

tctggacaag ggcttgagtg gatgggatgg atgaacccta acagtgctaa cccaggctat    180

gcacagaagt tccagggcag agtcaccatg accaggaaca cctccataag cacagccttc    240

atggagctga gcagcctgag atctgacgac acggccgtgt attactgtgc gagagcccga    300

gtaactatac attacgatat tttgactggt tattattcga atgcttttga tatctggggc    360

caagggacaa tggtcgccgt ctcttca                                        387
```

<210> SEQ ID NO 10
<211> LENGTH: 324
<212> TYPE: DNA
<213> ORGANISM: Homo sapiens
<220> FEATURE:
<221> NAME/KEY: 15A7 VL
<222> LOCATION: (1)..(324)

<400> SEQUENCE: 10

```
gacatccaga tgacccagtc tccatcctcc ctgtctgcat ctgtaggaga cagagtcacc     60

atcacttgcc gggcaagtca gaccattagc agctatttaa attggtatca gcagaaacca    120

gggaaagccc ctaagctcct gatctatgct gcatccagtt tgcaaagtgg ggtcccatca    180

aggttcagtg gcagtggatc tggggcagat ttcactctca ccatcagcag tctgcaacct    240

gaagattttg caacttacta ctgtcaacag agttacacta ccttcatgta cacttttggc    300

caggggacca tgctggagat caaa                                           324
```

<210> SEQ ID NO 11
<211> LENGTH: 5
<212> TYPE: PRT
<213> ORGANISM: Homo sapiens
<220> FEATURE:
<221> NAME/KEY: 31C2 HCDR1
<222> LOCATION: (1)..(5)

<400> SEQUENCE: 11

```
Ser Tyr Ala Ile Ser
1               5
```

<210> SEQ ID NO 12
<211> LENGTH: 17
<212> TYPE: PRT
<213> ORGANISM: Homo sapiens
<220> FEATURE:
<221> NAME/KEY: 31C2 HCDR2
<222> LOCATION: (1)..(17)

<400> SEQUENCE: 12

```
Gly Ile Ile Pro Ile Phe Gly Thr Thr Asn Tyr Ala Gln Lys Phe Gln
1               5                   10                  15

Gly
```

<210> SEQ ID NO 13
<211> LENGTH: 13
<212> TYPE: PRT
<213> ORGANISM: Homo sapiens
<220> FEATURE:
<221> NAME/KEY: 31C2 HCDR3
<222> LOCATION: (1)..(13)

<400> SEQUENCE: 13

Arg Ser Ala Tyr Gly Asp Lys Gly Tyr Tyr Phe Asp Tyr
1 5 10

<210> SEQ ID NO 14
<211> LENGTH: 11
<212> TYPE: PRT
<213> ORGANISM: Homo sapiens
<220> FEATURE:
<221> NAME/KEY: 31C2 LCDR1
<222> LOCATION: (1)..(11)

<400> SEQUENCE: 14

Arg Ala Ser Gln Ser Val Ser Asn Phe Leu Ala
1 5 10

<210> SEQ ID NO 15
<211> LENGTH: 7
<212> TYPE: PRT
<213> ORGANISM: Homo sapiens
<220> FEATURE:
<221> NAME/KEY: 31C2 LCDR2
<222> LOCATION: (1)..(7)

<400> SEQUENCE: 15

Asp Ala Ser Asn Arg Ala Thr
1 5

<210> SEQ ID NO 16
<211> LENGTH: 11
<212> TYPE: PRT
<213> ORGANISM: Homo sapiens
<220> FEATURE:
<221> NAME/KEY: 31C2 LCDR3
<222> LOCATION: (1)..(11)

<400> SEQUENCE: 16

Gln Gln Arg Ser Asn Trp Pro Pro Gln Glu Thr
1 5 10

<210> SEQ ID NO 17
<211> LENGTH: 122
<212> TYPE: PRT
<213> ORGANISM: Homo sapiens
<220> FEATURE:
<221> NAME/KEY: 31C2 VH
<222> LOCATION: (1)..(122)

<400> SEQUENCE: 17

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Thr Asn Tyr Ala Gln Lys Phe
50 55 60

```
Gln Gly Arg Val Thr Ile Thr Ala Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Gly Arg Ser Ala Tyr Gly Asp Lys Gly Tyr Tyr Phe Asp Tyr Trp
            100                 105                 110

Gly Gln Gly Thr Leu Val Thr Val Ser Ser
        115                 120


<210> SEQ ID NO 18
<211> LENGTH: 109
<212> TYPE: PRT
<213> ORGANISM: Homo sapiens
<220> FEATURE:
<221> NAME/KEY: 31C2 VL
<222> LOCATION: (1)..(109)

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ser Asn Trp Pro Pro
                85                  90                  95

Gln Glu Thr Phe Gly Gln Gly Thr Lys Val Glu Ile Lys
            100                 105


<210> SEQ ID NO 19
<211> LENGTH: 366
<212> TYPE: DNA
<213> ORGANISM: Homo sapiens
<220> FEATURE:
<221> NAME/KEY: 31C2 VH
<222> LOCATION: (1)..(366)

<400> SEQUENCE: 19

caggtgcagc tggtgcagtc tggggctgag gtgaagaagc ctgggtcgtc ggtgaaggtc      60

tcctgcaagg cttctggagg caccttcagc agctatgcta tcagctgggt gcgacaggcc     120

cctggacaag ggcttgagtg gatgggaggg atcatcccta tctttggtac aacaaactac     180

gcacagaagt tccagggcag agtcacgatt accgcggacg aatccacgag cacagcctac     240

atggagctga acagcctgag atctgaggac acggccgtgt attactgtgc gggacgttcg     300

gcctacggtg ataaagggta ctactttgat tactggggcc agggaaccct ggtcaccgtc     360

tcctca                                                                366


<210> SEQ ID NO 20
<211> LENGTH: 327
<212> TYPE: DNA
<213> ORGANISM: Homo sapiens
<220> FEATURE:
<221> NAME/KEY: 31C2 VL
<222> LOCATION: (1)..(327)
```

```
<400> SEQUENCE: 20

gaaattgtgt tgacacagtc tccagccacc ctgtctttgt ctccagggga aagagccacc     60

ctctcctgca gggccagtca gagtgttagc aacttcttag cctggtatca acagaaacct    120

ggccaggctc ccaggctcct catctatgat gcatccaaca gggccactgg catcccagcc    180

aggttcagtg gcagtgggtc tgggacagac ttcactctca ccatcagcag cctacagcct    240

gaagattttg cagtttatta ctgtcagcag cgtagcaact ggcctccgca agagacgttc    300

ggccaaggga ccaaggtgga aatcaaa                                        327


<210> SEQ ID NO 21
<211> LENGTH: 5
<212> TYPE: PRT
<213> ORGANISM: Homo sapiens
<220> FEATURE:
<221> NAME/KEY: 37G2 HCDR1
<222> LOCATION: (1)..(5)

<400> SEQUENCE: 21

Ser Tyr Ala Ile Thr
1               5


<210> SEQ ID NO 22
<211> LENGTH: 17
<212> TYPE: PRT
<213> ORGANISM: Homo sapiens
<220> FEATURE:
<221> NAME/KEY: 37G2 HCDR2
<222> LOCATION: (1)..(17)

<400> SEQUENCE: 22

Gly Ile Ile Pro Ile Phe Gly Thr Ala Asn Phe Ala Gln Lys Phe Gln
1               5                   10                  15

Gly


<210> SEQ ID NO 23
<211> LENGTH: 10
<212> TYPE: PRT
<213> ORGANISM: Homo sapiens
<220> FEATURE:
<221> NAME/KEY: 37G2 HCDR3
<222> LOCATION: (1)..(10)

<400> SEQUENCE: 23

Leu Gly Gly Phe Ala Asp Pro Phe Asp Tyr
1               5                   10


<210> SEQ ID NO 24
<211> LENGTH: 11
<212> TYPE: PRT
<213> ORGANISM: Homo sapiens
<220> FEATURE:
<221> NAME/KEY: 37G2 LCDR1
<222> LOCATION: (1)..(11)

<400> SEQUENCE: 24

Arg Ala Ser Gln Ser Val Ser Asn Tyr Leu Ala
1               5                   10


<210> SEQ ID NO 25
<211> LENGTH: 7
<212> TYPE: PRT
<213> ORGANISM: Homo sapiens
<220> FEATURE:
<221> NAME/KEY: 37G2 LCDR2
```

<222> LOCATION: (1)..(7)

<400> SEQUENCE: 25

Asp Ala Phe Asn Arg Ala Thr
1               5

<210> SEQ ID NO 26
<211> LENGTH: 11
<212> TYPE: PRT
<213> ORGANISM: Homo sapiens
<220> FEATURE:
<221> NAME/KEY: 37G2 LCDR3
<222> LOCATION: (1)..(11)

<400> SEQUENCE: 26

Gln Gln Arg Ser Asn Trp Pro Pro Arg Ile Thr
1               5                   10

<210> SEQ ID NO 27
<211> LENGTH: 119
<212> TYPE: PRT
<213> ORGANISM: Homo sapiens
<220> FEATURE:
<221> NAME/KEY: 37G2 VH
<222> LOCATION: (1)..(119)

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Pro Ile Phe Gly Thr Ala Asn Phe Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala His Leu Gly Gly Phe Ala Asp Pro Phe Asp Tyr Trp Gly Gln Gly
            100                 105                 110

Thr Leu Val Thr Val Ser Ser
        115

<210> SEQ ID NO 28
<211> LENGTH: 109
<212> TYPE: PRT
<213> ORGANISM: Homo sapiens
<220> FEATURE:
<221> NAME/KEY: 37G2 VL
<222> LOCATION: (1)..(109)

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Ala Gly Gln Ala Pro Arg Val Leu Ile
        35                  40                  45

Tyr Asp Ala Phe Asn Arg Ala Thr Gly Ile Pro Ala Arg Phe Ser Gly
    50                  55                  60

-continued

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Ile Thr Phe Gly Gln Gly Thr Arg Leu Glu Ile Lys
            100                 105
```

<210> SEQ ID NO 29
<211> LENGTH: 357
<212> TYPE: DNA
<213> ORGANISM: Homo sapiens
<220> FEATURE:
<221> NAME/KEY: 37G2 VH
<222> LOCATION: (1)..(357)

<400> SEQUENCE: 29

```
caggtgcagc tggtgcagtc tggggctgag gtgaagaagc ctgggtcctc ggtgaaggtc     60

tcctgcaagg cttctggagg caccttcagc agctatgcta tcacctgggt gcgacaggcc    120

cctggacaag ggcttgagtg gatgggaggg atcatcccta tctttggtac agcaaacttc    180

gcacagaagt tccagggcag agtcacgatt accgcggacg aatccacgag cacagcctac    240

atggagctga gcagcctgag atctgaggac acggccgtgt attactgtgc ccacctaggg    300

gggttcgctg accccctttga ctactggggc cagggaaccc tggtcaccgt ctcctca      357
```

<210> SEQ ID NO 30
<211> LENGTH: 327
<212> TYPE: DNA
<213> ORGANISM: Homo sapiens
<220> FEATURE:
<221> NAME/KEY: 37G2 VL
<222> LOCATION: (1)..(327)

<400> SEQUENCE: 30

```
gaaattgtgt tgacacagtc tccagccacc ctgtctttgt ctccagggga aagagccacc     60

ctctcctgca gggccagtca gagtgttagc aactacttag cctggtatca acagaaagct    120

ggccaggctc ccagggtcct catctatgat gcattcaaca gggccactgg catcccagcc    180

aggttcagtg gcagtgggtc tgggacagac ttcactctca ccatcagcag cctagagcct    240

gaagattttg cagtttatta ctgtcagcag cgtagcaact ggcctccgcg gatcaccttc    300

ggccaaggga cacgactgga gattaaa                                         327
```

<210> SEQ ID NO 31
<211> LENGTH: 15
<212> TYPE: DNA
<213> ORGANISM: Homo sapiens
<220> FEATURE:
<221> NAME/KEY: 15A7 HCDR1
<222> LOCATION: (1)..(15)

<400> SEQUENCE: 31

```
agttatgata tcaac                                                       15
```

<210> SEQ ID NO 32
<211> LENGTH: 51
<212> TYPE: DNA
<213> ORGANISM: Homo sapiens
<220> FEATURE:
<221> NAME/KEY: 15A7 HCDR2
<222> LOCATION: (1)..(51)

<400> SEQUENCE: 32

```
tggatgaacc ctaacagtgc taacccaggc tatgcacaga agttccaggg c              51


<210> SEQ ID NO 33
<211> LENGTH: 60
<212> TYPE: DNA
<213> ORGANISM: Homo sapiens
<220> FEATURE:
<221> NAME/KEY: 15A7 HCDR3
<222> LOCATION: (1)..(60)

<400> SEQUENCE: 33

gcccgagtaa ctatacatta cgatattttg actggttatt attcgaatgc ttttgatatc     60


<210> SEQ ID NO 34
<211> LENGTH: 33
<212> TYPE: DNA
<213> ORGANISM: Homo sapiens
<220> FEATURE:
<221> NAME/KEY: 15A7 LCDR1
<222> LOCATION: (1)..(33)

<400> SEQUENCE: 34

cgggcaagtc agaccattag cagctattta aat                                  33


<210> SEQ ID NO 35
<211> LENGTH: 21
<212> TYPE: DNA
<213> ORGANISM: Homo sapiens
<220> FEATURE:
<221> NAME/KEY: 15A7 LCDR2
<222> LOCATION: (1)..(21)

<400> SEQUENCE: 35

gctgcatcca gtttgcaaag t                                               21


<210> SEQ ID NO 36
<211> LENGTH: 30
<212> TYPE: DNA
<213> ORGANISM: Homo sapiens
<220> FEATURE:
<221> NAME/KEY: 15A7 LCDR3
<222> LOCATION: (1)..(30)

<400> SEQUENCE: 36

caacagagtt acactacctt catgtacact                                      30


<210> SEQ ID NO 37
<211> LENGTH: 329
<212> TYPE: PRT
<213> ORGANISM: Homo sapiens
<220> FEATURE:
<221> NAME/KEY: human IgG1 constant region
<222> LOCATION: (1)..(329)

<400> SEQUENCE: 37

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80
```

```
Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

```
<210> SEQ ID NO 38
<211> LENGTH: 987
<212> TYPE: DNA
<213> ORGANISM: Homo sapiens
<220> FEATURE:
<221> NAME/KEY: IgG1 Constant Region
<222> LOCATION: (1)..(987)

<400> SEQUENCE: 38

agcaccaagg gcccatcggt cttccccctg gcaccctcct ccaagagcac ctctgggggc     60

acagcggccc tgggctgcct ggtcaaggac tacttccccg aaccggtgac ggtgtcgtgg    120

aactcaggcg ccctgaccag cggcgtgcac accttcccgg ctgtcctaca gtcctcagga    180

ctctactccc tcagcagcgt ggtgaccgtg ccctccagca gcttgggcac ccagacctac    240

atctgcaacg tgaatcacaa gcccagcaac accaaggtgg acaagaaagt tgagcccaaa    300

tcttgtgaca aaactcacac atgcccaccg tgcccagcac ctgaactcct ggggggaccg    360

tcagtcttcc tcttcccccc aaaacccaag gacaccctca tgatctcccg gacccctgag    420

gtcacatgcg tggtggtgga cgtgagccac gaagaccctg aggtcaagtt caactggtac    480

gtggacggcg tggaggtgca taatgccaag acaaagccgc gggaggagca gtacaacagc    540

acgtaccgtg tggtcagcgt cctcaccgtc ctgcaccagg actggctgaa tggcaaggag    600
```

```
tacaagtgca aggtctccaa caaagccctc ccagccccca tcgagaaaac catctccaaa    660

gccaaagggc agccccgaga accacaggtg tacaccctgc ccccatcccg ggaggagatg    720

accaagaacc aggtcagcct gacctgcctg gtcaaaggct tctatcccag cgacatcgcc    780

gtggagtggg agagcaatgg gcagccggag aacaactaca agaccacgcc tcccgtgctg    840

gactccgacg gctccttctt cctctacagc aagctcaccg tggacaagag caggtggcag    900

caggggaacg tcttctcatg ctccgtgatg catgaggctc tgcacaacca ctacacgcag    960

aagagcctct ccctgtctcc gggtaaa                                        987


<210> SEQ ID NO 39
<211> LENGTH: 15
<212> TYPE: DNA
<213> ORGANISM: Homo sapiens
<220> FEATURE:
<221> NAME/KEY: 31C2 HCDR1
<222> LOCATION: (1)..(15)

<400> SEQUENCE: 39

agctatgcta tcagc                                                      15


<210> SEQ ID NO 40
<211> LENGTH: 51
<212> TYPE: DNA
<213> ORGANISM: Homo sapiens
<220> FEATURE:
<221> NAME/KEY: 31C2 HCDR2
<222> LOCATION: (1)..(51)

<400> SEQUENCE: 40

gggatcatcc ctatctttgg tacaacaaac tacgcacaga agttccaggg c              51


<210> SEQ ID NO 41
<211> LENGTH: 39
<212> TYPE: DNA
<213> ORGANISM: Homo sapiens
<220> FEATURE:
<221> NAME/KEY: 31C2 HCDR3
<222> LOCATION: (1)..(39)

<400> SEQUENCE: 41

cgttcggcct acggtgataa agggtactac tttgattac                            39


<210> SEQ ID NO 42
<211> LENGTH: 33
<212> TYPE: DNA
<213> ORGANISM: Homo sapiens
<220> FEATURE:
<221> NAME/KEY: 31C2 LCDR1
<222> LOCATION: (1)..(33)

<400> SEQUENCE: 42

agggccagtc agagtgttag caacttctta gcc                                  33


<210> SEQ ID NO 43
<211> LENGTH: 21
<212> TYPE: DNA
<213> ORGANISM: Homo sapiens
<220> FEATURE:
<221> NAME/KEY: 31C2 LCDR2
<222> LOCATION: (1)..(21)

<400> SEQUENCE: 43

gatgcatcca acagggccac t                                               21
```

<210> SEQ ID NO 44
<211> LENGTH: 33
<212> TYPE: DNA
<213> ORGANISM: Homo sapiens
<220> FEATURE:
<221> NAME/KEY: 31C2 LCDR3
<222> LOCATION: (1)..(33)

<400> SEQUENCE: 44

```
cagcagcgta gcaactggcc tccgcaagag acg                                    33
```

<210> SEQ ID NO 45
<211> LENGTH: 106
<212> TYPE: PRT
<213> ORGANISM: Homo sapiens
<220> FEATURE:
<221> NAME/KEY: human lambda chain constant region
<222> LOCATION: (1)..(106)

<400> SEQUENCE: 45

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 46
<211> LENGTH: 321
<212> TYPE: DNA
<213> ORGANISM: Homo sapiens
<220> FEATURE:
<221> NAME/KEY: Human Lambda Constant Region
<222> LOCATION: (1)..(321)

<400> SEQUENCE: 46

```
ggtcagccca aggctgcccc ctcggtcact ctgttcccgc cctcctctga ggagcttcaa      60

gccaacaagg ccacactggt gtgtctcata agtgacttct acccgggagc cgtgacagtg     120

gcctggaagg cagatagcag ccccgtcaag gcgggagtgg agaccaccac accctccaaa     180

caaagcaaca acaagtacgc ggccagcagc tatctgagcc tgacgcctga gcagtggaag     240

tcccacagaa gctacagctg ccaggtcacg catgaaggga gcaccgtgga gaagacagtg     300

gcccctacag aatgttcata g                                               321
```

<210> SEQ ID NO 47
<211> LENGTH: 15
<212> TYPE: DNA
<213> ORGANISM: Homo sapiens
<220> FEATURE:
<221> NAME/KEY: 37G2 HCDR1
<222> LOCATION: (1)..(15)

<400> SEQUENCE: 47
agctatgcta tcacc 15

<210> SEQ ID NO 48
<211> LENGTH: 51
<212> TYPE: DNA
<213> ORGANISM: Homo sapiens
<220> FEATURE:
<221> NAME/KEY: 37G2 HCDR2
<222> LOCATION: (1)..(51)

<400> SEQUENCE: 48
gggatcatcc ctatctttgg tacagcaaac ttcgcacaga agttccaggg c 51

<210> SEQ ID NO 49
<211> LENGTH: 30
<212> TYPE: DNA
<213> ORGANISM: Homo sapiens
<220> FEATURE:
<221> NAME/KEY: 37G2 HCDR3
<222> LOCATION: (1)..(30)

<400> SEQUENCE: 49 ctagggggt tcgctgaccc ctttgactac 30

<210> SEQ ID NO 50
<211> LENGTH: 33
<212> TYPE: DNA
<213> ORGANISM: Homo sapiens
<220> FEATURE:
<221> NAME/KEY: 37G2 LCDR1
<222> LOCATION: (1)..(33)

<400> SEQUENCE: 50
agggccagtc agagtgttag caactactta gcc 33

<210> SEQ ID NO 51
<211> LENGTH: 21
<212> TYPE: DNA
<213> ORGANISM: Homo sapiens
<220> FEATURE:
<221> NAME/KEY: 37G2 LCDR2
<222> LOCATION: (1)..(21)

<400> SEQUENCE: 51
gatgcattca acagggccac t 21

<210> SEQ ID NO 52
<211> LENGTH: 33
<212> TYPE: DNA
<213> ORGANISM: Homo sapiens
<220> FEATURE:
<221> NAME/KEY: 37G2 LCDR3
<222> LOCATION: (1)..(33)

<400> SEQUENCE: 52
cagcagcgta gcaactggcc tccgcggatc acc 33

<210> SEQ ID NO 53
<211> LENGTH: 130
<212> TYPE: DNA
<213> ORGANISM: Artificial Sequence
<220> FEATURE:
<223> OTHER INFORMATION: Synthetic
<220> FEATURE:
<221> NAME/KEY: ITR1
<222> LOCATION: (1)..(130)

<400> SEQUENCE: 53

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct                                                           130
```

<210> SEQ ID NO 54
<211> LENGTH: 128
<212> TYPE: DNA
<213> ORGANISM: Artificial Sequence
<220> FEATURE:
<223> OTHER INFORMATION: Synthetic
<220> FEATURE:
<221> NAME/KEY: ITR2
<222> LOCATION: (1)..(128)

<400> SEQUENCE: 54

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgc                                                             128
```

<210> SEQ ID NO 55
<211> LENGTH: 1055
<212> TYPE: DNA
<213> ORGANISM: Artificial Sequence
<220> FEATURE:
<223> OTHER INFORMATION: Synthetic
<220> FEATURE:
<221> NAME/KEY: CASI Promoter
<222> LOCATION: (1)..(1055)

<400> SEQUENCE: 55

```
ggagttccgc gttacataac ttacggtaaa tggcccgcct ggctgaccgc ccaacgaccc     60

ccgcccattg acgtcaataa tgacgtatgt tcccatagta acgccaatag ggactttcca    120

ttgacgtcaa tgggtggagt atttacggta aactgcccac ttggcagtac atcaagtgta    180

tcatatgcca agtacgcccc ctattgacgt caatgacggt aaatggcccg cctggcatta    240

tgcccagtac atgaccttat gggactttcc tacttggcag tacatctacg tattagtcat    300

cgctattacc atggtcgagg tgagccccac gttctgcttc actctcccca tctccccccc    360

ctccccaccc ccaattttgt atttatttat tttttaatta ttttgtgcag cgatgggggc    420

gggggggggg gggggcgcgc gccaggcggg gcggggcggg gcgaggggcg gggcggggcg    480

aggcggagag gtgcggcggc agccaatcag agcggcgcgc tccgaaagtt tccttttatg    540

gcgaggcggc ggcggcggcg gccctataaa aagcgaagcg cgcggcgggc gggagtcgct    600

gcgcgctgcc ttcgccccgt gccccgctcc gccgccgcct cgcgccgccc gccccggctc    660

tgactgaccg cgttactaaa acaggtaagt ccggcctccg cgccgggttt tggcgcctcc    720

cgcgggcgcc cccctcctca cggcgagcgc tgccacgtca gacgaagggc gcagcgagcg    780

tcctgatcct tccgcccgga cgctcaggac agcggcccgc tgctcataag actcggcctt    840

agaaccccag tatcagcaga aggacatttt aggacgggac ttgggtgact ctagggcact    900

ggttttcttt ccagagagcg gaacaggcga ggaaaagtag tcccttctcg gcgattctgc    960

ggagggatct ccgtggggcg gtgaacgccg atgatgcctc tactaaccat gttcatgttt   1020

tctttttttt tctacaggtc ctgggtgacg aacag                              1055
```

<210> SEQ ID NO 56
<211> LENGTH: 78

<212> TYPE: DNA
<213> ORGANISM: Homo sapiens
<220> FEATURE:
<221> NAME/KEY: HGH Signal Peptide
<222> LOCATION: (1)..(78)

<400> SEQUENCE: 56
atggcgacgg gttcaagaac ttccctactt cttgcatttg gcctgctttg tttgccgtgg 60
ttacaggagg gctcggca 78

<210> SEQ ID NO 57
<211> LENGTH: 96
<212> TYPE: DNA
<213> ORGANISM: Foot-and-mouth disease virus
<220> FEATURE:
<221> NAME/KEY: F2A
<222> LOCATION: (1)..(96)

<400> SEQUENCE: 57
cgaaaaagaa gatcaggttc gggtgcgcca gtaaagcaga cattaaactt tgatttgctg 60
aaacttgcag gtgatgtaga gtcaaatcca ggtcca 96

<210> SEQ ID NO 58
<211> LENGTH: 78
<212> TYPE: DNA
<213> ORGANISM: Homo sapiens
<220> FEATURE:
<221> NAME/KEY: HGH Signal Peptide Variant
<222> LOCATION: (1)..(78)

<400> SEQUENCE: 58
atggcaacag ggagccgaac ctctctgctc cttgctttcg ggctcctttg cctaccgtgg 60
ctccaagagg gctcggca 78

<210> SEQ ID NO 59
<211> LENGTH: 589
<212> TYPE: DNA
<213> ORGANISM: Hepatitis B virus
<220> FEATURE:
<221> NAME/KEY: WPRE
<222> LOCATION: (1)..(589)

<400> SEQUENCE: 59
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgc 589

<210> SEQ ID NO 60
<211> LENGTH: 135
<212> TYPE: DNA
<213> ORGANISM: Simian virus 40
<220> FEATURE:

```
<221> NAME/KEY: SV40 Poly A
<222> LOCATION: (1)..(135)

<400> SEQUENCE: 60

aacttgttta ttgcagctta taatggttac aaataaagca atagcatcac aaatttcaca     60

aataaagcat ttttttcact gcattctagt tgtggtttgt ccaaactcat caatgtatct    120

tatcatgtct ggatc                                                     135


<210> SEQ ID NO 61
<211> LENGTH: 8134
<212> TYPE: DNA
<213> ORGANISM: Artificial Sequence
<220> FEATURE:
<223> OTHER INFORMATION: Synthetic
<220> FEATURE:
<221> NAME/KEY: pACASI-15A7 genome
<222> LOCATION: (1)..(8134)

<400> SEQUENCE: 61

cagcagctgc gcgctcgctc gctcactgag gccgcccggg caaagcccgg gcgtcgggcg     60

acctttggtc gcccggcctc agtgagcgag cgagcgcgca gagagggagt ggccaactcc    120

atcactaggg gttccttgta gttaatgatt aacccgccat gctacttatc tacgtagcca    180

tgctctagga cattgattat tgactagtgg agttccgcgt tacataactt acggtaaatg    240

gcccgcctgg ctgaccgccc aacgaccccc gcccattgac gtcaataatg acgtatgttc    300

ccatagtaac gccaataggg actttccatt gacgtcaatg ggtggagtat ttacggtaaa    360

ctgcccactt ggcagtacat caagtgtatc atatgccaag tacgccccct attgacgtca    420

atgacggtaa atggcccgcc tggcattatg cccagtacat gaccttatgg gactttccta    480

cttggcagta catctacgta ttagtcatcg ctattaccat ggtcgaggtg agccccacgt    540

tctgcttcac tctccccatc tcccccccct ccccaccccc aattttgtat ttatttattt    600

tttaattatt ttgtgcagcg atgggggcgg gggggggggg gggcgcgcgc caggcggggc    660

ggggcggggc gaggggcggg gcggggcgag gcggagaggt gcggcggcag ccaatcagag    720

cggcgcgctc cgaaagtttc cttttatggc gaggcggcgg cggcggcggc cctataaaaa    780

gcgaagcgcg cggcgggcgg gagtcgctgc gcgctgcctt cgccccgtgc cccgctccgc    840

cgccgcctcg cgccgccccgc cccggctctg actgaccgcg ttactaaaac aggtaagtcc    900

ggcctccgcg ccgggttttg gcgcctcccg cgggcgcccc cctcctcacg gcgagcgctg    960

ccacgtcaga cgaagggcgc agcgagcgtc ctgatccttc cgcccggacg ctcaggacag   1020

cggcccgctg ctcataagac tcggccttag aaccccagta tcagcagaag gacattttag   1080

gacgggactt gggtgactct agggcactgg ttttctttcc agagagcgga acaggcgagg   1140

aaaagtagtc ccttctcggc gattctgcgg agggatctcc gtggggcggt gaacgccgat   1200

gatgcctcta ctaaccatgt tcatgttttc tttttttttc tacaggtcct gggtgacgaa   1260

cagggtaccg ccaccatggc gacgggttca agaacttccc tacttcttgc atttggcctg   1320

ctttgtttgc cgtggttaca ggagggctcg gcacaggtgc agctggtgca gtctggggct   1380

gaggtgaaga agcctggggc ctcagtgaag gtctcctgca aggcttctgg atacaccttc   1440

accagttatg atatcaactg ggtgcgacag gcctctggac aagggcttga gtggatggga   1500

tggatgaacc ctaacagtgc taacccaggc tatgcacaga agttccaggg cagagtcacc   1560

atgaccagga acacctccat aagcacagcc ttcatggagc tgagcagcct gagatctgac   1620

gacacggccg tgtattactg tgcgagagcc cgagtaacta tacattacga tattttgact   1680
```

```
ggttattatt cgaatgcttt tgatatctgg ggccaaggga caatggtcgc cgtctcttca   1740
agcaccaagg gcccatcggt cttcccctg gcaccctcct ccaagagcac ctctgggggc   1800
acagcggccc tgggctgcct ggtcaaggac tacttccccg aaccggtgac ggtgtcgtgg   1860
aactcaggcg ccctgaccag cggcgtgcac accttcccgg ctgtcctaca gtcctcagga   1920
ctctactccc tcagcagcgt ggtgaccgtg ccctccagca gcttgggcac ccagacctac   1980
atctgcaacg tgaatcacaa gcccagcaac accaaggtgg acaagaaagt tgagcccaaa   2040
tcttgtgaca aaactcacac atgcccaccg tgcccagcac ctgaactcct ggggggaccg   2100
tcagtcttcc tcttcccccc aaaacccaag gacaccctca tgatctcccg gacccctgag   2160
gtcacatgcg tggtggtgga cgtgagccac gaagaccctg aggtcaagtt caactggtac   2220
gtggacggcg tggaggtgca taatgccaag acaaagccgc gggaggagca gtacaacagc   2280
acgtaccgtg tggtcagcgt cctcaccgtc ctgcaccagg actggctgaa tggcaaggag   2340
tacaagtgca aggtctccaa caaagccctc ccagccccca tcgagaaaac catctccaaa   2400
gccaaagggc agccccgaga accacaggtg tacaccctgc ccccatcccg ggaggagatg   2460
accaagaacc aggtcagcct gacctgcctg gtcaaaggct tctatcccag cgacatcgcc   2520
gtggagtggg agagcaatgg gcagccggag aacaactaca agaccacgcc tcccgtgctg   2580
gactccgacg gctccttctt cctctacagc aagctcaccg tggacaagag caggtggcag   2640
caggggaacg tcttctcatg ctccgtgatg catgaggctc tgcacaacca ctacacgcag   2700
aagagcctct ccctgtctcc gggtaaacga aaaagaagat caggttcggg tgcgccagta   2760
aagcagacat taaactttga tttgctgaaa cttgcaggtg atgtagagtc aaatccaggt   2820
ccaatggcaa cagggagccg aacctctctg ctccttgctt tcgggctcct ttgcctaccg   2880
tggctccaag agggctcggc agacatccag atgacccagt ctccatcctc cctgtctgca   2940
tctgtaggag acagagtcac catcacttgc cgggcaagtc agaccattag cagctattta   3000
aattggtatc agcagaaacc agggaaagcc cctaagctcc tgatctatgc tgcatccagt   3060
ttgcaaagtg gggtcccatc aaggttcagt ggcagtggat ctggggcaga tttcactctc   3120
accatcagca gtctgcaacc tgaagatttt gcaacttact actgtcaaca gagttacact   3180
accttcatgt acacttttgg ccaggggacc atgctggaga tcaaaggtca gcccaaggct   3240
gcccccctcgg tcactctgtt cccgccctcc tctgaggagc ttcaagccaa caaggccaca   3300
ctggtgtgtc tcataagtga cttctacccg ggagccgtga cagtggcctg gaaggcagat   3360
agcagccccg tcaaggcggg agtggagacc accacaccct ccaaacaaag caacaacaag   3420
tacgcggcca gcagctatct gagcctgacg cctgagcagt ggaagtccca cagaagctac   3480
agctgccagg tcacgcatga agggagcacc gtggagaaga cagtggcccc tacagaatgt   3540
tcatagctct agaggataat caacctctgg attacaaaat ttgtgaaaga ttgactggta   3600
ttcttaacta tgttgctcct tttacgctat gtggatacgc tgctttaatg cctttgtatc   3660
atgctattgc ttcccgtatg gctttcattt tctcctcctt gtataaatcc tggttgctgt   3720
ctctttatga ggagttgtgg cccgttgtca ggcaacgtgg cgtggtgtgc actgtgtttg   3780
ctgacgcaac ccccactggt tggggcattg ccaccacctg tcagctcctt tccgggactt   3840
tcgctttccc cctccctatt gccacggcgg aactcatcgc cgcctgcctt gcccgctgct   3900
ggacaggggc tcggctgttg ggcactgaca attccgtggt gttgtcgggg aaatcatcgt   3960
cctttccttg gctgctcgcc tgtgttgcca cctggattct gcgcgggacg tccttctgct   4020
```

-continued

```
acgtcccttc ggccctcaat ccagcggacc ttccttcccg cggcctgctg ccggctctgc   4080
ggcctcttcc gcgtcttcgc cttcgccctc agacgagtcg gatctccctt tgggccgcct   4140
ccccgcctaa gcttatcgat accgtcgaga tctaacttgt ttattgcagc ttataatggt   4200
tacaaataaa gcaatagcat cacaaatttc acaaataaag catttttttc actgcattct   4260
agttgtggtt tgtccaaact catcaatgta tcttatcatg tctggatctc gacctcgact   4320
agagcatggc tacgtagata agtagcatgg cgggttaatc attaactaca aggaacccct   4380
agtgatggag ttggccactc cctctctgcg cgctcgctcg ctcactgagg ccgggcgacc   4440
aaaggtcgcc cgacgcccgg gctttgcccg ggcggcctca gtgagcgagc gagcgcgcca   4500
gctggcgtaa tagcgaagag gcccgcaccg atcgcccttc ccaacagttg cgcagcctga   4560
atggcgaatg gaattccaga cgattgagcg tcaaaatgta ggtatttcca tgagcgtttt   4620
tcctgttgca atggctggcg gtaatattgt tctggatatt accagcaagg ccgatagttt   4680
gagttcttct actcaggcaa gtgatgttat tactaatcaa agaagtattg cgacaacggt   4740
taatttgcgt gatggacaga ctcttttact cggtggcctc actgattata aaaacacttc   4800
tcaggattct ggcgtaccgt tcctgtctaa aatcccttta atcggcctcc tgtttagctc   4860
ccgctctgat tctaacgagg aaagcacgtt atacgtgctc gtcaaagcaa ccatagtacg   4920
cgccctgtag cggcgcatta agcgcggcgg gtgtggtggt tacgcgcagc gtgaccgcta   4980
cacttgccag cgccctagcg cccgctcctt tcgctttctt cccttccttt ctcgccacgt   5040
tcgccggctt tccccgtcaa gctctaaatc gggggctccc tttagggttc cgatttagtg   5100
ctttacggca cctcgacccc aaaaaacttg attagggtga tggttcacgt agtgggccat   5160
cgccctgata gacggttttt cgccctttga cgttggagtc cacgttcttt aatagtggac   5220
tcttgttcca aactggaaca acactcaacc ctatctcggt ctattctttt gatttataag   5280
ggattttgcc gatttcggcc tattggttaa aaaatgagct gatttaacaa aaatttaacg   5340
cgaattttaa caaaatatta acgtttacaa tttaaatatt tgcttataca atcttcctgt   5400
ttttggggct tttctgatta tcaaccgggg tacatatgat tgacatgcta gttttacgat   5460
taccgttcat cgattctctt gtttgctcca gactctcagg caatgacctg atagcctttg   5520
tagagacctc tcaaaaatag ctaccctctc cggcatgaat ttatcagcta gaacggttga   5580
atatcatatt gatggtgatt tgactgtctc cggcctttct cacccgtttg aatctttacc   5640
tacacattac tcaggcattg catttaaaat atatgagggt tctaaaaatt tttatccttg   5700
cgttgaaata aaggcttctc ccgcaaaagt attacagggt cataatgttt ttggtacaac   5760
cgatttagct ttatgctctg aggctttatt gcttaatttt gctaattctt tgccttgcct   5820
gtatgattta ttggatgttg gaattcctga tgcggtattt tctccttacg catctgtgcg   5880
gtatttcaca ccgcatatgg tgcactctca gtacaatctg ctctgatgcc gcatagttaa   5940
gccagccccg acacccgcca acacccgctg acgcgccctg acgggcttgt ctgctcccgg   6000
catccgctta cagacaagct gtgaccgtct ccgggagctg catgtgtcag aggttttcac   6060
cgtcatcacc gaaacgcgcg agacgaaagg gcctcgtgat acgcctattt ttataggtta   6120
atgtcatgat aataatggtt tcttagacgt caggtggcac ttttcgggga aatgtgcgcg   6180
gaacccctat ttgtttattt ttctaaatac attcaaatat gtatccgctc atgagacaat   6240
aaccctgata aatgcttcaa taatattgaa aaaggaagag tatgagtatt caacatttcc   6300
gtgtcgccct tattcccttt tttgcggcat tttgccttcc tgtttttgct cacccagaaa   6360
cgctggtgaa agtaaaagat gctgaagatc agttgggtgc acgagtgggt tacatcgaac   6420
```

```
tggatctcaa cagcggtaag atccttgaga gttttcgccc cgaagaacgt tttccaatga   6480

tgagcacttt taaagttctg ctatgtggcg cggtattatc ccgtattgac gccgggcaag   6540

agcaactcgg tcgccgcata cactattctc agaatgactt ggttgagtac tcaccagtca   6600

cagaaaagca tcttacggat ggcatgacag taagagaatt atgcagtgct gccataacca   6660

tgagtgataa cactgcggcc aacttacttc tgacaacgat cggaggaccg aaggagctaa   6720

ccgctttttt gcacaacatg ggggatcatg taactcgcct tgatcgttgg gaaccggagc   6780

tgaatgaagc cataccaaac gacgagcgtg acaccacgat gcctgtagca atggcaacaa   6840

cgttgcgcaa actattaact ggcgaactac ttactctagc ttcccggcaa caattaatag   6900

actggatgga ggcggataaa gttgcaggac cacttctgcg ctcggccctt ccggctggct   6960

ggtttattgc tgataaatct ggagccggtg agcgtgggtc tcgcggtatc attgcagcac   7020

tggggccaga tggtaagccc tcccgtatcg tagttatcta cacgacgggg agtcaggcaa   7080

ctatggatga acgaaataga cagatcgctg agataggtgc ctcactgatt aagcattggt   7140

aactgtcaga ccaagtttac tcatatatac tttagattga tttaaaactt catttttaat   7200

ttaaaaggat ctaggtgaag atcctttttg ataatctcat gaccaaaatc ccttaacgtg   7260

agttttcgtt ccactgagcg tcagaccccg tagaaaagat caaaggatct tcttgagatc   7320

cttttttct gcgcgtaatc tgctgcttgc aaacaaaaaa accaccgcta ccagcggtgg   7380

tttgtttgcc ggatcaagag ctaccaactc tttttccgaa ggtaactggc ttcagcagag   7440

cgcagatacc aaatactgtc cttctagtgt agccgtagtt aggccaccac ttcaagaact   7500

ctgtagcacc gcctacatac ctcgctctgc taatcctgtt accagtggct gctgccagtg   7560

gcgataagtc gtgtcttacc gggttggact caagacgata gttaccggat aaggcgcagc   7620

ggtcgggctg aacggggggt tcgtgcacac agcccagctt ggagcgaacg acctacaccg   7680

aactgagata cctacagcgt gagctatgag aaagcgccac gcttcccgaa gggagaaagg   7740

cggacaggta tccggtaagc ggcagggtcg gaacaggaga gcgcacgagg gagcttccag   7800

ggggaaacgc ctggtatctt tatagtcctg tcgggtttcg ccacctctga cttgagcgtc   7860

gatttttgtg atgctcgtca ggggggcgga gcctatggaa aaacgccagc aacgcggcct   7920

ttttacggtt cctggccttt tgctggcctt ttgctcacat gttctttcct gcgttatccc   7980

ctgattctgt ggataaccgt attaccgcct ttgagtgagc tgataccgct cgccgcagcc   8040

gaacgaccga gcgcagcgag tcagtgagcg aggaagcgga agagcgccca atacgcaaac   8100

cgcctctccc cgcgcgttgg ccgattcatt aatg                              8134
```

<210> SEQ ID NO 62
<211> LENGTH: 8116
<212> TYPE: DNA
<213> ORGANISM: Artificial Sequence
<220> FEATURE:
<223> OTHER INFORMATION: Synthetic
<220> FEATURE:
<221> NAME/KEY: pACASI-31C2 genome
<222> LOCATION: (1)..(8116)

<400> SEQUENCE: 62

```
cagcagctgc gcgctcgctc gctcactgag gccgcccggg caaagcccgg gcgtcgggcg     60

acctttggtc gcccggcctc agtgagcgag cgagcgcgca gagagggagt ggccaactcc    120

atcactaggg gttccttgta gttaatgatt aacccgccat gctacttatc tacgtagcca    180

tgctctagga cattgattat tgactagtgg agttccgcgt tacataactt acggtaaatg    240
```

```
gcccgcctgg ctgaccgccc aacgaccccc gcccattgac gtcaataatg acgtatgttc    300
ccatagtaac gccaataggg actttccatt gacgtcaatg ggtggagtat ttacggtaaa    360
ctgcccactt ggcagtacat caagtgtatc atatgccaag tacgccccct attgacgtca    420
atgacggtaa atggcccgcc tggcattatg cccagtacat gaccttatgg gactttccta    480
cttggcagta catctacgta ttagtcatcg ctattaccat ggtcgaggtg agccccacgt    540
tctgcttcac tctccccatc tcccccccct ccccaccccc aattttgtat ttatttattt    600
tttaattatt ttgtgcagcg atgggggcgg gggggggggg gggcgcgcgc caggcggggc    660
ggggcggggc gaggggcggg gcggggcgag gcggagaggt gcggcggcag ccaatcagag    720
cggcgcgctc cgaaagtttc cttttatggc gaggcggcgg cggcggcggc cctataaaaa    780
gcgaagcgcg cggcgggcgg gagtcgctgc gcgctgcctt cgccccgtgc cccgctccgc    840
cgccgcctcg cgccgcccgc cccggctctg actgaccgcg ttactaaaac aggtaagtcc    900
ggcctccgcg ccgggttttg gcgcctcccg cgggcgcccc cctcctcacg gcgagcgctg    960
ccacgtcaga cgaagggcgc agcgagcgtc ctgatccttc cgcccggacg ctcaggacag   1020
cggcccgctg ctcataagac tcggccttag aaccccagta tcagcagaag gacattttag   1080
gacgggactt gggtgactct agggcactgg ttttctttcc agagagcgga acaggcgagg   1140
aaaagtagtc ccttctcggc gattctgcgg agggatctcc gtggggcggt gaacgccgat   1200
gatgcctcta ctaaccatgt tcatgttttc tttttttttc tacaggtcct gggtgacgaa   1260
cagggtaccg ccaccatggc gacgggttca agaacttccc tacttcttgc atttggcctg   1320
ctttgtttgc cgtggttaca ggagggctcg gcacaggtgc agctggtgca gtctggggct   1380
gaggtgaaga agcctgggtc gtcggtgaag gtctcctgca aggcttctgg aggcaccttc   1440
agcagctatg ctatcagctg ggtgcgacag gcccctggac aagggcttga gtggatggga   1500
gggatcatcc ctatctttgg tacaacaaac tacgcacaga agttccaggg cagagtcacg   1560
attaccgcgg acgaatccac gagcacagcc tacatggagc tgaacagcct gagatctgag   1620
gacacggccg tgtattactg tgcgggacgt tcggcctacg gtgataaagg gtactacttt   1680
gattactggg gccagggaac cctggtcacc gtctcctcaa gcaccaaggg cccatcggtc   1740
ttccccctgg caccctcctc caagagcacc tctgggggca cagcggccct gggctgcctg   1800
gtcaaggact acttccccga accggtgacg gtgtcgtgga actcaggcgc cctgaccagc   1860
ggcgtgcaca ccttcccggc tgtcctacag tcctcaggac tctactccct cagcagcgtg   1920
gtgaccgtgc cctccagcag cttgggcacc cagacctaca tctgcaacgt gaatcacaag   1980
cccagcaaca ccaaggtgga caagaaagtt gagcccaaat cttgtgacaa aactcacaca   2040
tgcccaccgt gcccagcacc tgaactcctg gggggaccgt cagtcttcct cttcccccca   2100
aaacccaagg acaccctcat gatctcccgg acccctgagg tcacatgcgt ggtggtggac   2160
gtgagccacg aagaccctga ggtcaagttc aactggtacg tggacggcgt ggaggtgcat   2220
aatgccaaga caaagccgcg ggaggagcag tacaacagca cgtaccgtgt ggtcagcgtc   2280
ctcaccgtcc tgcaccagga ctggctgaat ggcaaggagt acaagtgcaa ggtctccaac   2340
aaagccctcc cagcccccat cgagaaaacc atctccaaag ccaaagggca gccccgagaa   2400
ccacaggtgt acaccctgcc cccatcccgg gaggagatga ccaagaacca ggtcagcctg   2460
acctgcctgg tcaaaggctt ctatcccagc gacatcgccg tggagtggga gagcaatggg   2520
cagccggaga acaactacaa gaccacgcct cccgtgctgg actccgacgg ctccttcttc   2580
```

```
ctctacagca agctcaccgt ggacaagagc aggtggcagc aggggaacgt cttctcatgc   2640
tccgtgatgc atgaggctct gcacaaccac tacacgcaga agagcctctc cctgtctccg   2700
ggtaaacgaa aaagaagatc aggttcgggt gcgccagtaa agcagacatt aaactttgat   2760
ttgctgaaac ttgcaggtga tgtagagtca aatccaggtc caatggcaac agggagccga   2820
acctctctgc tccttgcttt cgggctcctt tgcctaccgt ggctccaaga gggctcggca   2880
gaaattgtgt tgacacagtc tccagccacc ctgtctttgt ctccagggga aagagccacc   2940
ctctcctgca gggccagtca gagtgttagc aacttcttag cctggtatca acagaaacct   3000
ggccaggctc ccaggctcct catctatgat gcatccaaca gggccactgg catcccagcc   3060
aggttcagtg gcagtgggtc tgggacagac ttcactctca ccatcagcag cctacagcct   3120
gaagattttg cagtttatta ctgtcagcag cgtagcaact ggcctccgca agagacgttc   3180
ggccaaggga ccaaggtgga aatcaaaggt cagcccaagg ctgccccctc ggtcactctg   3240
ttcccgccct cctctgagga gcttcaagcc aacaaggcca cactggtgtg tctcataagt   3300
gacttctacc cgggagccgt gacagtggcc tggaaggcag atagcagccc cgtcaaggcg   3360
ggagtggaga ccaccacacc ctccaaacaa agcaacaaca agtacgcggc cagcagctat   3420
ctgagcctga cgcctgagca gtggaagtcc cacagaagct acagctgcca ggtcacgcat   3480
gaagggagca ccgtggagaa gacagtggcc cctacagaat gttcatagct ctagaggata   3540
atcaacctct ggattacaaa atttgtgaaa gattgactgg tattcttaac tatgttgctc   3600
cttttacgct atgtggatac gctgctttaa tgcctttgta tcatgctatt gcttcccgta   3660
tggctttcat tttctcctcc ttgtataaat cctggttgct gtctctttat gaggagttgt   3720
ggcccgttgt caggcaacgt ggcgtggtgt gcactgtgtt tgctgacgca acccccactg   3780
gttggggcat tgccaccacc tgtcagctcc tttccgggac tttcgctttc ccctccccta   3840
ttgccacggc ggaactcatc gccgcctgcc ttgcccgctg ctggacaggg gctcggctgt   3900
tgggcactga caattccgtg gtgttgtcgg ggaaatcatc gtcctttcct tggctgctcg   3960
cctgtgttgc cacctggatt ctgcgcggga cgtccttctg ctacgtccct tcggccctca   4020
atccagcgga ccttccttcc cgcggcctgc tgccggctct gcggcctctt ccgcgtcttc   4080
gccttcgccc tcagacgagt cggatctccc tttgggccgc ctccccgcct aagcttatcg   4140
ataccgtcga gatctaactt gtttattgca gcttataatg gttacaaata aagcaatagc   4200
atcacaaatt tcacaaataa agcatttttt tcactgcatt ctagttgtgg tttgtccaaa   4260
ctcatcaatg tatcttatca tgtctggatc tcgacctcga ctagagcatg gctacgtaga   4320
taagtagcat ggcgggttaa tcattaacta caaggaaccc ctagtgatgg agttggccac   4380
tccctctctg cgcgctcgct cgctcactga ggccgggcga ccaaaggtcg cccgacgccc   4440
gggctttgcc cgggcggcct cagtgagcga gcgagcgcgc cagctggcgt aatagcgaag   4500
aggcccgcac cgatcgccct tcccaacagt tgcgcagcct gaatggcgaa tggaattcca   4560
gacgattgag cgtcaaaatg taggtatttc catgagcgtt tttcctgttg caatggctgg   4620
cggtaatatt gttctggata ttaccagcaa ggccgatagt ttgagttctt ctactcaggc   4680
aagtgatgtt attactaatc aaagaagtat tgcgacaacg gttaatttgc gtgatggaca   4740
gactctttta ctcggtggcc tcactgatta taaaaacact tctcaggatt ctggcgtacc   4800
gttcctgtct aaaatccctt taatcggcct cctgtttagc tcccgctctg attctaacga   4860
ggaaagcacg ttatacgtgc tcgtcaaagc aaccatagta cgcgccctgt agcggcgcat   4920
taagcgcggc gggtgtggtg gttacgcgca gcgtgaccgc tacacttgcc agcgccctag   4980
```

```
cgcccgctcc tttcgctttc ttcccttcct ttctcgccac gttcgccggc tttccccgtc   5040
aagctctaaa tcgggggctc cctttagggt tccgatttag tgctttacgg cacctcgacc   5100
ccaaaaaact tgattagggt gatggttcac gtagtgggcc atcgccctga tagacggttt   5160
ttcgcccttt gacgttggag tccacgttct ttaatagtgg actcttgttc caaactggaa   5220
caacactcaa ccctatctcg gtctattctt ttgatttata agggattttg ccgatttcgg   5280
cctattggtt aaaaaatgag ctgatttaac aaaaatttaa cgcgaatttt aacaaaatat   5340
taacgtttac aatttaaata tttgcttata caatcttcct gtttttgggg cttttctgat   5400
tatcaaccgg ggtacatatg attgacatgc tagttttacg attaccgttc atcgattctc   5460
ttgtttgctc cagactctca ggcaatgacc tgatagcctt tgtagagacc tctcaaaaat   5520
agctaccctc tccggcatga atttatcagc tagaacggtt gaatatcata ttgatggtga   5580
tttgactgtc tccggccttt ctcacccgtt tgaatcttta cctacacatt actcaggcat   5640
tgcatttaaa atatatgagg gttctaaaaa tttttatcct tgcgttgaaa taaaggcttc   5700
tcccgcaaaa gtattacagg gtcataatgt ttttggtaca accgatttag ctttatgctc   5760
tgaggcttta ttgcttaatt ttgctaattc tttgccttgc ctgtatgatt tattggatgt   5820
tggaattcct gatgcggtat tttctcctta cgcatctgtg cggtatttca caccgcatat   5880
ggtgcactct cagtacaatc tgctctgatg ccgcatagtt aagccagccc cgacacccgc   5940
caacacccgc tgacgcgccc tgacgggctt gtctgctccc ggcatccgct tacagacaag   6000
ctgtgaccgt ctccgggagc tgcatgtgtc agaggttttc accgtcatca ccgaaacgcg   6060
cgagacgaaa gggcctcgtg atacgcctat ttttataggt taatgtcatg ataataatgg   6120
tttcttagac gtcaggtggc acttttcggg gaaatgtgcg cggaacccct atttgtttat   6180
ttttctaaat acattcaaat atgtatccgc tcatgagaca ataaccctga taaatgcttc   6240
aataatattg aaaaaggaag agtatgagta ttcaacattt ccgtgtcgcc cttattccct   6300
tttttgcggc attttgcctt cctgtttttg ctcacccaga aacgctggtg aaagtaaaag   6360
atgctgaaga tcagttgggt gcacgagtgg gttacatcga actggatctc aacagcggta   6420
agatccttga gagttttcgc cccgaagaac gttttccaat gatgagcact tttaaagttc   6480
tgctatgtgg cgcggtatta tcccgtattg acgccgggca agagcaactc ggtcgccgca   6540
tacactattc tcagaatgac ttggttgagt actcaccagt cacagaaaag catcttacgg   6600
atggcatgac agtaagagaa ttatgcagtg ctgccataac catgagtgat aacactgcgg   6660
ccaacttact tctgacaacg atcggaggac cgaaggagct aaccgctttt ttgcacaaca   6720
tgggggatca tgtaactcgc cttgatcgtt gggaaccgga gctgaatgaa gccataccaa   6780
acgacgagcg tgacaccacg atgcctgtag caatggcaac aacgttgcgc aaactattaa   6840
ctggcgaact acttactcta gcttcccggc aacaattaat agactggatg gaggcggata   6900
aagttgcagg accacttctg cgctcggccc ttccggctgg ctggtttatt gctgataaat   6960
ctggagccgg tgagcgtggg tctcgcggta tcattgcagc actggggcca gatggtaagc   7020
cctcccgtat cgtagttatc tacacgacgg ggagtcaggc aactatggat gaacgaaata   7080
gacagatcgc tgagataggt gcctcactga ttaagcattg gtaactgtca gaccaagttt   7140
actcatatat actttagatt gatttaaaac ttcattttta atttaaaagg atctaggtga   7200
agatcctttt tgataatctc atgaccaaaa tcccttaacg tgagttttcg ttccactgag   7260
cgtcagaccc cgtagaaaag atcaaaggat cttcttgaga tccttttttt ctgcgcgtaa   7320
```

```
tctgctgctt gcaaacaaaa aaaccaccgc taccagcggt ggtttgtttg ccggatcaag   7380

agctaccaac tctttttccg aaggtaactg gcttcagcag agcgcagata ccaaatactg   7440

tccttctagt gtagccgtag ttaggccacc acttcaagaa ctctgtagca ccgcctacat   7500

acctcgctct gctaatcctg ttaccagtgg ctgctgccag tggcgataag tcgtgtctta   7560

ccgggttgga ctcaagacga tagttaccgg ataaggcgca gcggtcgggc tgaacggggg   7620

gttcgtgcac acagcccagc ttggagcgaa cgacctacac cgaactgaga tacctacagc   7680

gtgagctatg agaaagcgcc acgcttcccg aagggagaaa ggcggacagg tatccggtaa   7740

gcggcagggt cggaacagga gagcgcacga gggagcttcc agggggaaac gcctggtatc   7800

tttatagtcc tgtcgggttt cgccacctct gacttgagcg tcgatttttg tgatgctcgt   7860

caggggggcg gagcctatgg aaaaacgcca gcaacgcggc ctttttacgg ttcctggcct   7920

tttgctggcc ttttgctcac atgttctttc ctgcgttatc ccctgattct gtggataacc   7980

gtattaccgc ctttgagtga gctgataccg ctcgccgcag ccgaacgacc gagcgcagcg   8040

agtcagtgag cgaggaagcg gaagagcgcc caatacgcaa accgcctctc cccgcgcgtt   8100

ggccgattca ttaatg                                                    8116
```

```
<210> SEQ ID NO 63
<211> LENGTH: 8105
<212> TYPE: DNA
<213> ORGANISM: Artificial Sequence
<220> FEATURE:
<223> OTHER INFORMATION: Synthetic
<220> FEATURE:
<221> NAME/KEY: pACASI-37G2 genome
<222> LOCATION: (1)..(8105)

<400> SEQUENCE: 63
```

```
cagcagctgc gcgctcgctc gctcactgag gccgcccggg caaagcccgg gcgtcgggcg     60

acctttggtc gcccggcctc agtgagcgag cgagcgcgca gagagggagt ggccaactcc    120

atcactaggg gttccttgta gttaatgatt aacccgccat gctacttatc tacgtagcca    180

tgctctagga cattgattat tgactagtgg agttccgcgt tacataactt acggtaaatg    240

gcccgcctgg ctgaccgccc aacgaccccc gcccattgac gtcaataatg acgtatgttc    300

ccatagtaac gccaataggg actttccatt gacgtcaatg ggtggagtat ttacggtaaa    360

ctgcccactt ggcagtacat caagtgtatc atatgccaag tacgccccct attgacgtca    420

atgacggtaa atggcccgcc tggcattatg cccagtacat gaccttatgg gactttccta    480

cttggcagta catctacgta ttagtcatcg ctattaccat ggtcgaggtg agccccacgt    540

tctgcttcac tctccccatc tcccccccct ccccaccccc aattttgtat ttatttattt    600

tttaattatt ttgtgcagcg atgggggcgg gggggggggg ggggcgcgcgc caggcggggc    660

ggggcggggc gaggggcggg gcggggcgag gcggagaggt gcggcggcag ccaatcagag    720

cggcgcgctc cgaaagtttc cttttatggc gaggcggcgg cggcggcggc cctataaaaa    780

gcgaagcgcg cggcgggcgg gagtcgctgc gcgctgcctt cgccccgtgc cccgctccgc    840

cgccgcctcg cgccgcccgc cccggctctg actgaccgcg ttactaaaac aggtaagtcc    900

ggcctccgcg ccgggttttg gcgcctcccg cgggcgcccc cctcctcacg gcgagcgctg    960

ccacgtcaga cgaagggcgc agcgagcgtc ctgatccttc cgcccggacg ctcaggacag   1020

cggcccgctg ctcataagac tcggccttag aaccccagta tcagcagaag gacattttag   1080

gacgggactt gggtgactct agggcactgg ttttctttcc agagagcgga acaggcgagg   1140
```

```
aaaagtagtc ccttctcggc gattctgcgg agggatctcc gtggggcggt gaacgccgat   1200
gatgcctcta ctaaccatgt tcatgttttc tttttttttc tacaggtcct gggtgacgaa   1260
cagggtaccg ccaccatggc gacgggttca agaacttccc tacttcttgc atttggcctg   1320
ctttgtttgc cgtggttaca ggagggctcg gcacaggtgc agctggtgca gtctggggct   1380
gaggtgaaga agcctgggtc ctcggtgaag gtctcctgca aggcttctgg aggcaccttc   1440
agcagctatg ctatcacctg ggtgcgacag gcccctggac aagggcttga gtggatggga   1500
gggatcatcc ctatctttgg tacagcaaac ttcgcacaga agttccaggg cagagtcacg   1560
attaccgcgg acgaatccac gagcacagcc tacatggagc tgagcagcct gagatctgag   1620
gacacggccg tgtattactg tgcccaccta ggggggttcg ctgacccctt tgactactgg   1680
ggccagggaa ccctggtcac cgtctcctca agcaccaagg gcccatcggt cttccccctg   1740
gcaccctcct ccaagagcac ctctgggggc acagcggccc tgggctgcct ggtcaaggac   1800
tacttccccg aaccggtgac ggtgtcgtgg aactcaggcg ccctgaccag cggcgtgcac   1860
accttcccgg ctgtcctaca gtcctcagga ctctactccc tcagcagcgt ggtgaccgtg   1920
ccctccagca gcttgggcac ccagacctac atctgcaacg tgaatcacaa gcccagcaac   1980
accaaggtgg acaagaaagt tgagcccaaa tcttgtgaca aaactcacac atgcccaccg   2040
tgcccagcac ctgaactcct ggggggaccg tcagtcttcc tcttcccccc aaaacccaag   2100
gacaccctca tgatctcccg gacccctgag gtcacatgcg tggtggtgga cgtgagccac   2160
gaagaccctg aggtcaagtt caactggtac gtggacggcg tggaggtgca taatgccaag   2220
acaaagccgc gggaggagca gtacaacagc acgtaccgtg tggtcagcgt cctcaccgtc   2280
ctgcaccagg actggctgaa tggcaaggag tacaagtgca aggtctccaa caaagccctc   2340
ccagccccca tcgagaaaac catctccaaa gccaaagggc agccccgaga accacaggtg   2400
tacaccctgc ccccatcccg ggaggagatg accaagaacc aggtcagcct gacctgcctg   2460
gtcaaaggct tctatcccag cgacatcgcc gtggagtggg agagcaatgg gcagccggag   2520
aacaactaca agaccacgcc tcccgtgctg gactccgacg gctccttctt cctctacagc   2580
aagctcaccg tggacaagag caggtggcag caggggaacg tcttctcatg ctccgtgatg   2640
catgaggctc tgcacaacca ctacacgcag aagagcctct ccctgtctcc gggtaaacga   2700
aaaagaagat caggttcggg tgcgccagta aagcagacat taaactttga tttgctgaaa   2760
cttgcaggtg atgtagagtc aaatccaggt ccaatggcaa cagggagccg aacctctctg   2820
ctccttgctt tcgggctcct ttgcctaccg tggctccaag agggctcggc agaaattgtg   2880
ttgacacagt ctccagccac cctgtctttg tctccagggg aaagagccac cctctcctgc   2940
agggccagtc agagtgttag caactactta gcctggtatc aacagaaagc tggccaggct   3000
cccagggtcc tcatctatga tgcattcaac agggccactg gcatcccagc caggttcagt   3060
ggcagtgggt ctgggacaga cttcactctc accatcagca gcctagagcc tgaagatttt   3120
gcagtttatt actgtcagca gcgtagcaac tggcctccgc ggatcacctt cggccaaggg   3180
acacgactgg agattaaagg tcagcccaag gctgccccct cggtcactct gttcccgccc   3240
tcctctgagg agcttcaagc caacaaggcc acactggtgt gtctcataag tgacttctac   3300
ccgggagccg tgacagtggc ctggaaggca gatagcagcc ccgtcaaggc gggagtggag   3360
accaccacac cctccaaaca aagcaacaac aagtacgcgg ccagcagcta tctgagcctg   3420
acgcctgagc agtggaagtc ccacagaagc tacagctgcc aggtcacgca tgaagggagc   3480
accgtggaga agacagtggc ccctacagaa tgttcatagc tctagaataa tcaacctctg   3540
```

```
gattacaaaa tttgtgaaag attgactggt attcttaact atgttgctcc ttttacgcta   3600
tgtggatacg ctgctttaat gcctttgtat catgctattg cttcccgtat ggctttcatt   3660
ttctcctcct tgtataaatc ctggttgctg tctctttatg aggagttgtg gcccgttgtc   3720
aggcaacgtg gcgtggtgtg cactgtgttt gctgacgcaa cccccactgg ttggggcatt   3780
gccaccacct gtcagctcct ttccgggact ttcgctttcc ccctccctat tgccacggcg   3840
gaactcatcg ccgcctgcct tgcccgctgc tggacagggg ctcggctgtt gggcactgac   3900
aattccgtgg tgttgtcggg gaaatcatcg tcctttcctt ggctgctcgc ctgtgttgcc   3960
acctggattc tgcgcgggac gtccttctgc tacgtccctt cggccctcaa tccagcggac   4020
cttccttccc gcggcctgct gccggctctg cggcctcttc cgcgtcttcg ccttcgccct   4080
cagacgagtc ggatctccct ttgggccgcc tccccgccta agcttatcga taccgtcgag   4140
atctaacttg tttattgcag cttataatgg ttacaaataa agcaatagca tcacaaattt   4200
cacaaataaa gcattttttt cactgcattc tagttgtggt ttgtccaaac tcatcaatgt   4260
atcttatcat gtctggatct cgacctcgac tagagcatgg ctacgtagat aagtagcatg   4320
gcgggttaat cattaactac aaggaacccc tagtgatgga gttggccact ccctctctgc   4380
gcgctcgctc gctcactgag gccgggcgac caaaggtcgc ccgacgcccg ggctttgccc   4440
gggcggcctc agtgagcgag cgagcgcgcc agctggcgta atagcgaaga ggcccgcacc   4500
gatcgccctt cccaacagtt gcgcagcctg aatggcgaat ggaattccag acgattgagc   4560
gtcaaaatgt aggtatttcc atgagcgttt ttcctgttgc aatggctggc ggtaatattg   4620
ttctggatat taccagcaag gccgatagtt tgagttcttc tactcaggca agtgatgtta   4680
ttactaatca aagaagtatt gcgacaacgg ttaatttgcg tgatggacag actcttttac   4740
tcggtggcct cactgattat aaaaacactt ctcaggattc tggcgtaccg ttcctgtcta   4800
aaatcccttt aatcggcctc ctgtttagct cccgctctga ttctaacgag gaaagcacgt   4860
tatacgtgct cgtcaaagca accatagtac gcgccctgta gcggcgcatt aagcgcggcg   4920
ggtgtggtgg ttacgcgcag cgtgaccgct acacttgcca gcgccctagc gcccgctcct   4980
ttcgctttct tcccttcctt tctcgccacg ttcgccggct ttccccgtca agctctaaat   5040
cgggggctcc ctttagggtt ccgatttagt gctttacggc acctcgaccc caaaaaactt   5100
gattagggtg atggttcacg tagtgggcca tcgccctgat agacggtttt tcgccctttg   5160
acgttggagt ccacgttctt taatagtgga ctcttgttcc aaactggaac aacactcaac   5220
cctatctcgg tctattcttt tgatttataa gggattttgc cgatttcggc ctattggtta   5280
aaaaatgagc tgatttaaca aaaatttaac gcgaatttta acaaaatatt aacgtttaca   5340
atttaaatat ttgcttatac aatcttcctg tttttggggc ttttctgatt atcaaccggg   5400
gtacatatga ttgacatgct agttttacga ttaccgttca tcgattctct tgtttgctcc   5460
agactctcag gcaatgacct gatagccttt gtagagacct ctcaaaaata gctaccctct   5520
ccggcatgaa tttatcagct agaacggttg aatatcatat tgatggtgat ttgactgtct   5580
ccggcctttc tcacccgttt gaatctttac ctacacatta ctcaggcatt gcatttaaaa   5640
tatatgaggg ttctaaaaat ttttatcctt gcgttgaaat aaaggcttct cccgcaaaag   5700
tattacaggg tcataatgtt tttggtacaa ccgatttagc tttatgctct gaggctttat   5760
tgcttaattt tgctaattct ttgccttgcc tgtatgattt attggatgtt ggaattcctg   5820
atgcggtatt ttctccttac gcatctgtgc ggtatttcac accgcatatg gtgcactctc   5880
```

-continued

```
agtacaatct gctctgatgc cgcatagtta agccagcccc gacacccgcc aacacccgct   5940
gacgcgccct gacgggcttg tctgctcccg gcatccgctt acagacaagc tgtgaccgtc   6000
tccgggagct gcatgtgtca gaggttttca ccgtcatcac cgaaacgcgc gagacgaaag   6060
ggcctcgtga tacgcctatt tttataggtt aatgtcatga taataatggt ttcttagacg   6120
tcaggtggca cttttcgggg aaatgtgcgc ggaaccccta tttgtttatt tttctaaata   6180
cattcaaata tgtatccgct catgagacaa taaccctgat aaatgcttca ataatattga   6240
aaaaggaaga gtatgagtat tcaacatttc cgtgtcgccc ttattccctt ttttgcggca   6300
ttttgccttc ctgtttttgc tcacccagaa acgctggtga aagtaaaaga tgctgaagat   6360
cagttgggtg cacgagtggg ttacatcgaa ctggatctca acagcggtaa gatccttgag   6420
agttttcgcc ccgaagaacg ttttccaatg atgagcactt ttaaagttct gctatgtggc   6480
gcggtattat cccgtattga cgccgggcaa gagcaactcg gtcgccgcat acactattct   6540
cagaatgact tggttgagta ctcaccagtc acagaaaagc atcttacgga tggcatgaca   6600
gtaagagaat tatgcagtgc tgccataacc atgagtgata acactgcggc caacttactt   6660
ctgacaacga tcggaggacc gaaggagcta accgcttttt tgcacaacat gggggatcat   6720
gtaactcgcc ttgatcgttg ggaaccggag ctgaatgaag ccataccaaa cgacgagcgt   6780
gacaccacga tgcctgtagc aatggcaaca acgttgcgca aactattaac tggcgaacta   6840
cttactctag cttcccggca acaattaata gactggatgg aggcggataa agttgcagga   6900
ccacttctgc gctcggccct tccggctggc tggtttattg ctgataaatc tggagccggt   6960
gagcgtgggt ctcgcggtat cattgcagca ctggggccag atggtaagcc ctcccgtatc   7020
gtagttatct acacgacggg gagtcaggca actatggatg aacgaaatag acagatcgct   7080
gagataggtg cctcactgat taagcattgg taactgtcag accaagttta ctcatatata   7140
ctttagattg atttaaaact tcatttttaa tttaaaagga tctaggtgaa gatccttttt   7200
gataatctca tgaccaaaat cccttaacgt gagttttcgt tccactgagc gtcagacccc   7260
gtagaaaaga tcaaaggatc ttcttgagat cctttttttc tgcgcgtaat ctgctgcttg   7320
caaacaaaaa aaccaccgct accagcggtg gtttgtttgc cggatcaaga gctaccaact   7380
ctttttccga aggtaactgg cttcagcaga gcgcagatac caaatactgt ccttctagtg   7440
tagccgtagt taggccacca cttcaagaac tctgtagcac cgcctacata cctcgctctg   7500
ctaatcctgt taccagtggc tgctgccagt ggcgataagt cgtgtcttac cgggttggac   7560
tcaagacgat agttaccgga taaggcgcag cggtcgggct gaacgggggg ttcgtgcaca   7620
cagcccagct tggagcgaac gacctacacc gaactgagat acctacagcg tgagctatga   7680
gaaagcgcca cgcttcccga agggagaaag gcggacaggt atccggtaag cggcagggtc   7740
ggaacaggag agcgcacgag ggagcttcca gggggaaacg cctggtatct ttatagtcct   7800
gtcgggtttc gccacctctg acttgagcgt cgatttttgt gatgctcgtc aggggggcgg   7860
agcctatgga aaaacgccag caacgcggcc tttttacggt tcctggcctt ttgctggcct   7920
tttgctcaca tgttctttcc tgcgttatcc cctgattctg tggataaccg tattaccgcc   7980
tttgagtgag ctgataccgc tcgccgcagc cgaacgaccg agcgcagcga gtcagtgagc   8040
gaggaagcgg aagagcgccc aatacgcaaa ccgcctctcc ccgcgcgttg gccgattcat   8100
taatg                                                               8105
```

EXPRESSION VECTOR FOR ANTI-SARS-COV-2 NEUTRALIZING ANTIBODIES

CROSS-REFERENCE TO RELATED APPLICATIONS

This application claims priority from PCT Patent Application No. PCT/CN2021/072629 filed on Jan. 19, 2021. The PCT Patent Application is hereby expressly incorporated by reference herein in its entirety.

REFERENCE TO AN ELECTRONIC SEQUENCE LISTING

The instant application contains a Sequence Listing which has been submitted electronically in ASCII format and is herein incorporated by reference in its entirety. Said ASCII copy, created on Aug. 2, 2021, is named SequenceListing.txt and is 60 KB in size.

FIELD OF THE INVENTION

The present disclosure generally relates to expression vectors that express anti-SARS-COV-2 neutralizing antibodies.

BACKGROUND

The global pandemic of the coronavirus disease 2019 (COVID-19) caused by a new coronavirus, i.e. severe acute respiratory syndrome coronavirus 2 (SARS-CoV-2), has severely deteriorated public health and economy. While majority of the infected population showed mild symptoms, some progressed to acute respiratory distress syndrome and over 2,000,000 deaths have been reported to date.

The infection of SARS-CoV-2 to a host cell is mediated by a glycoprotein expressed on the virus envelope named a spike (S) glycoprotein, which comprises S1 subunit and S2 subunit. The S1 subunit contains the receptor-binding domain (RBD) that directly binds to the human angiotensin converting enzyme 2 (ACE2) receptor on the host cell, while the S2 subunit mediates the fusion of the virus envelope with the host cell membrane so as to facilitate the infection of the virus.

Convalescent patients' plasma has been used to treat other infections and has also been proved to be beneficial for both mild and severe COVID-19 patients, due to the neutralizing antibodies produced in plasma. However, convalescent plasma treatment is limited since the plasma was donated by people recovered from COVID-19 and cannot be produced on a large-scale.

Therefore, there is an urgent need for large-scale recombinant vectors delivering and producing neutralizing antibodies with highly potent neutralizing effects against SARS-COV-2.

SUMMARY OF THE INVENTION

Throughout the present disclosure, the articles "a", "an", and "the" are used herein to refer to one or to more than one (i.e., to at least one) of the grammatical object of the article. By way of example, "an antibody" means one antibody or more than one antibody.

In one respect, the present disclosure provides a recombinant expression vector comprising an expression cassette comprising a nucleic acid sequence encoding an anti-SARS-COV-2 neutralizing antibody or antigen-binding fragments thereof.

In some embodiments, the anti-SARS-COV-2 neutralizing antibody or the antigen-binding fragments thereof comprises heavy chain CDR (HCDR)1, HCDR2 and HCDR3 selected from amino acid sequences of:

a) SEQ ID NO: 1, SEQ ID NO: 2, and SEQ ID NO: 3;

b) SEQ ID NO: 11, SEQ ID NO: 12, and SEQ ID NO: 13; or c) SEQ ID NO: 21, SEQ ID NO: 22, and SEQ ID NO: 23.

In some embodiments, a) the HCDR1 is encoded by nucleic acid sequence of SEQ ID NO: 31, the HCDR2 is encoded by nucleic acid sequence of SEQ ID NO: 32, and the HCDR3 is encoded by nucleic acid sequence of SEQ ID NO: 33; b) the HCDR1 is encoded by nucleic acid sequence of SEQ ID NO: 39, the HCDR2 is encoded by nucleic acid sequence of SEQ ID NO: 40, and the HCDR3 is encoded by nucleic acid sequence of SEQ ID NO: 41; or c) the HCDR1 is encoded by nucleic acid sequence of SEQ ID NO: 47, the HCDR2 is encoded by nucleic acid sequence of SEQ ID NO: 48, and the HCDR3 is encoded by nucleic acid sequence of SEQ ID NO: 49.

The recombinant expression vector of any one of the preceding claims, wherein the anti-SARS-COV-2 neutralizing antibody or the antigen-binding fragments thereof further comprises light chain CDR (LCDR)1, LCDR2 and LCDR3 selected from amino acid sequences of:

a) SEQ ID NO: 4, SEQ ID NO: 5, and SEQ ID NO: 6;

b) SEQ ID NO: 14, SEQ ID NO: 15, and SEQ ID NO: 16; or c) SEQ ID NO: 24, SEQ ID NO: 25, and SEQ ID NO: 26.

In some embodiments, a) the LCDR1 is encoded by nucleic acid sequence of SEQ ID NO: 34, the LCDR2 is encoded by nucleic acid sequence of SEQ ID NO: 35, and the LCDR3 is encoded by nucleic acid sequence of SEQ ID NO: 36; b) the LCDR1 is encoded by nucleic acid sequence of SEQ ID NO: 42, the LCDR2 is encoded by nucleic acid sequence of SEQ ID NO: 43, and the LCDR3 is encoded by nucleic acid sequence of SEQ ID NO: 44; or c) the LCDR1 is encoded by nucleic acid sequence of SEQ ID NO: 50, the LCDR2 is encoded by nucleic acid sequence of SEQ ID NO: 51, and the LCDR3 is encoded by nucleic acid sequence of SEQ ID NO: 52.

In some embodiments, the anti-SARS-COV-2 neutralizing antibody or the antigen-binding fragments thereof comprises:

a) HCDR1 of SEQ ID NO: 1, HCDR2 of SEQ ID NO: 2, and HCDR3 of SEQ ID NO: 3, and LCDR1 of SEQ ID NO: 4, LCDR2 of SEQ ID NO: 5, and LCDR3 of SEQ ID NO: 6;

b) HCDR1 of SEQ ID NO: 11, HCDR2 of SEQ ID NO: 12, and HCDR3 of SEQ ID NO: 13, and LCDR1 of SEQ ID NO: 14, LCDR2 of SEQ ID NO: 15, and LCDR3 of SEQ ID NO: 16; or c) HCDR1 of SEQ ID NO: 21, HCDR2 of SEQ ID NO: 22, and HCDR3 of SEQ ID NO: 23, and LCDR1 of SEQ ID NO: 24, LCDR2 of SEQ ID NO: 25, and LCDR3 of SEQ ID NO: 26.

In some embodiments, a) the HCDR1 is encoded by nucleic acid sequence of SEQ ID NO: 31, the HCDR2 is encoded by nucleic acid sequence of SEQ ID NO: 32, the HCDR3 is encoded by nucleic acid sequence of SEQ ID NO: 33, the LCDR1 is encoded by nucleic acid sequence of SEQ ID NO: 34, the LCDR2 is encoded by nucleic acid sequence of SEQ ID NO: 35, and the LCDR3 is encoded by nucleic acid sequence of SEQ ID NO: 36;

b) the HCDR1 is encoded by nucleic acid sequence of SEQ ID NO: 39, the HCDR2 is encoded by nucleic acid sequence of SEQ ID NO: 40, the HCDR3 is encoded by nucleic acid sequence of SEQ ID NO: 41, the LCDR1 is encoded by nucleic acid sequence of SEQ ID NO: 42, the LCDR2 is encoded by nucleic acid sequence of SEQ ID NO: 43, and the LCDR3 is encoded by nucleic acid sequence of SEQ ID NO: 44; or c) the HCDR1 is encoded by nucleic acid sequence of SEQ ID NO: 47, the HCDR2 is encoded by nucleic acid sequence of SEQ ID NO: 48, and the HCDR3 is encoded by nucleic acid sequence of SEQ ID NO: 49, the LCDR1 is encoded by nucleic acid sequence of SEQ ID NO: 50, the LCDR2 is encoded by nucleic acid sequence of SEQ ID NO: 51, and the LCDR3 is encoded by nucleic acid sequence of SEQ ID NO: 52.

In some embodiments, the anti-SARS-COV-2 neutralizing antibody or an antigen-binding fragment thereof comprising a variable heavy chain variable region (VH) comprising an amino acid sequence of SEQ ID NO: 7, SEQ ID NO: 17, SEQ ID NO: 27, or a sequence having at least 80% (or at least 85%, 90%, 95%, 96%, 97%, 98%, 99%) sequence identity thereof.

In some embodiments, a) the VH comprising the amino acid sequence of SEQ ID NO: 7 is encoded by nucleic acid sequence of SEQ ID NO: 9; b) the VH comprising the amino acid sequence of SEQ ID NO: 17 is encoded by nucleic acid sequence of SEQ ID NO: 19, and c) the VH comprising the amino acid sequence of SEQ ID NO: 27 is encoded by nucleic acid sequence of SEQ ID NO: 29.

In some embodiments, the anti-SARS-COV-2 neutralizing antibody or an antigen-binding fragment thereof further comprising a light chain variable region (VL) comprising an amino acid sequence of SEQ ID NO: 8, SEQ ID NO: 18, SEQ ID NO: 28, or a sequence having at least 80% (or at least 85%, 90%, 95%, 96%, 97%, 98%, 99%) sequence identity thereof.

In some embodiments, a) the VL comprising the amino acid sequence of SEQ ID NO: 8 is encoded by nucleic acid sequence of SEQ ID NO: 10; b) the VL comprising the amino acid sequence of SEQ ID NO: 18 is encoded by nucleic acid sequence of SEQ ID NO: 20; and c) the VL comprising the amino acid sequence of SEQ ID NO: 28 is encoded by nucleic acid sequence of SEQ ID NO: 30.

In some embodiments, the anti-SARS-COV-2 neutralizing antibody or the antigen-binding fragments thereof comprises:

a) a VH comprising an amino acid sequence of SEQ ID NO: 7 and a VL comprising an amino acid sequence of SEQ ID NO: 8, or homologous sequences thereof having at least 80% (or at least 85%, 90%, 95%, 96%, 97%, 98%, 99%) sequence identity yet retaining specific binding affinity to SARS-CoV-2;

b) a VH comprising an amino acid sequence of SEQ ID NO: 17 and a VL comprising an amino acid sequence of SEQ ID NO: 18, or homologous sequences thereof having at least 80% (or at least 85%, 90%, 95%, 96%, 97%, 98%, 99%) sequence identity yet retaining specific binding affinity to SARS-CoV-2; or c) a VH comprising an amino acid sequence of SEQ ID NO: 27 and a VL comprising an amino acid sequence of SEQ ID NO: 28, or homologous sequences thereof having at least 80% (or at least 85%, 90%, 95%, 96%, 97%, 98%, 99%) sequence identity yet retaining specific binding affinity to SARS-CoV-2.

In some embodiments, d) the amino acid sequences of VH and VL of a) are encoded by nucleic acid sequences of SEQ ID NO: 9 and SEQ ID NO: 10, respectively; e) the amino acid sequences of VH and VL of b) are encoded by nucleic acid sequences of SEQ ID NO: 19 and SEQ ID NO: 20, respectively; 0 the amino acid sequences of VH and VL of c) are encoded by nucleic acid sequences of SEQ ID NO: 29 and SEQ ID NO: 30, respectively.

In some embodiments, the anti-SARS-COV-2 neutralizing antibody or antigen-binding fragment thereof further comprising one or more amino acid residue mutations yet retaining specific binding to SARS-CoV-2.

In some embodiments, at least one of the mutations is in one or more of the CDR sequences, and/or in one or more of the VH or VL sequences but not in any of the CDR sequences.

In some embodiments, the anti-SARS-COV-2 neutralizing antibody or antigen-binding fragment thereof is a diabody, a Fab, a Fab', a $F(ab')_2$, a Fd, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, or a bivalent domain antibody.

In some embodiments, the anti-SARS-COV-2 neutralizing antibody or antigen-binding fragment thereof is bispecific.

In some embodiments, the anti-SARS-COV-2 neutralizing antibody or antigen-binding fragment thereof further comprises a heavy chain constant region and/or a light chain constant region.

In some embodiments, the heavy chain constant region is from human IgG1. In some embodiments, the heavy chain constant region comprises amino acid sequence of SEQ ID NO: 37, optionally, the heavy chain constant region is encoded by nucleic acid sequence of SEQ ID NO: 38.

In some embodiments, the light chain constant region is from human lambda light chain. In some embodiments, the light chain constant region comprises amino acid sequence of SEQ ID NO: 45, optionally, the light chain constant region is encoded by nucleic acid sequence of SEQ ID NO: 46.

In some embodiments, a first signal peptide is operably linked to the anti-SARS-COV-2 neutralizing antibody VH at the N-terminal of the VH, and a second signal peptide is operably linked to the anti-SARS-COV-2 neutralizing antibody VL at the N-terminal of the VL.

In some embodiments, the expression cassette further comprises a transcriptional regulatory element. In some embodiments, the transcriptional regulatory element comprises one or more of promoters, enhancers, introns, 2A self-cleaving peptide sequences, woodchuck hepatitis virus post-transcriptional regulatory elements (WPREs) and/or polyadenylation (polyA) signal sequences.

In some embodiments, the recombinant expression vector is a virus-based vector. In some embodiments, the recombinant expression vector is a lentivirus vector. In some embodiments, the recombinant expression vector is a retroviral vector. In some embodiments, the recombinant expression vector is an adeno-associated virus (AAV) vector.

In some embodiments, the expression cassette comprises in an orientation from 5' to 3' of the sense strand: a 5' AAV inverted terminal repeat (ITR)1-a promoter-the nucleic acid sequence encoding the anti-SARS-COV-2 neutralizing antibody-WPRE-a polyA signal sequence-a 3' AAV ITR2. In some embodiments, the nucleic acid sequence encoding the anti-SARS-COV-2 neutralizing antibody comprises encoding sequences of: the first signal peptide-the anti-SARS- COV-2 neutralizing antibody heavy chain variable region-a human IgG1 constant region-2A self-cleaving peptide-the second signal peptide-the anti-SARS-COV-2 neutralizing antibody light chain variable region-a human lambda light chain constant region, in an orientation from 5' to 3' of the sense strand.

In some embodiments, the promoter is CASI promoter and the polyA signal sequence is SV40 polyA.

In some embodiments, the AAV ITR1 and AAV ITR2 are AAV2 ITRs.

In some embodiments, the AAV vector is pseudotyped with a mutated AAV6 capsid.

In some embodiments, the nucleic acid sequence encoding an anti-SARS-COV-2 neutralizing antibody or antigen-binding fragments thereof is codon optimized for expression.

In some embodiments, the recombinant expression vector a nucleic acid sequence of any one of SEQ ID NO: 61-63.

In another aspect, the present disclosure also provides a genetically modified host cell comprising the recombinant expression vector provided herein. In some embodiments, the cell is selected from a group consisting of an archaeal cell, a bacterial cell, and a eukaryotic cell. In some embodiments, the cell is a mammalian cell. In some embodiments, the mammalian cell is HEK293 cell.

In another aspect, the present disclosure also provides a pharmaceutical composition comprising the recombinant expression vector provided herein, and a pharmaceutically acceptable carrier.

In another aspect, the present disclosure also provides a method of producing a recombinant expression vector expressing an anti-SARS-COV-2 neutralizing antibody, comprising culturing the genetically modified host cell provided herein under a condition suitable for reproduction of the recombinant expression vector.

In another aspect, the present disclosure also provides a method of treating or preventing SARS-CoV-2 infection in a subject, comprising administering to the subject an effective amount of the recombinant expression vector provided herein or the above-mentioned pharmaceutical composition provided herein.

In some embodiments, the subject is human or non-human animal.

In some embodiments, the subject has been identified as having SARS-CoV-2 infection, or is suspected of having SARS-CoV-2 infection, or is at risk of exposure to SARS-CoV-2.

In some embodiments, the administration is via oral, nasal, intravenous, subcutaneous, sublingual, or intramuscular administration.

In some embodiments, the method further comprises administering an effective amount of a second therapeutic agent.

In some embodiments, the second therapeutic agent is selected from an antiviral agent. Examples of the antiviral agent can be a second SARS-CoV-2 neutralizing antibody, a second recombinant expression vector expressing a second SARS-CoV-2 neutralizing antibody, RNA dependent RNA polymerase inhibitor, a nucleoside analog, antiviral cytokines (such as interferons), or immunostimulatory agents.

In another aspect, the present disclosure also provides a method of neutralizing SARS-CoV-2 in a subject, comprising administering to the subject the recombinant expression vector provided herein.

In another aspect, the present disclosure also provides a method for preventing or reducing transmission of SARS-CoV-2 by a SARS-CoV-2 infected subject, comprising administering to the SARS-CoV-2 infected subject an effective amount of the recombinant expression vector provided herein, or the pharmaceutical composition provided herein.

In another aspect, the present disclosure also provides a method of reducing viral load in a SARS-CoV-2 infected subject, comprising administering to the subject an effective amount of the recombinant expression vector provided herein, or the pharmaceutical composition provided herein.

In another aspect, the present disclosure also provides use of the recombinant expression vector provided herein or the pharmaceutical composition provided herein in the manufacture of a medicament for treating or preventing SARS-CoV-2 infection in a subject; or for preventing, inhibiting progression of, and/or delaying the onset of SARS-CoV-2 infection or an SARS-CoV-2-associated condition in a subject; or for preventing or reducing transmission of SARS-CoV-2 by a SARS-CoV-2 infected subject; or for reducing viral load in a SARS-CoV-2 infected subject.

DETAILED DESCRIPTION OF THE INVENTION

Figure 1:
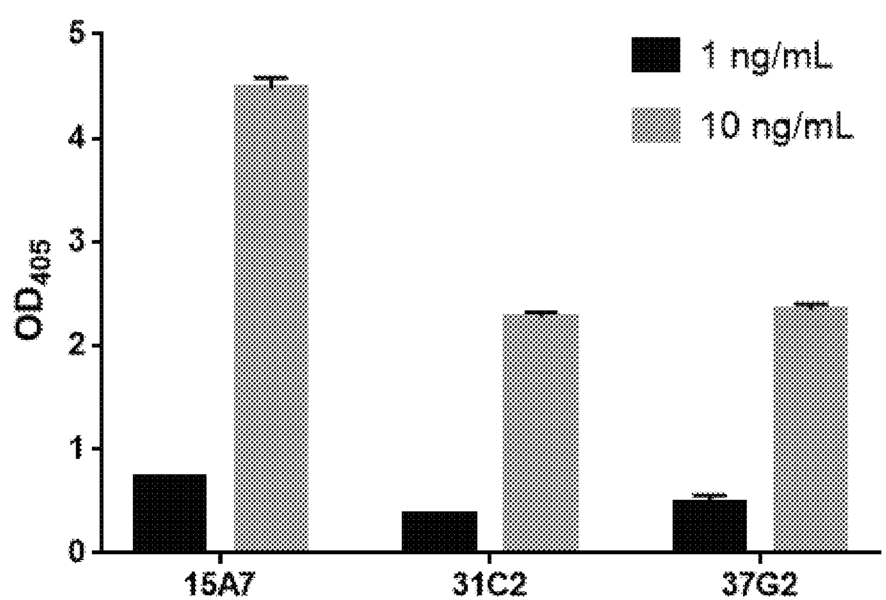
FIG. 1 shows binding profile of the antibodies provided in the disclosure with SARS-CoV-2 virus-like particles (VLP) as determined by ELISA.

The following description of the disclosure is merely intended to illustrate various embodiments of the disclosure. As such, the specific modifications discussed are not to be construed as limitations on the scope of the disclosure. It will be apparent to a person skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definition

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region (VH) and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.,* 273(4), 927 (1997); Chothia, C. et al., *J Mol Biol*. December 5; 186(3):651-63 (1985); Chothia, C. and Lesk, A. M., *J. Mol. Biol.,* 196,901 (1987); Chothia, C. et al., *Nature*. December 21-28; 342(6252):877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology,* 27: 55-77 (2003); Marie-Paule Lefranc et al., *Immunome Research,* 1(3), (2005); Marie-Paule Lefranc, Molecular Biology of B cells (second edition), chapter 26, 481-514, (2015)). The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are large immunoglobulin A (IgA), IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

In certain embodiments, the antibody provided herein encompasses any antigen-binding fragments thereof. The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragments include, without limitation, a diabody, a Fab, a Fab', a $F(ab)_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab" refers to a Fab fragment that includes a portion of the hinge region.

"$F(ab')_2$" refers to a dimer of Fab'.

"Fc" with regard to an antibody (e.g. of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), and complement dependent cytotoxicity (CDC), but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA,* 85:5879(1988)).

"Single-chain Fv-Fc antibody" or "scFv-Fc" refers to an engineered antibody consisting of a scFv connected to the Fc region of an antibody.

"Camelized single domain antibody", "heavy chain antibody", or "HCAb" refers to an antibody that contains two $V_H$ domains and no light chains (Riechmann L. and Muyldermans S., *J Immunol Methods*. December 10; 231(1-2): 25-38 (1999); Muyldermans S., *J Biotechnol*. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V K. et al. *Immunogenetics*. April; 54(1):39-47 (2002); Nguyen V K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J*. November; 21(13):3490-8. Epub 2007 Jun. 15 (2007)).

A "nanobody" refers to an antibody fragment that consists of a VHH domain from a heavy chain antibody and two constant domains, CH2 and CH3.

A "diabody" or "dAb" includes small antibody fragments with two antigen-binding sites, wherein the fragments comprise a $V_H$ domain connected to a VL domain in the same polypeptide chain ($V_H$-$V_L$ or $V_L$-$V_H$) (see, e.g. Holliger P. et al., *Proc Natl Acad Sci USA*. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "valent" as used herein refers to the presence of a specified number of antigen binding sites in a given molecule. The term "monovalent" refers to an antibody or an antigen-binding fragment having only one single antigen-binding site; and the term "multivalent" refers to an antibody or antigen-binding fragment having multiple antigen-binding sites. As such, the terms "bivalent", "tetravalent", and "hexavalent" denote the presence of two binding sites, four binding sites, and six binding sites, respectively, in an antigen-binding molecule. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

In certain embodiments, an "scFv dimer" is a bivalent diabody or bispecific scFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "dsFv" refers to a disulfide-stabilized Fv fragment that the linkage between the variable region of a single light chain and the variable region of a single heavy chain is a disulfide bond. In some embodiments, a "$(dsFv)_2$" or "(dsFv-dsFv')" comprises three peptide chains: two $V_H$ moieties linked by a peptide linker (e.g. a long flexible linker) and bound to two $V_L$ moieties, respectively, via disulfide bridges. In some embodiments, dsFv-dsFv' is bispecific in which each disulfide paired heavy and light chain has a different antigen specificity.

The term "chimeric" as used herein, means an antibody or antigen-binding fragment, having a portion of heavy and/or light chain derived from one species, and the rest of the heavy and/or light chain derived from a different species. In some embodiments, the non-human animal is a mammal, for example, a mouse, a rat, a rabbit, a goat, a sheep, a guinea pig, or a hamster.

The term "affinity" as used herein refers to the strength of non-covalent interaction between an immunoglobulin molecule (i.e. antibody) or fragment thereof and an antigen.

The term "specific binding" or "specifically binds" as used herein refers to a non-random binding reaction between two molecules, such as for example between an antibody and an antigen. Specific binding can be characterized in binding affinity, for example, represented by $K_D$ value, i.e., the ratio of dissociation rate to association rate ($k_{off}/k_{on}$) when the binding between the antigen and antigen-binding molecule reaches equilibrium. $K_D$ may be determined by using any conventional method known in the art, including but are not limited to surface plasmon resonance method, Octet method, microscale thermophoresis method, HPLC-MS method and FACS assay method. A $K_D$ value of $\leq 10^{-6}$ M (e.g. $\leq 5\times10^{-7}$ M, $\leq 2\times10^{-7}$ M, $\leq 10^{-7}$ M, $\leq 5\times10^{-8}$ M, $\leq 2\times10^{-8}$ M, $\leq 10^{-8}$ M, $\leq 5\times10^{-9}$ M, $\leq 4\times10^{-9}$M, $\leq 3\times10^{-9}$M, $\leq 2\times10^{-9}$ M) can indicate specific binding between an antibody or antigen binding fragments thereof and SARS-CoV-2 (e.g. SARS-CoV-2).

The term "epitope" as used herein refers to the specific group of atoms or amino acids on an antigen to which an antibody binds. Two antibodies may bind the same or a closely related epitope within an antigen if they exhibit competitive binding for the antigen. An epitope can be linear or conformational (i.e. including amino acid residues spaced apart). For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

The term "amino acid" as used herein refers to an organic compound containing amine ($-NH_2$) and carboxyl ($-COOH$) functional groups, along with a side chain specific to each amino acid. The names of amino acids are also represented as standard single letter or three-letter codes in the present disclosure, which are summarized as follows.

| Names | Three-letter Code | Single-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., *J. Mol. Biol.,* 215:403-410 (1990); Stephen F. et al., *Nucleic Acids Res.,* 25:3389-3402 (1997)), ClustalW2 (available on the website of European Bioinformatics Institute, see also, Higgins D. G. et al., *Methods in Enzymology,* 266:383-402 (1996); Larkin M. A. et al., *Bioinformatics* (Oxford, England), 23(21): 2947-8 (2007)), and ALIGN or Megalign (DNASTAR) software. A person skilled in the art may use the default parameters provided by the tool, or may customize the parameters as appropriate for the alignment, such as for example, by selecting a suitable algorithm.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or an antigen-binding fragment thereof" refers to the antibody or antigen-binding fragments thereof having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "subject" as used herein refers to human and non-human animal. Non-human animals include all vertebrates, e.g., mammals and non-mammals. A "subject" may also be a livestock animal (e.g., cow, swine, goat, chicken, rabbit or horse), or a rodent (e.g., rat or mouse), or a primate (e.g., gorilla or monkey), or a domestic animal (e.g., dog or cat). A "subject" may be a male or a female, and also may be at different ages. In certain embodiments, the subject is a human. A human "subject" may be Caucasian, African, Asian, Sumerian, or other races, or a hybrid of different races. A human "subject" may be elderly, adult, teenager, child or infant.

The term "prevent" or "preventing" as used herein includes slowing the onset of a disease, reducing the risk of developing a disease, suppressing or delaying the manifestation or development of symptoms associated with a disease, reducing the severity of a subsequent contraction or development of a disease, ameliorating a related symptom, and inducing immunity to protect against a disease.

The term "neutralizing" with respect to an antibody means that the antibody is capable of disrupting a formed viral particle or inhibiting formation of a viral particle or prevention of binding or infection of susceptible cells by a viral particle.

"Treating" or "treatment" of a disease, disorder or condition as used herein includes preventing or alleviating a disease, disorder or condition, slowing the onset or rate of development of a disease, disorder or condition, reducing the risk of developing a disease, disorder or condition, reducing or ending symptoms associated with a disease, disorder or condition, generating a complete or partial regression of a disease, disorder or condition, curing a disease, disorder or condition, or some combination thereof.

The "host cell" as used herein refers to a cell into which an exogenous polynucleotide and/or a vector has been introduced to express one or more exogenous proteins. It intends to refer to both the particular subject cell and the progeny thereof. A host cell can be a prokaryote, a eukaryote, a plant cell, an animal cell or a hybridoma. It can be a cell that does not express a protein at a desired level but comprises the nucleic acid, unless a regulatory agent is introduced into the cell or a regulatory sequence is introduced into the host cell so that it is operably linked with the nucleic acid.

The term "operably link" or "operably linked" refers to a juxtaposition, with or without a spacer or linker, of two or more biological sequences of interest in such a way that they are in a relationship permitting them to function in an intended manner. When used with respect to polypeptides, it is intended to mean that the polypeptide sequences are linked in such a way that permits the linked product to have the intended biological function. The term may also be used with respect to polynucleotides. For one instance, when a polynucleotide encoding a polypeptide is operably linked to a regulatory sequence (e.g., promoter, enhancer, silencer sequence, etc.), it is intended to mean that the polynucleotide sequences are linked in such a way that permits regulated expression of the polypeptide from the polynucleotide. In one embodiment, nucleotide sequences that are operably linked are contiguous (e.g., in the case of a signal sequences). Alternatively, nucleotide sequences that are operably linked can be non-contiguous (e.g., in the case of enhancers).

Neutralizing Antibodies Against SARS-CoV-2

In one aspect, the present disclosure provides a recombinant expression vectors that express anti-SARS-CoV-2 neutralizing antibodies or antigen-binding fragments thereof.

In certain embodiments, the neutralizing antibodies against SARS-CoV-2 and antigen-binding fragments thereof comprising one or more (e.g. 1, 2, 3, 4, 5, or 6) CDRs comprising the sequences selected from the group consisting of SYDIN (SEQ ID NO: 1), WMNPNSANPGYAQKFQG (SEQ ID NO: 2), ARVTIHYDILTGYYSNAFDI (SEQ ID NO: 3), RASQTISSYLN (SEQ ID NO: 4), AASSLQS (SEQ ID NO: 5), QQSYTTFMYT (SEQ ID NO: 6), SYAIS (SEQ ID NO: 11), GIIPIFGTTNYAQKFQG (SEQ ID NO: 12), RSAYGDKGYYFDY (SEQ ID NO: 13), RASQSVSNFLA (SEQ ID NO: 14), DASNRAT (SEQ ID NO: 15), QQRSNWPPQET (SEQ ID NO: 16), SYAIT (SEQ ID NO: 21), GIIPIFGTANFAQKFQG (SEQ ID NO: 22), LGGFADPFDY (SEQ ID NO: 23), RASQSVSNYLA (SEQ ID NO: 24), DAFNRAT (SEQ ID NO: 25), QQRSNWPPRIT (SEQ ID NO: 26).

Antibody "15A7" as used herein refers to a monoclonal antibody having a heavy chain variable region having the sequence of SEQ ID NO: 7, and a light chain variable region having the sequence of SEQ ID NO: 8. The heavy chain variable region is encoded by a nucleic acid sequence of SEQ ID NO: 9, and the light chain variable region is encoded by a nucleic acid sequence of SEQ ID NO: 10.

Antibody "31C2" as used herein refers to a monoclonal antibody having a heavy chain variable region having the sequence of SEQ ID NO: 17, and a light chain variable region having the sequence of SEQ ID NO: 18. The heavy chain variable region is encoded by a nucleic acid sequence of SEQ ID NO: 19, and the light chain variable region is encoded by a nucleic acid sequence of SEQ ID NO: 20.

Antibody "37G2" as used herein refers to a monoclonal antibody having a heavy chain variable region having the sequence of SEQ ID NO: 27, and a light chain variable region having the sequence of SEQ ID NO: 28. The heavy chain variable region is encoded by a nucleic acid sequence of SEQ ID NO: 29, and the light chain variable region is encoded by a nucleic acid sequence of SEQ ID NO: 30.

In certain embodiments, the present disclosure provides neutralizing antibodies against SARS-CoV-2 and antigen-binding fragments thereof comprising one or more (e.g. 1, 2, 3, 4, 5, or 6) CDR sequences of antibody 15A7, 31C2, or 37G2.

In certain embodiments, the present disclosure provides neutralizing antibodies against SARS-CoV-2 and antigen-binding fragments thereof comprising HCDR1 comprising an amino acid sequence selected from the group consisting of SEQ ID NOs: 1, 11 and 21, HCDR2 comprising an amino acid sequence selected from the group consisting of SEQ ID NOs: 2, 12 and 22, and HCDR3 comprising an amino acid sequence selected from the group consisting of SEQ ID NOs: 3, 13 and 23, and/or LCDR1 comprising an amino acid sequence selected from the group consisting of SEQ ID NOs: 4, 14 and 24, LCDR2 comprising an amino acid sequence selected from the group consisting of SEQ ID NOs: 5, 15 and 25, and LCDR3 comprising an amino acid sequence selected from the group consisting of 6, 16 and 26.

In certain embodiments, the present disclosure provides neutralizing antibodies against SARS-CoV-2 and antigen-binding fragments thereof comprising a HCDR1 comprising the sequence of SEQ ID NO: 1, a HCDR2 comprising the sequence of SEQ ID NO: 2, a HCDR3 comprising the sequence of SEQ ID NO: 3, and/or a LCDR1 comprising the sequence of SEQ ID NO: 4, a LCDR2 comprising the sequence of SEQ ID NO: 5, and a LCDR3 comprising the sequence of SEQ ID NO: 6. The HCDR1 is encoded by nucleic acid sequence of SEQ ID NO: 31, the HCDR2 is encoded by nucleic acid sequence of SEQ ID NO: 32, and the HCDR3 is encoded by nucleic acid sequence of SEQ ID NO: 33, the LCDR1 is encoded by nucleic acid sequence of SEQ ID NO: 34, the LCDR2 is encoded by nucleic acid sequence of SEQ ID NO: 35, and the LCDR3 is encoded by nucleic acid sequence of SEQ ID NO: 36.

In certain embodiments, the present disclosure provides neutralizing antibodies against SARS-CoV-2 and antigen-binding fragments thereof comprising a HCDR1 comprising the sequence of SEQ ID NO: 11, a HCDR2 comprising the sequence of SEQ ID NO: 12, a HCDR3 comprising the sequence of SEQ ID NO: 13, and/or a LCDR1 comprising the sequence of SEQ ID NO: 14, a LCDR2 comprising the sequence of SEQ ID NO: 15, and a LCDR3 comprising the sequence of SEQ ID NO: 16. The HCDR1 is encoded by nucleic acid sequence of SEQ ID NO: 39, the HCDR2 is encoded by nucleic acid sequence of SEQ ID NO: 40, and the HCDR3 is encoded by nucleic acid sequence of SEQ ID NO: 41, the LCDR1 is encoded by nucleic acid sequence of SEQ ID NO: 42, the LCDR2 is encoded by nucleic acid sequence of SEQ ID NO: 43, and the LCDR3 is encoded by nucleic acid sequence of SEQ ID NO: 44.

In certain embodiments, the present disclosure provides neutralizing antibodies against SARS-CoV-2 and antigen-binding fragments thereof comprising a HCDR1 comprising the sequence of SEQ ID NO: 21, a HCDR2 comprising the sequence of SEQ ID NO: 22, a HCDR3 comprising the sequence of SEQ ID NO: 23, and/or a LCDR1 comprising the sequence of SEQ ID NO: 24, a LCDR2 comprising the sequence of SEQ ID NO: 25, and a LCDR3 comprising the sequence of SEQ ID NO: 26. The HCDR1 is encoded by nucleic acid sequence of SEQ ID NO: 47, the HCDR2 is encoded by nucleic acid sequence of SEQ ID NO: 48, and the HCDR3 is encoded by nucleic acid sequence of SEQ ID NO: 49, the LCDR1 is encoded by nucleic acid sequence of SEQ ID NO: 50, the LCDR2 is encoded by nucleic acid sequence of SEQ ID NO: 51, and the LCDR3 is encoded by nucleic acid sequence of SEQ ID NO: 52.

Table 1 below shows the CDR amino acid sequences and nucleic acid encoding sequences of antibodies 15A7, 31C2 and 37G2. The CDR boundaries were defined or identified by the convention of Kabat. Table 2 below shows the heavy chain and light chain variable region amino acid sequences of antibodies 15A7, 31C2 and 37G2. Table 3 below shows the heavy chain and light chain variable region nucleic acid sequences of antibodies 15A7, 31C2 and 37G2.

TABLE 1

CDR amino acid sequences and nucleic acid sequences of 3 monoclonal antibodies.

| | CDR1 | CDR2 | CDR3 |
|---|---|---|---|
| 15A7 HCDR | SEQ ID NO: 1<br>SYDIN | SEQ ID NO: 2<br>WMNPNSANPGYAQKF<br>QG | SEQ ID NO: 3<br>ARVTIHYDILTGYYSNA<br>FDI |
| | SEQ ID NO: 31<br>AGTTATGATATCAAC | SEQ ID NO: 32<br>TGGATGAACCCTAACA<br>GTGCTAACCCAGGCTA<br>TGCACAGAAGTTCCAG<br>GGC | SEQ ID NO: 33<br>GCCCGAGTAACTATAC<br>ATTACGATATTTTGAC<br>TGGTTATTATTCGAAT<br>GCTTTTGATATC |
| LCDR | SEQ ID NO: 4<br>RASQTISSYLN | SEQ ID NO: 5<br>AASSLQS | SEQ ID NO: 6<br>QQSYTTFMYT |
| | SEQ ID NO: 34<br>CGGGCAAGTCA<br>GACCATTAGCA<br>GCTATTTAAAT | SEQ ID NO: 35<br>GCTGCATCCAGTTTGC<br>AAAGT | SEQ ID NO: 36<br>CAACAGAGTTACACTA<br>CCTTCATGTACACT |
| 31C2 HCDR | SEQ ID NO: 11<br>SYAIS | SEQ ID NO: 12<br>GIIPIFGTTNYAQKFQG | SEQ ID NO: 13<br>RSAYGDKGYYFDY |
| | SEQ ID NO: 39<br>AGCTATGCTAT<br>CAGC | SEQ ID NO: 40<br>GGGATCATCCCTATCT<br>TTGGTACAACAAACT<br>ACGCACAGAAGTTCC<br>AGGGC | SEQ ID NO: 41<br>CGTTCGGCCTACGGT<br>GATAAAGGGTACTAC<br>TTTGATTAC |

TABLE 1-continued

CDR amino acid sequences and nucleic acid sequences of 3 monoclonal antibodies.

| | | CDR1 | CDR2 | CDR3 |
|---|---|---|---|---|
| | LCDR | SEQ ID NO: 14<br>RASQSVSNFLA<br>SEQ ID NO: 42<br>AGGGCCAGTC<br>AGAGTGTTAG<br>CAACTTCTTAG<br>CC | SEQ ID NO: 15<br>DASNRAT<br>SEQ ID NO: 43<br>GATGCATCCAACAGG<br>GCCACT | SEQ ID NO: 16<br>QQRSNWPPQET<br>SEQ ID NO: 44<br>CAGCAGCGTAGCAAC<br>TGGCCTCCGCAAGAG<br>ACG |
| 37G2 | HCDR | SEQ ID NO: 21<br>SYAIT<br>SEQ ID NO: 47<br>AGCTATGCTAT<br>CACC | SEQ ID NO: 22<br>GIIPIFGTANFAQKFQG<br>SEQ ID NO: 48<br>GGGATCATCCCTATCT<br>TTGGTACAGCAAACT<br>TCGCACAGAAGTTCC<br>AGGGC | SEQ ID NO: 23<br>LGGFADPFDY<br>SEQ ID NO: 49<br>CTAGGGGGGTTCGCT<br>GACCCCTTTGACTAC |
| | LCDR | SEQ ID NO: 24<br>RASQSVSNYLA<br>SEQ ID NO: 50<br>AGGGCCAGTC<br>AGAGTGTTAG<br>CAACTACTTAG<br>CC | SEQ ID NO: 25<br>DAFNRAT<br>SEQ ID NO: 51<br>GATGCATTCAACAGG<br>GCCACT | SEQ ID NO: 26<br>QQRSNWPPRIT<br>SEQ ID NO: 52<br>CAGCAGCGTAGCAAC<br>TGGCCTCCGCGGATC<br>ACC |

TABLE 2

Variable region amino acid sequences of 3 monoclonal antibodies.

| | VH | VL |
|---|---|---|
| 15A7 | SEQ ID NO: 7<br>QVQLVQSGAEVKKPGASVKVSCKA<br>SGYTFTSYDINWVRQASGQGLEWM<br>GWMNPNSANPGYAQKFQGRVTMT<br>RNTSISTAFMELSSLRSDDTAVYYCA<br>RARVTIHYDILTGYYSNAFDIWGQG<br>TMVAVSS | SEQ ID NO: 8<br>DIQMTQSPSSLSASVGDRVTITCRA<br>SQTISSYLNWYQQKPGKAPKLLIY<br>AASSLQSGVPSRFSGSGSGADFTLT<br>ISSLQPEDFATYYCQQSYTTFMYTF<br>GQGTMLEIK |
| 31C2 | SEQ ID NO: 17<br>QVQLVQSGAEVKKPGSSVKVSCKA<br>SGGTFSSYAISWVRQAPGQGLEWM<br>GGI1PIFGTTNYAQKFQGRVTITADES<br>TSTAYMELNSLRSEDTAVYYCAGRS<br>AYGDKGYYFDYWGQGTLVTVSS | SEQ ID NO: 18<br>EIVLTQSPATLSLSPGERATLSCRAS<br>QSVSNFLAWYQQKPGQAPRLLIY<br>DASNRATGIPARFSGSGSGTDFTLT<br>ISSLQPEDFAVYYCQQRSNWPPQE<br>TFGQGTKVEIK |
| 37G2 | SEQ ID NO: 27<br>QVQLVQSGAEVKKPGSSVKVSCKA<br>SGGTFSSYAITWVRQAPGQGLEWM<br>GGIIPIFGTANFAQKFQGRVTITADES<br>TSTAYMELSSLRSEDTAVYYCAHLG<br>GFADPFDYWGQGTLVTVSS | SEQ ID NO: 28<br>EIVLTQSPATLSLSPGERATLSCRAS<br>QSVSNYLAWYQQKAGQAPRVLIY<br>DAFNRATGIPARFSGSGSGTDFTLT<br>ISSLEPEDFAVYYCQQRSNWPPRIT<br>FGQGTRLEIK |

TABLE 3

Variable region nucleic acid sequences of 3 monoclonal antibodies.

| | VH | VL |
|---|---|---|
| 15A7 | SEQ ID NO: 9<br>CAGGTGCAGcTGgTGcAGTcTGGGG<br>CTGAGGTGAAGAAGCCTGGGGCC<br>TCAGTGAAGGTCTCCTGCAAGGCT<br>TCTGGATACACCTTCACCAGTTATG<br>ATATCAACTGGGTGCGACAGGCCT<br>CTGGACAAGGGCTTGAGTGGATGG | SEQ ID NO: 10<br>GACATCCAGATGACCCAGTCTCCATC<br>CTCCCTGTCTGCATCTGTAGGAGACA<br>GAGTCACCATCACTTGCCGGGCAAGT<br>CAGACCATTAGCAGCTATTTAAATTGG<br>TATCAGCAGAAACCAGGGAAAGCCC<br>CTAAGCTCCTGATCTATGCTGCATCCA |

TABLE 3-continued

Variable region nucleic acid sequences of 3 monoclonal antibodies.

| | VH | VL |
|---|---|---|
| | GATGGATGAACCCTAACAGTGCTA ACCCAGGCTATGCACAGAAGTTCC AGGGCAGAGTCACCATGACCAGG AACACCTCCATaagCACAGCCTTCA TGGAGCTGAGCAGCCTGAGATCTG ACGACACGGCCGTGTATTACTGTG CGAGAGCCCGAGTAACTATACATT ACGATATTTTGACTggTTATTATTCG AATGCTTTTGATATCTGGGGCCAA GGGACAATGGTCGCCGTCTCTTCA | GTTTGCAAAGTGGGGTCCCATCAAGG TTCAGTGGCAGTGGATCTGGGGCAGA TTTCACTCTCACCATCAGCAGTCTGC AACCTGAAGATTTTGCAACTTACTAC TGTCAACAGAGTTACACTACCTTCAT GTACACTTTTGGCCAGGGGACCATGC TGGAGATCAAA |
| 31C2 | SEQ ID NO: 19 CAGGTGCAGCTGGTGCAGTCTGGG GCTGAGGTGAAGAAGCCTGGGTC GTCGGTGAAGGTCTCCTGCAAGGC TTCtGGAGGCACCTTCAGCAGCTAT GCTATCAGCTGGGTGCGACAGGCC CCTGGACAAGGGCTTGAGTGGATG GGAGGGATCATCCCTATCTTTGGTA CAACAAACTACGCACAGAAGTTCC AGGGCAGAGTCACGATTACCGCGG ACGAATCCACGAGCACAGCCTACA TGGAGCTGAACAGCCTGAGATCTG AGGACACGGCCGTGTATTACTGTG CGGGACGTTCGGCCTACGGTGATA AAGGGTACTACTTTGATTACTGGG GCCAGGGAACCCTGGTCACCGTCTCCTCA | SEQ ID NO: 20 GAAATTGTGTTGACACAGTCTCCAGC CACCCTGTCTTTGTCTCCAGGGGAAA GAGCCACCCTCTCCTGCAGGGCCAGT CAGAGTGTTAGCAACTTCTTAGCCTG GTATCAACAGAAACCTGGCCAGGCTC CCAGGCTCCTCATCTATGATGCATCCA ACAGGGCCACTGGCATCCCAGCCAG GTTCAGTGGCAGTGGGTCTGGGACA GACTTCACTCTCACCATCAGCAGCCT ACAGCCTGAAGATTTMCAGTTTATTA CTGTCAGCAGCGTAGCAACTGGCCTC CGCAAGAGACGTTCGGCCAAGGGAC CAAGGTGGAAATCAAA |
| 37G2 | SEQ ID NO: 29 CAGGTGCAGCTGGTGCAGTCTGGG GCTGAGGTGAAGAAGCCTGGGTC CTCGGTGAAGGTCTCCTGCAAGGC TTCTGGAGGCACCTTCAGCAGCTA TGCTATCACCTGGGTGCGACAGGC CCCTGGACAAGGGCTTGAGTGGAT GGGAGGGATCATCCCTATCTTTGGT ACAGCAAACTTCGCACAGAAGTTC CAGGGCAGAGTCACGATTACCGCG GACGAATCCACGAGCACAGCCTAC ATGGAGCTGAGCAGCCTGAGATCT GAGGACACGGCCGTGTATTACTGT GCCCACCTAGGGGGGTTCGCTGAC CCCTTTGACTACTGGGGCCAGGGA ACCCTGGTCACCGTCTCCTCA | SEQ ID NO: 30 GAAATTGTGTTGACACAGTCTCCAGC CACCCTGTCTTTGTCTCCAGGGGAAA GAGCCACCCTCTCCTGCAGGGCCAGT CAGAGTGTTAGCAACTACTTAGCCTG GTATCAACAGAAAGCTGGCCAGGCTC CCAGGGTCCTCATCTATGATGCATTCA ACAGGGCCACTGGCATCCCAGCCAG GTTCAGTGGCAGTGGGTCTGGGACA GACTTCACTCTCACCATCAGCAGCCT AGAGCCTGAAGATTTTGCAGTTTATTA CTGTCAGCAGCGTAGCAACTGGCCTC CGCGGATCACCTTCGGCCAAGGGACA CGACTGGAGATTAAA |

CDRs are known to be responsible for antigen binding. However, it has been found that not all of the 6 CDRs are indispensable or unchangeable. In other words, it is possible to replace or change or modify one or more CDRs in neutralizing antibodies 15A7, 31C2 and 37G2, yet substantially retain the specific binding affinity to SARS-CoV-2.

The antibodies and antigen-binding fragments thereof provided herein can comprise suitable framework region (FR) sequences from any species, such as mouse, human, rat, or rabbit, as long as the antibodies and antigen-binding fragments thereof can specifically bind to SARS-CoV-2. In certain embodiments, the CDR sequences provided in Table 1 above are obtained from human antibodies. In certain embodiments, the FR sequence is derived from human.

In some embodiments, the antibodies and antigen-binding fragments thereof provided herein comprise all or a portion of the heavy chain variable domain and/or all or a portion of the light chain variable domain. In one embodiment, the antibodies and antigen-binding fragments thereof provided herein is a single domain antibody which consists of all or a portion of the heavy chain variable domain provided herein. More information of such a single domain antibody is available in the art (see, e.g. U.S. Pat. No. 6,248,516).

In certain embodiments, the antibodies and antigen-binding fragments thereof provided herein further comprise an immunoglobulin (Ig) constant region, which optionally further comprises a heavy chain and/or a light chain constant region. In certain embodiments, the heavy chain constant region comprises CH1, hinge, and/or CH2-CH3 regions (or optionally CH2-CH3-CH4 regions). In certain embodiments, the antibodies and antigen-binding fragments thereof provided herein comprises heavy chain constant regions of human IgG1, IgG2, IgG3, IgG4, IgA1, IgA2 or IgM. In certain embodiments, the antibodies and antigen-binding fragments thereof provided herein comprises heavy chain constant regions of human IgG1. In certain embodiments, the antibodies and antigen-binding fragments thereof provided herein comprises heavy chain constant regions of human IgG4. In certain embodiments, the light chain constant region comprises $C_{kappa}$ (Cκ) or $C_{lambda}$ (Cλ). The constant region of the antibodies and antigen-binding fragments thereof provided herein may be identical to the wild-type constant region sequence or be different in one or more mutations. In certain embodiments, the heavy chain constant region is from human IgG1. In certain embodiments, the light chain constant region is from human lambda light chain.

In certain embodiments, the antibodies or the antigen-binding fragments thereof provided herein have different amino acid sequences compared with the antibody created by any animal (e.g., human). In certain embodiments, the antibodies or the antigen-binding fragments thereof provided herein have at least 1, 2, 3, 4, 5, 6, 7, 8, 9, 10, 12, 15, 20, 30, 40, 50, or 60 different amino acids compared with the antibody created by any animal (e.g., human). In certain embodiments, the antibodies or the antigen-binding fragments thereof provided herein have different amino acids in FR regions or Fc regions compared with the antibody created by any animal (e.g., human). In certain embodiments, the antibodies or the antigen-binding fragments thereof provided herein have six CDR sequences provided in Table 1 above and have different amino acids in FR regions or Fc regions compared with the antibody created by any animal (e.g., human).

In certain embodiments, the antibodies or the antigen-binding fragments thereof provided herein have a specific binding affinity to SARS-CoV-2 which is sufficient to provide for preventive and/or therapeutic use.

The antibodies or antigen-binding fragments thereof provided herein can be a monoclonal antibody, a polyclonal antibody, a humanized antibody, a chimeric antibody, a recombinant antibody, a bispecific antibody, a multi-specific antibody, a labeled antibody, a bivalent antibody, an anti-idiotypic antibody, or a fusion protein. A recombinant antibody is an antibody prepared in vitro using recombinant methods rather than in animals.

In one aspect, the present disclosure provides expression vectors that express a neutralizing antibody or antigen-binding fragment thereof, which competes for binding to SARS-CoV-2 with the antibody or antigen-binding fragment thereof provided herein. In certain embodiments, the present disclosure provides an expression vector that expresses a neutralizing antibody or antigen-binding fragment thereof, which competes for binding to SARS-CoV-2 with an antibody: a) comprising a heavy chain variable region comprising the sequence of SEQ ID NO: 7, and a light chain variable region comprising the sequence of any of SEQ ID NO: 8; b) comprising a heavy chain variable region comprising the sequence of SEQ ID NO: 17, and a light chain variable region comprising the sequence of any of SEQ ID NO: 18; or c) comprising a heavy chain variable region comprising the sequence of SEQ ID NO: 27, and a light chain variable region comprising the sequence of any of SEQ ID NO: 28.

Antibody Variants

The antibodies and antigen-binding fragments thereof provided herein also encompass various variants of the antibody sequences provided herein.

In certain embodiments, the antibody variants comprise one or more mutations in one or more of the CDR sequences provided in Table 1 above, one or more of the non-CDR sequences of the heavy chain variable region or light chain variable region provided in Table 2 above, and/or the constant region (e.g. Fc region). Such variants retain binding specificity to SARS-CoV-2 of their parent antibodies, but have one or more desirable properties conferred by the mutation(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation.

The parent antibody sequence may be screened to identify suitable or preferred residues to be modified or substituted, using methods known in the art, for example, "alanine scanning mutagenesis" (see, for example, Cunningham and Wells (1989) Science, 244:1081-1085). Briefly, target residues (e.g. charged residues such as Arg, Asp, His, Lys, and Glu) can be identified and replaced by a neutral or negatively charged amino acid (e.g. alanine or polyalanine), and the modified antibodies are produced and screened for the interested property. If substitution at a particular amino acid location demonstrates an interested functional change, then the position can be identified as a potential residue for mutation. The potential residues may be further assessed by substituting with a different type of residue (e.g. cysteine residue, positively charged residue, etc.).

Affinity Variants

Affinity variants of antibodies may contain mutations in one or more CDR sequences provided in Table 1 above, the heavy or light chain variable region sequences provided in Table 2, or one or more FR sequences which can be readily identified by a person skilled in the art based on the CDR sequences provided in Table 1 and the heavy or light chain variable region sequences provided in Table 2, as it is well-known in the art that a CDR region is flanked by two FR regions in the variable region. The affinity variants retain specific binding affinity to SARS-CoV-2 of the parent antibody, or even have improved SARS-CoV-2 specific binding affinity over the parent antibody. In certain embodiments, at least one (or all) of the substitution(s) in the CDR sequences, FR sequences, or variable region sequences comprises a conservative substitution.

A person skilled in the art will understand that in the CDR sequences provided in Table 1 above, and variable region sequences provided in Table 2 above, one or more amino acid residues may be substituted yet the resulting antibody or antigen-binding fragment still retain the binding affinity or binding capacity to SARS-CoV-2, or even have an improved binding affinity or capacity. Various methods known in the art can be used to achieve this purpose. For example, a library of antibody variants (such as Fab or scFv variants) can be generated and expressed with phage display technology, and then screened for the binding affinity to SARS-CoV-2. For another example, computer software can be used to virtually simulate the binding of the antibodies to SARS-CoV-2, and identify the amino acid residues on the antibodies which form the binding interface. Such residues may be either avoided in the substitution so as to prevent reduction in binding affinity, or targeted for substitution to provide for a stronger binding.

In certain embodiments, the antibodies and antigen-binding fragments thereof provided herein comprises one or more amino acid residue substitutions in one or more of the CDR sequences, and/or one or more of the FR sequences. In certain embodiments, an affinity variant comprises no more than 20, 15, 10, 9, 8, 7, 6, 5, 4, 3, 2, or 1 substitutions in the CDR sequences and/or FR sequences in total.

In certain embodiments, the antibodies and antigen-binding fragments thereof provided herein comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1 above yet retaining the specific binding to SARS-CoV-2 at a level similar to or even higher than its parent antibody.

In certain embodiments, the antibodies and antigen-binding fragments thereof provided herein comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2 above yet retaining the specific binding affinity to SARS-CoV-2 at a level similar to or even higher than its parent antibody. In some embodiments, the mutations occur in regions outside the CDRs (e.g. in the FRs).

Glycosylation Variants

The antibodies and antigen-binding fragments thereof provided herein also encompass glycosylation variants, which can be obtained to either increase or decrease the extent of glycosylation of the antibodies or antigen binding fragments thereof.

The antibodies or antigen binding fragments thereof may comprise one or more modifications that introduce or remove a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Cysteine-Engineered Variants

The antibodies and antigen-binding fragments thereof provided herein also encompass cysteine-engineered variants, which comprise one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisotope among others, at the site of the engineered cysteine, through for example a maleimide or haloacetyl. Methods for engineering antibodies or antigen-binding fragments thereof to introduce free cysteine residues are known in the art, see, for example, WO2006/034488.

Fc Variants

The antibodies and antigen-binding fragments thereof provided herein also encompass Fc variants, which comprise one or more amino acid residue mutations at the Fc region and/or hinge region, for example, to provide for altered effector functions such as ADCC and CDC. Methods of altering ADCC activity by antibody engineering have been described in the art, see for example, Shields R L. et al., *J Biol Chem.* 2001. 276(9): 6591-604; Idusogie E E. et al., *J Immunol.* 2000.164(8):4178-84; Steurer W. et al., *J Immunol.* 1995, 155(3): 1165-74; Idusogie E E. et al., *J Immunol.* 2001, 166(4): 2571-5; Lazar G A. et al., *PNAS,* 2006, 103(11): 4005-4010; Ryan M C. et al., *Mol. Cancer Ther.,* 2007, 6: 3009-3018; Richards J O. et al., *Mol Cancer Ther.* 2008, 7(8): 2517-27; Shields R. L. et al., *J. Biol. Chem,* 2002, 277: 26733-26740; Shinkawa T. et al., *J. Biol. Chem,* 2003, 278: 3466-3473.

CDC activity of the antibodies or antigen-binding fragments provided herein can also be altered, for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fe region variants.

One or more amino acids selected from amino acid residues 329, 331 and 322 of the Fc region can be replaced with a different amino acid residue to alter C1q binding and/or reduced or abolished complement dependent cytotoxicity (CDC) (see, U.S. Pat. No. 6,194,551 by Idusogie et al.). One or more amino acid substitution(s) can also be introduced to alter the ability of the antibody to fix complement (see PCT Publication WO 94/29351 by Bodmer et al.).

Also encompassed herein are antibodies and antigen-binding fragments thereof provided herein having Fc variants with one or more amino acid residue mutations at the Fc region and/or hinge region, to provide for reduced or eliminated antibody dependent enhancement (ADE) of SARS-CoV-2 infection. Such Fc variants may have reduced binding to Fc receptors (FcR). Examples of such mutations include, without limitation, mutations of leucine residues at positions 4, 5, or both of CH2 domain (e.g. to alanine, as LALA variant), see, for example, WO2010043977A2, which is incorporated herein to its entirety.

Antigen-Binding Fragments

Provided herein are also expression vectors that express neutralizing antigen-binding fragments against SARS-CoV-2. Various types of antigen-binding fragments are known in the art and can be developed based on the neutralizing antibodies against SARS-CoV-2 provided herein, including for example, the exemplary antibodies whose CDR are shown in Table 1 above, and variable sequences are shown in Table 2, and their different variants (such as affinity variants, glycosylation variants, Fc variants, cysteine-engineered variants and so on).

In certain embodiments, a neutralizing antigen-binding fragments against SARS-CoV-2 provided herein is a diabody, a Fab, a Fab', a $F(ab)_2$, a Fd, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

The expression vector comprising the polynucleotide comprising a nucleic acid sequence encoding an antigen-binding fragments (e.g. for Fab, Fv and ScFv antibody fragments) of the anti-SARS-COV-2 neutralizing antibody can be introduced into a host cells such as *E. coli* for expression.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

In certain embodiments, antibodies and antigen-binding fragments thereof provided herein are bivalent, tetravalent, hexavalent, or multivalent. Any molecule being more than bivalent is considered multivalent, encompassing for example, trivalent, tetravalent, hexavalent, and so on.

A bivalent molecule can be monospecific if the two binding sites are both specific for binding to the same antigen or the same epitope. This, in certain embodiments, provides for stronger binding to the antigen or the epitope than a monovalent counterpart. Similar, a multivalent molecule may also be monospecific. In certain embodiments, in a bivalent or multivalent antigen-binding moiety, the first valent of binding site and the second valent of binding site are structurally identical (i.e. having the same sequences), or structurally different (i.e. having different sequences albeit with the same specificity).

A bivalent can also be bispecific, if the two binding sites are specific for different antigens or epitopes. This also applies to a multivalent molecule. For example, a trivalent molecule can be bispecific when two binding sites are monospecific for a first antigen (or epitope) and the third binding site is specific for a second antigen (or epitope).

Recombinant Expression Vector

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. In one embodiment, the expression vector of the present disclosure comprises more than one origin of replication, thus not limiting the vector to one cell type. The term "origin of replication" refers to sequences which initiate replication when present in a vector. An origin of replication may be recognized by a replication initiation factor or, alternatively, by a DNA helicase. A vector may also include materials to aid in its entry into the cell, including but not limited to a viral particle, a liposome, or a protein coating.

A vector can be a recombinant expression vector or a cloning vector. The present disclosure provides vectors (e.g., expression vectors) containing the nucleic acid sequence provided herein encoding the anti-SARS-COV-2 neutralizing antibody, at least one promoter operably linked to the nucleic acid sequence, and/or at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid such as pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

A "recombinant expression vector" is a nucleic acid molecule encoding a gene that is expressed in a host cell, and, furthermore, contains the necessary elements to control expression of the gene. Typically, an expression vector comprises a transcription promoter, a gene of interest, and a transcription terminator.

In certain embodiments, the recombinant expression vector is viral-based vector. In certain embodiments, the recombinant expression vector is a lentivirus vector. In certain embodiments, the recombinant expression vector is an adeno-associated virus (AAV) vector.

In certain embodiments, the nucleic acid sequence encoding an anti-SARS-COV-2 neutralizing antibody or antigen-binding fragments thereof provided herein is codon optimized. The term "codon optimized" or "optimized codon" or "codon optimization" as used herein refers to modifying a nucleic acid sequence for enhanced expression in the cells of the vertebrate of interest, e.g. human, by replacing at least one, more than one, or a significant number, of codons of the native sequence with codons that are more frequently or most frequently used in the genes of that vertebrate, but the modification of the nucleic acid sequence does not alter the amino acid sequence of the original translated protein. Various species exhibit particular bias for certain codons of a particular amino acid.

In certain embodiments, the nucleic acid sequence encoding the anti-SARS-COV-2 neutralizing antibody is codon optimized. In certain embodiments, the nucleic acid sequence encoding the heavy chain variable region of the anti-SARS-COV-2 neutralizing antibody is codon optimized. In certain embodiments, the nucleic acid sequence encoding the light chain variable region of the anti-SARS-COV-2 neutralizing antibody is codon optimized. In certain embodiments, the nucleic acid sequence encoding the heavy chain constant region of the anti-SARS-COV-2 neutralizing antibody is codon optimized. In certain embodiments, the nucleic acid sequence encoding the light chain constant region of the anti-SARS-COV-2 neutralizing antibody is codon optimized.

Regulatory Elements

The recombinant expression vector disclosed herein can include regulatory elements that are necessary for transcription and translation of the gene of interest (as well as the selectable marker), into proteins. The transcriptional regulatory elements can comprise transcriptional initiation and termination sites, and polyadenylation signal sequence, including promoters, enhancers, introns, self-cleaving 2A peptide sequences, woodchuck hepatitis virus post-transcriptional regulatory elements (WPREs) and/or polyadenylation (polyA) signal sequences.

The term "promoter" as used herein refers to a polynucleotide sequence that can control transcription of an encoding sequence. The promoter sequence includes specific sequences that are sufficient for RNA polymerase recognition, binding and transcription initiation. In addition, the promoter sequence may include sequences that modulate this recognition, binding and transcription initiation activity of RNA polymerases. The promoter may affect the transcription of a gene located on the same nucleic acid molecule as itself or a gene located on a different nucleic acid molecule as itself. Functions of the promoter sequences, depending upon the nature of the regulation, may be constitutive or inducible by a stimulus. A "constitutive" promoter as used herein refers to a promoter that functions to continually activate gene expression in host cells. An "inducible" promoter as used herein refers to a promoter that activates gene expression in host cells in the presence of certain stimulus or stimuli.

In certain embodiments, the promoters of the present disclosure are eukaryotic promoters such as the promoters from CMV (e.g., the CMV immediate early promoter (CMV promoter)), epstein barr virus (EBV) promoter, human immunodeficiency virus (HIV) promoter (e.g., the HIV long terminal repeat (LTR) promoter), moloney virus promoter, mouse mammary tumor virus (MMTV) promoter, rous sarcoma virus (RSV) promoter, SV40 early promoter, promoters from human genes such as human myosin promoter, human hemoglobin promoter, human muscle creatine promoter, human metalothionein beta-actin promoter, human ubiquitin C promoter (UBC), mouse phosphoglycerate kinase 1 promoter (PGK), human thymidine kinase promoter (TK), human elongation factor 1 alpha promoter (EF1A), cauliflower mosaic virus (CaMV) 35S promoter, E2F-1 promoter (promoter of E2F1 transcription factor 1), promoter of alpha-fetoprotein, promoter of cholecystokinin, promoter of carcinoembryonic antigen, promoter of C-erbB2/neu oncogene, promoter of cyclooxygenase, promoter of CXC-Chemokine receptor 4 (CXCR4), promoter of human epididymis protein 4 (HE4), promoter of hexokinase type II, promoter of L-plastin, promoter of mucin-like glycoprotein (MUC1), promoter of prostate specific antigen (PSA), promoter of survivin, promoter of tyrosinase related protein (TRP1), and promoter of tyrosinase.

In certain embodiments, the promoter used in the present disclosure is muscle specific, for example, cytomegalovirus immediate early promoter (CMV), chimeric chicken-β-actin (CAG), and ubiquitin C (UBC) promoters. In certain embodiments, the promoter is a synthetic CASI promoter consists of the cytomegalovirus immediate early promoter (CMV) followed by a fragment of chicken-β-actin (CAG) promoter containing the transcription initiation site. This fusion is immediately followed by a synthetically designed intron that utilizes consensus splice donor and splice acceptor sequences flanking the enhancer region of the human ubiquitin C (UBC) promoters.

In certain embodiments, the CASI promoter has a sequence of SEQ ID NO: 55:

```
ggagttccgcgttacataacttacggtaaatggcccgcctggctgaccgc

ccaacgacccccgcccattgacgtcaataatgacgtatgttcccatagta

acgccaatagggactttccattgacgtcaatgggtggagtatttacggta

aactgcccacttggcagtacatcaagtgtatcatatgccaagtacgcccc

ctattgacgtcaatgacggtaaatggcccgcctggcattatgcccagtac

atgaccttatgggactttcctacttggcagtacatctacgtattagtcat

cgctattaccatggtcgaggtgagccccacgttctgcttcactctcccca

tctcccccccctccccacccccaattagtatttatttattattaattatt

agtgcagcgatgggggcggggggggggggggggcgcgcgccaggcggggcg

gggcggggcgaggggcggggcggggcgaggcggagaggtgcggcggcagc

caatcagagcggcgcgctccgaaagtttccttttatggcgaggcggcggc

ggcggcggccctataaaaagcgaagcgcgcggcgggcgggagtcgctgcg

cgctgccttcgccccgtgccccgctccgccgccgcctcgcgccgcccgcc

ccggctctgactgaccgcgttactaaaacaggtaagtccggcctccgcgc

cgggttttggcgcctcccgcgggcgcccccctcctcacggcgagcgctgc

cacgtcagacgaagggcgcagcgagcgtcctgatccttccgcccggacgc

tcaggacagcggcccgctgctcataagactcggccttagaaccccagtat

cagcagaaggacattttaggacgggacttgggtgactctagggcactggt

tttctttccagagagcggaacaggcgaggaaaagtagtcccttctcggcg

attctgcggagggatctccgtggggcggtgaacgccgatgatgcctctac

taaccatgttcatgttttcttttttttttctacaggtcctgggtgacgaac

ag.
```

In certain embodiments, the CASI promoter is located at 5' end of the nucleic acid sequence encoding the anti-SARS-COV-2 neutralizing antibody.

The recombinant expression vector may also comprises enhancers. Promoters and enhancers have the same general function of activating transcription in the cell. They are often overlapping and contiguous, often seeming to have a very similar modular organization. The basic distinction between enhancers and promoters is operational. An enhancer region as a whole must be able to stimulate transcription at a distance, while a promoter must have one or more elements that direct initiation of RNA synthesis at a particular site and in a particular orientation, whereas enhancers lack these specificities.

The term "transcriptional initiation site" refers to the nucleic acid in the construct corresponding to the first nucleic acid incorporated into the primary transcript, i.e., the mRNA precursor; the transcriptional initiation site may overlap with the promoter sequences.

The term "transcriptional termination site" refers to a nucleotide sequence normally located at the 3' end of a gene of interest or the stretch of sequences to be transcribed, that causes RNA polymerase to terminate transcription. In certain embodiments, the transcriptional termination site is located downstream of the posttranscriptional regulatory element. Transcription termination site include, but are not limited to, polyadenylation signal sequences. Polyadenylation signal sequence, or poly-A addition signal provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence includes the sequence AATAAA located at about 10-30 nucleotides upstream from the site of cleavage, plus a downstream sequence. For the purpose of muscle-derived expression, polyA sequence can be derived from, as non-limiting examples, the Simian virus 40(SV40) polyA, the rabbit beta-globin (RBG) polyA and the bovine growth hormone (BGH) polyA. In certain embodiments, the polyA sequence is a SV40 polyA.

In certain embodiments, the SV40 polyA has a nucleic acid sequence of SEQ ID NO: 60:

```
aacttgtttattgcagcttataatggtacaaataaagcaatagcatcac

aaatttcacaaataaagcatttttttcactgcattctagttgtggtttgt

ccaaactcatcaatgtatcttatcatgtctggatc.
```

Posttranscriptional regulatory elements can be further included in the expression vector to enhance transgene expression. In certain embodiments, the posttranscriptional regulatory element is a viral posttranscriptional regulatory element, such as posttranscriptional regulatory element of the hepatitis B virus (HPRE), RNA transport element (RTE) and woodchuck hepatitis virus posttranscriptional regulatory element (WPRE). The WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. This regulatory element is positioned within the vector so as to be included in the RNA transcript of the transgene, but outside of stop codon of the transgene translational unit.

In certain embodiments, the WPRE has a nucleic acid sequence of SEQ ID NO: 59:

```
aatcaacctctggattacaaaatttgtgaaagattgactggtattctta
actatgttgctccttttacgctatgtggatacgctgctttaatgcctttt
gtatcatgctattgcttcccgtatggctttcattttctcctccttgtat
aaatcctggttgctgtctctttatgaggagttgtggcccgttgtcaggc
aacgtggcgtggtgtgcactgtgtttgctgacgcaacccccactggttg
gggcattgccaccacctgtcagctcctttccgggactttcgctttcccc
ctccctattgccacggcggaactcatcgccgcctgccttgcccgctgct
ggacaggggctcggctgttgggcactgacaattccgtggtgttgtcggg
gaaatcatcgtcctttccttggctgctcgcctgtgttgccacctggatt
ctgcgcgggacgtccttctgctacgtcccttcggccctcaatccagcgg
accttccttcccgcggcctgctgccggctctgcggcctcttccgcgtct
tcgccttcgccctcagacgagtcggatctccctagggccgcctccccgc.
```

Polynucleotides Encoding the Antibodies and Recombinant Methods

The present disclosure provides a recombinant expression vector comprising an expression cassette comprising a nucleic acid sequence encoding an anti-SARS-COV-2 neutralizing antibody or antigen-binding fragments thereof.

The term "polynucleotide" or "nucleic acid" as used herein refers to ribonucleic acids (RNA), deoxyribonucleic acids (DNA), or mixed ribonucleic acids-deoxyribonucleic acids such as DNA-RNA hybrids. The polynucleotide or nucleic acid may be single stranded or double stranded DNA or RNA or DNA-RNA hybrids. The polynucleotide or nucleic acid may be linear or circular. In certain embodiments, wherein the first and the second heterologous polynucleotide are both DNA when the virus is a DNA virus, or the first and the second heterologous polynucleotide are both RNA when the virus is a RNA virus. In certain embodiment, the first heterologous polynucleotide and the second heterologous polynucleotide are both double stranded DNA. The polynucleotides of the present disclosure are double stranded DNA and the nucleic acid sequences are represented with the encoding sequences, such as those shown by SEQ ID NOs: 9, 10, 19, 20, 29-36, 38-44, and 46-63.

The nucleic acid sequence may be introduced into the recombinant expression vector using conventional methods known in the art, for example by synthesis by polymerase chain reaction (PCR) and ligation with the viral genome having compatible restriction ends. For more details, see, for example, Sambrook et al. Molecular Cloning: A Laboratory Manual (Cold Spring Harbor Laboratory, N.Y. (1989)), which is incorporated herein by reference in its entirety.

In certain embodiments, the nucleic acid sequence encoding the anti-SARS-COV-2 neutralizing antibody or antigen-binding fragments thereof provided herein is introduced in the place of a multiple cloning site (MCS) of a recombinant expression vector.

In certain embodiments, the expression cassette inserted into the recombinant expression vector comprises nucleic acid sequences encoding the heavy chain variable region and the light chain variable region of the anti-SARS-COV-2 neutralizing antibody provided herein. In certain embodiments, the polynucleotide inserted into the recombinant expression vector comprises nucleic acid sequences encoding the heavy chain variable region and light chain variable region of the anti-SARS-COV-2 neutralizing antibody provided herein, wherein the nucleic acid sequence encoding the heavy chain variable region is operably linked to the nucleic acid sequence encoding the heavy chain constant region, and the nucleic acid sequence encoding the light chain variable region is operably linked to the nucleic acid sequence encoding the light chain constant region.

In certain embodiments, the heavy chain constant region is from human IgG1. In certain embodiments, the heavy chain constant region comprises amino acid sequence of SEQ ID NO: 37. In certain embodiments, the heavy chain constant region is encoded by nucleic acid sequence of SEQ ID NO: 38.

Amino acid sequence of human IgG1 constant region comprises SEQ ID NO: 37:

```
STKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTV
DKSRWQQGNVFSCSVMHEALHNHYTQKSLSLSPGK.
```

Nucleic acid sequence encoding human IgG1 constant region comprises SEQ ID NO: 38:

```
agcaccaagggcccatcggtcttccccctggcaccctcctccaagagca
cctctgggggcacagcggccctgggctgcctggtcaaggactacttccc
cgaaccggtgacggtgtcgtggaactcaggcgccctgaccagcggcgtg
cacaccttcccggctgtcctacagtcctcaggactctactccctcagca
gcgtggtgaccgtgccctccagcagcttgggcacccagacctacatctg
caacgtgaatcacaagcccagcaacaccaaggtggacaagaaagttgag
cccaaatcttgtgacaaaactcacacatgcccaccgtgcccagcacctg
aactcctggggggaccgtcagtcttcctcttccccccaaaacccaagga
caccctcatgatctcccggacccctgaggtcacatgcgtggtggtggac
gtgagccacgaagaccctgaggtcaagttcaactggtacgtggacggcg
tggaggtgcataatgccaagacaaagccgcgggaggagcagtacaacag
cacgtaccgtgtggtcagcgtcctcaccgtcctgcaccaggactggctg
aatggcaaggagtacaagtgcaaggTctccaacaaagccctcccagccc
ccatcgagaaaaccatctccaaagccaaagggcagccccgagaaccaca
ggtgtacaccctgcccccatcccgggaggagatgaccaagaaccaggtc
agcctgacctgcctggtcaaaggcttctatcccagcgacatcgccgtgg
agtgggagagcaatgggcagccggagaacaactacaagaccacgcctcc
cgtgctggactccgacggctccttcttcctctacagcaagctcaccgtg
gacaagagcaggtggcagcaggggaacgtcttctcatgctccgtgatgc
atgaggctctgcacaaccactacacgcagaagagcctctccctgtctcc
gggtaaa.
```

In certain embodiments, the light chain constant region is from human lambda light chain. In certain embodiments, the light chain constant region comprises amino acid sequence of SEQ ID NO: 45. In certain embodiments, the light chain constant region is encoded by nucleic acid sequence of SEQ ID NO: 46.

Amino acid sequence of human lambda light chain constant region comprises SEQ ID NO: 45:

```
GQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEK

TVAPTECS.
```

Nucleic acid sequence encoding human lambda light chain constant region comprises SEQ ID NO: 46:

```
ggtcagcccaaggctgccccctcggtcactctgttcccgccctcctctg

aggagcttcaagccaacaaggccacactggtgtgtctcataagtgactt

ctacccgggagccgtgacagtggcctggaaggcagatagcagccccgtc

aaggcgggagtggagaccaccacaccctccaaacaaagcaacaacaagt

acgcggccagcagctatctgagcctgacgcctgagcagtggaagtccca

cagaagctacagctgccaggtcacgcatgaagggagcaccgtggagaag

acagtggcccctacagaatgttcatag.
```

In certain embodiments, a first signal peptide is operably linked to the anti-SARS-COV-2 neutralizing antibody VH at the N-terminal of the VH. In certain embodiments, a second signal peptide is operably linked to the anti-SARS-COV-2 neutralizing antibody VL at the N-terminal of the VL.

A "signal peptide" as used herein refers to a short peptide sequence, typically less than 50 amino acids long, which directs the transport of the protein in which it is incorporated. Signal peptides typically are linked to a protein at the N terminus and coding sequences encoding the signal peptide often include the initiation codon that encodes the N terminal methionine. Signal peptides target the protein for transport within the cell and are involved in the secretory pathway in which the presence of the signal peptide on a protein targets the protein for transport though the secretory pathway such that the protein is secreted by the cell or otherwise targeted for release by the cell into the extracellular environment.

In certain embodiments, the first signal peptide is encoded by a nucleic acid sequence of SEQ ID NO: 56. In certain embodiments, the second signal peptide is encoded by a nucleic acid sequence of SEQ ID NO: 58.

Nucleic acid sequence of the first signal peptide comprises SEQ ID NO: 56:

```
atggcgacgggttcaagaacttccctacttcttgcatttggcctgctt

tgtttgccgtggttacaggagggctcggca
```

Nucleic acid sequence encoding the second signal peptide comprises SEQ ID NO: 58:

```
atggcaacagggagccgaacctctctgctccttgctttcgggctcctt

tgcctaccgtggctccaagagggctcggca.
```

In certain embodiments, the heavy chain variable region and light chain variable region of the anti-SARS-COV-2 neutralizing antibody provided herein are expressed separately. In other words, they are not expressed as a fusion protein, and are not connected with each other either (whether covalently or through a linker).

In certain embodiments, the expression of the heavy chain variable region and light chain variable region of the anti-SARS-COV-2 neutralizing antibody provided herein are driven by one promoter, and the heavy chain variable region and light chain variable region are linked via a self-cleaving 2A peptide sequence.

As used herein, the term "self-cleaving 2A peptide" refers to relatively short peptides of the order of 20 amino acids long, depending on the virus of origin. They were originally thought to mediate the autocatalytic proteolysis of the large polyprotein, but are now understood to act co-translationally, by preventing the formation of a normal peptide bond between the glycine and last proline, resulting in the ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. The 2A peptide was identified among Picornaviruses but in a different sub-group, the Aphthoviruses, a typical example of which is the Foot-and-mouth disease virus. In certain embodiments, the self-cleaving 2A peptide is selected from the group consisting of F2A (Foot-and-mouth disease virus 18), E2A (Equine rhinitis A virus), T2A (Thosea asigna virus) and P2A (Porcine teschovirus-1).

In certain embodiments, the self-cleaving 2A peptide is a F2A. In certain embodiments, the self-cleaving 2A peptide sequence is encoded by a nucleic acid sequence of:

```
                                                  (SEQ ID NO: 57)
cgaaaaagaagatcaggttcgggtgcgccagtaaagcagacattaaact

ttgatttgctgaaacttgcaggtgatgtagagtcaaatccaggtcca.
```

In certain embodiments, the nucleic acid sequence encoding the anti-SARS-COV-2 neutralizing antibody comprises encoding sequences of the first signal peptide-the anti-SARS-COV-2 neutralizing antibody heavy chain variable region-a human IgG1 constant region-self-cleaving 2A peptide-the second signal peptide-the anti-SARS-COV-2 neutralizing antibody light chain variable region-a human lambda light chain constant region in an orientation from 5' to 3' of the sense strand.

Method for Producing Recombinant Vector

Vectors comprising the polynucleotide sequence encoding the antibody can be introduced to a host cell for cloning or gene expression. Suitable host cells for cloning or expressing the DNA in the vectors herein are the prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces.*

In addition to prokaryotes, eukaryotic microbes such as filamentous fungi or yeast are suitable cloning or expression hosts for expressing anti-SARS-COV-2 neutralizing antibody. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), K *bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruifly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is 293 cell.

Host cells are transformed with the above-described expression or cloning vectors for anti-SARS-COV-2 neutralizing antibody production and cultured in conventional nutrient media modified as appropriate for inducing promoters, selecting transformants, or amplifying the genes encoding the desired sequences. In another embodiment, the antibody polypeptides may be produced by homologous recombination known in the art.

The host cells used to produce the antibody provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Production of Adeno-Associated Virus (AAV) Vector

In certain embodiments, the recombinant expression vector is a recombinant AAV vector.

Adeno-associated viruses (AAVs) is a satellite virus of adenovirus, containing a linear single-stranded DNA (ssDNA) molecule of approximately 48,000 bases, replication-defective and nonenveloped, belongs to the family Parvoviridae. The transgene expression requires the conversion of ssDNA to double-stranded (ds) genome.

A method of producing the recombinant expression AAV virus provided herein comprises providing a packaging cell line with a AAV vector comprising 5' AAV inverted terminal repeat (ITR) and 3' AAV ITR, helper functions for generating a productive AAV infection, and AAV cap genes, wherein the AAV vector comprises a nucleotide sequence encoding the anti-SARS-COV-2 neutralizing antibody; and recovering the recombinant AAV virus from the supernatant of the packaging cell line.

The terms "inverted terminal repeats", "terminal repeats", "ITRs", and "TRs" refer to those sequences present at both termini of the native single-stranded AAV genome, required in cis for replication, virus packaging, integration, and/or pro-virus rescue of the AAV virus including any fragments or derivatives of an ITR which retain activity of a full-length or wild type ITR. The ITRs can be from any AAV serotypes, for example, serotypes 1, 2, 3, 4, 5, 6, 7, 8, 9, 10 or 11, or from non-AAV sequence, such as those of canine parvovirus, mouse parvovirus, human parvovirus B-19, or the SV40 hairpin that serves as the origin of SV40 replication, which can further be modified by truncation, substitution, deletion, insertion and/or addition. The ITR can also be synthesized.

In certain embodiments, the ITRs are from AAV serotype 2 (i.e. AAV2). In certain embodiments, the ITR has a nucleic acid sequence of SEQ ID NO: 53 or 54.

In certain embodiments, the 5' ITR has a nucleic acid sequence of SEQ ID NO: 53:

```
ctgcgcgctcgctcgctcactgaggccgcccgggcaaagcccgggcgt
cgggcgacctttggtcgcccggcctcagtgagcgagcgagcgcgcaga
gagggagtggccaactccatcactaggggttcct.
```

In certain embodiments, the 3' ITR has a nucleic acid sequence of SEQ ID NO: 54:

```
aggaacccctagtgatggagttggccactccctctctgcgcgctcgctc
gctcactgaggccgggcgaccaaaggtcgcccgacgcccgggctttgcc
cgggcggcctcagtgagcgagcgagcgcgc.
```

AAV is a helper-dependent virus, and requires co-infection with a helper virus such as adenovirus (Ad) or cotransfection of helper virus DNA for a productive infection (See Ward and Berns, J. Virol., 70:4495, 1996). The term "helper functions" or "helpers" as used herein refers to an activity that is required for replication and/or packaging of an AAV but is not encoded within that AAV. Helper function can be provided by a host cell that is expressing suitable helper functions or by, for example, a helper virus.

In certain embodiments, the helper functions are provided by one or more helper plasmids or helper viruses comprising adenoviral helper genes. Helper viruses of AAV are known in the art and the non-limiting examples include, viruses from adenoviruses, herpesviruses or poxviruses such as vaccinia. Examples of herpesviruses include, but are not limited to, herpes simplex viruses (HSV), Epstein-Barr viruses (EBV), cytomegaloviruses (CMV) and pseudorabies viruses (PRV). Helper plasmids include pHELP (Applied Viromics). A skilled artisan will appreciate that any helper virus or helper plasmid of AAV that can provide adequate helper function to AAV can be used herein.

AAV helper expresses rep and cap gene products. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

The term "Rep gene" is a gene encoding a replication protein having at least one functional activity of a native AAV Rep protein (e.g., Rep 40, 52, 68, 78). The rep proteins facilitate replication of DNA through recognition, binding and nicking of the AAV origin of DNA replication as well as DNA helicase activity. Additional functions of the rep protein include modulation of transcription from AAV (or other heterologous) promoters and site-specific integration of AAV DNA into a host chromosome. "Cap gene" is a gene encoding a capsid protein having at least one functional activity of a native AAV Cap protein (e.g., VP1, VP2, VP3). Cap proteins have the ability to induce formation of a capsid, facilitate accumulation of single-stranded DNA, facilitate AAV DNA packaging into capsids (i.e., encapsidation), bind to cellular receptors, and facilitate entry of the virus into host cells.

In certain embodiments, the AAV cap genes can be present in a plasmid. The plasmid can further comprise an AAV rep gene. The cap genes and/or rep gene may be derived from any AAV serotype (including, but not limited to, AAV1, AAV2, AAV4, AAV5, AAV6, AAV7, AAV8, AAV9, and any variants thereof), which can be used herein to produce the recombinant expression AAV vector disclosed herein to express one or more proteins of interest. In certain embodiments, the AAV cap genes is selected from a capsid of serotype 1, serotype 2, serotype 4, serotype 5, serotype 6, serotype 7, serotype 8, serotype 9, or any variant thereof. In certain embodiments, the AAV cap gene is derived from a capsid of serotype 6 and the rep gene is derived from AAV2.

In certain embodiments, the recombinant AAV (rAAV) vector comprises a mutated capsid protein encapsidating a rAAV vector genome, wherein the mutated capsid protein comprises amino acid substitutions at amino acids 129, 445, and 731 of the AAV6 capsid protein sequence. In certain embodiments, the mutated capsid protein has amino acid substitutions Phe129Leu (F129L), Tyr445Phe (Y445F) and Tyr731Phe (Y731F), wherein the mutated capsid protein is mutated AAV6 capsid protein. In certain embodiments, the mutated capsid protein has greater transduction of muscle, airway, liver, central nervous system, retina or lung cells compared to wild-type AAV. The mutated capsid protein is described in detail in US20190216949, which is incorporated herein in its entirety.

In certain embodiments, the AAV vector is pseudotyped. The term "pseudotyped" is meant a nucleic acid or genome derived from a first AAV serotype that is encapsidated or packaged by an AAV capsid containing at least one AAV Cap protein of a second serotype (i.e., one different from the first AAV serotype). In certain embodiments, serotype 2 Rep proteins are preferred. Construction and use of AAV vectors and AAV proteins of different serotypes are discussed in Chao et al., Mol. Ther. 2:619-623, 2000; Davidson et al., PNAS 97:3428-3432, 2000; Xiao et al., J. Virol. 72:2224-2232, 1998; Halbert et al., J. Virol. 74:1524-1532, 2000; Halbert et al., J. Virol. 75:6615-6624, 2001; and Auricchio et al., Hum. Molec. Genet. 10:3075-3081, 2001.

In some embodiments, the packaging cell line can be transfected with a helper plasmid or helper virus, the AAV vector and a plasmid encoding the AAV cap and/or rep genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

The recombinant AAV viruses disclosed herein can also be produced using any convention methods known in the art suitable for producing infectious recombinant AAV. For example, a recombinant AAV can be produced by using a cell line that stably expresses some of the necessary components for AAV particle production. For example, a plasmid (or multiple plasmids) comprising AAV rep and cap genes, and a selectable marker (e.g. a neomycin resistance gene), can be integrated into the genome of a packaging cell line. The packaging cell line can then be co-infected with a helper virus providing the helper functions (e.g., adenovirus) and the AAV vector provided herein comprising the 5' and 3' AAV ITRs and the nucleotide sequence encoding the protein(s) of interest. In another example, adenovirus or baculovirus rather than plasmids can be used to introduce rep and cap genes into the packaging cells. In yet another example, both the AAV vector containing the 5' and 3' AAV ITRs and the rep-cap genes can be stably integrated into the DNA of packaging cells, and the helper functions can be provided by a wild-type adenovirus to produce the recombinant AAV.

In certain embodiments, the expression cassette provided herein comprises in an orientation from 5' to 3' of the sense strand: a 5' AAV inverted terminal repeat (ITR)1-a promoter-the nucleic acid sequence encoding the anti-SARS-COV-2 neutralizing antibody-WPRE-a polyA signal sequence-a 3' AAV ITR2.

In certain embodiments, the recombinant AAV vector that express 15A7 antibody comprises a genomic nucleic acid sequence of SEQ ID NO: 61:

CAGCAGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCA

GAGAGGGAGTGGCCAACTCCATCACTAGGGGTTCCTTGTAGTTAATGATT

AACCCGCCATGCTACTTATCTACGTAGCCATGCTCTAGGACATTGATTATT

GACTAGTggagttccgcgttacataacttacggtaaatggcccgcctggctgaccgcccaacgacccccgcccatt gacgtcaataatgacgtatgttcccatagtaacgccaatagggactttccattgacgtcaatgggtggagtatttacggtaaac tgcccacttggcagtacatcaagtgtatcatatgccaagtacgccccctattgacgtcaatgacggtaaatggcccgcctgg cattatgcccagtacatgaccttatgggactttcctacttggcagtacatctacgtattagtcatcgctattaccatggtcgaggt gagccccacgttctgcttcactctccccatctcccccccctccccacccccaattagtatttatttattaattattagtgcag cgatgggggcggggggggggggggcgcgcgccaggcggggcggggcggggcgaggggcggggcggggcga ggcggagaggtgcggcggcagccaatcagagcggcgcgctccgaaagtttccttttatggcgaggcggcggcggcgg cggccctataaaaagcgaagcgcgcggcgggcgggagtcgctgcgcgctgccttcgccccgtgccccgctccgccgc cgcctcgcgccgcccgccccggctctgactgaccgcgttactaaaacaggtaagtccggcctccgcgccgggttttggcg cctcccgcgggcgccccctcctcacggcgagcgctgccacgtcagacgaagggcgcagcgagcgtcctgatccttcc gcccggacgctcaggacagcggcccgctgctcataagactcggccttagaaccccagtatcagcagaaggacattttagg acgggacttgggtgactctagggcactggttactttccagagagcggaacaggcgaggaaaagtagtcccttctcggcga ttctgcggagggatctccgtggggcggtgaacgccgatgatgcctctactaaccatgttcatgattc111111111ctacaggtc ctgggtgacgaacagGGTACCGCCACCatggcgacgggttcaagaacttccctacttcttgcatttggcctgcttt gtttgccgtggttacaggagggctcggcaCAGGTGCAGcTGgTGcAGTcTGGGGCTGAGGTG

AAGAAGCCTGGGGCCTCAGTGAAGGTCTCCTGCAAGGCTTCTGGATACAC

CTTCACCAGTTATGATATCAACTGGGTGCGACAGGCCTCTGGACAAGGGC

TTGAGTGGATGGGATGGATGAACCCTAACAGTGCTAACCCAGGCTATGCA

CAGAAGTTCCAGGGCAGAGTCACCATGACCAGGAACACCTCCATaagCACA

GCCTTCATGGAGCTGAGCAGCCTGAGATCTGACGACACGGCCGTGTATTA

CTGTGCGAGAGCCCGAGTAACTATACATTACGATATTTTGACTggTTATTAT

TCGAATGCTTTTGATATCTGGGGCCAAGGGACAATGGTCGCCGTCTCTTCA

AGCACCAAGGGCCCATCGGTCTTCCCCCTGGCACCCTCCTCCAAGAGCAC

CTCTGGGGGCACAGCGGCCCTGGGCTGCCTGGTCAAGGACTACTTCCCCG

AACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGT

GAATCACAAGCCCAGCAACACCAAGGTGGACAAGAAAGTTGAGCCCAAA

TCTTGTGACAAAACTCACACATGCCCACCGTGCCCAGCACCTGAACTCCT

GGGGGGACCGTCAGTCTTCCTCTTCCCCCCAAAACCCAAGGACACCCTCA

TGATCTCCCGGACCCCTGAGGTCACATGCGTGGTGGTGGACGTGAGCCAC

GAAGACCCTGAGGTCAAGTTCAACTGGTACGTGGACGGCGTGGAGGTGCA

TAATGCCAAGACAAAGCCGCGGGAGGAGCAGTACAACAGCACGTACCGT

-continued

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAAGGGCAGCCCCGAGAACCACAGGTGTACACCCTG

CCCCCATCCCGGGAGGAGATGACCAAGAACCAGGTCAGCCTGACCTGCCT

GGTCAAAGGCTTCTATCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACC

ACTACACGCAGAAGAGCCTCTCCCTGTCTCCGGGTAAAcgaaaaagaagatcaggttc gggtgcgccagtaaagcagacattaaactttgatttgctgaaacttgcaggtgatgtagagtcaaatccaggtccaatggca acagggagccgaacctctctgctccttgctttcgggctcctagcctaccgtggctccaagagggctcggcagacatccag atgacccagtctccatcCtCCCTGTCTGCATCTGTAGGAGACAGAGTCACCATCACTT

GCCGGGCAAGTCAGACCATTAGCAGCTATTTAAATTGGTATCAGCAGAAA

CCAGGGAAAGCCCCTAAGCTCCTGATCTATGCTGCATCCAGTTTGCAAAG

TGGGGTCCCATCAAGGTTCAGTGGCAGTGGATCTGGGGCAGATTTCACTC

TCACCATCAGCAGTCTGCAACCTGAAGATTTTGCAACTTACTACTGTCAAC

AGAGTTACACTACCTTCATGTACACTTTTGGCCAGGGGACCATGCTGGAG

ATCAAAGGTCAGCCCAAGGCTGCCCCCTCGGTCACTCTGTTCCCGCCCTCC

TCTGAGGAGCTTCAAGCCAACAAGGCCACACTGGTGTGTCTCATAAGTGA

CTTCTACCCGGGAGCCGTGACAGTGGCCTGGAAGGCAGATAGCAGCCCCG

TCAAGGCGGGAGTGGAGACCACCACACCCTCCAAACAAAGCAACAACAA

GTACGCGGCCAGCAGCTATCTGAGCCTGACGCCTGAGCAGTGGAAGTCCC

ACAGAAGCTACAGCTGCCAGGTCACGCATGAAGGGAGCACCGTGGAGAA

GACAGTGGCCCCTACAGAATGTTCATAGCtctagaggAtaatcaacctctggattacaaaatttg tgaaagattgactggtattcttaactatgttgctccttttacgctatgtggatacgctgctttaatgcctttgtatcatgctattgcttc ccgtatggctttcattttctcctccttgtataaatcctggttgctgtctctttatgaggagttgtggcccgttgtcaggcaacgtgg cgtggtgtgcactgtgtttgctgacgcaacccccactggttggggcattgccaccacctgtcagctcctttccgggactttcg ctttccccctccctattgccacggcggaactcatcgccgcctgccttgcccgctgctggacaggggctcggctgttgggca ctgacaattccgtggtgttgtcggggaaatcatcgtcctttccttggctgctcgcctgtgttgccacctggattctgcgcggga cgtccttctgctacgtcccttcggccctcaatccagcggaccttccttcccgcggcctgctgccggctctgcggcctcttccg cgtcttcgccttcgccctcagacgagtcggatctccctttgggccgcctccccgcctAAGCTTATCGATACCG

TCGAGATCTAACTTGTTTATTGCAGCTTATAATGGTTACAAATAAAGCAAT

AGCATCACAAATTTCACAAATAAAGCATTTTTTTCACTGCATTCTAGTTGT

GGTTTGTCCAAACTCATCAATGTATCTTATCATGTCTGGATCTCGACCTCG

ACTAGAGCATGGCTACGTAGATAAGTAGCATGGCGGGTTAATCATTAACT

ACAAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGC

CCGGGCGGCCTCAGTGAGCGAGCGAGCGCGCCAGCTGGCGTAATAGCGA

AGAGGCCCGCACCGATCGCCCTTCCCAACAGTTGCGCAGCCTGAATGGCG

AATGGAATTCCAGACGATTGAGCGTCAAAATGTAGGTATTTCCATGAGCG

-continued

TTTTTCCTGTTGCAATGGCTGGCGGTAATATTGTTCTGGATATTACCAGCA

AGGCCGATAGTTTGAGTTCTTCTACTCAGGCAAGTGATGTTATTACTAATC

AAAGAAGTATTGCGACAACGGTTAATTTGCGTGATGGACAGACTCTTTTA

CTCGGTGGCCTCACTGATTATAAAAACACTTCTCAGGATTCTGGCGTACCG

TTCCTGTCTAAAATCCCTTTAATCGGCCTCCTGTTTAGCTCCCGCTCTGATT

CTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCG

TGACCGCTACACTTGCCAGCGCCCTAGCGCCCGCTCCTTTCGCTTTCTTCC

CTTCCTTTCTCGCCACGTTCGCCGGCTTTCCCCGTCAAGCTCTAAATCGGG

GGCTCCCTTTAGGGTTCCGATTTAGTGCTTTACGGCACCTCGACCCCAAAA

AACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGT

TCCAAACTGGAACAACACTCAACCCTATCTCGGTCTATTCTTTTGATTTAT

AAGGGATTTTGCCGATTTCGGCCTATTGGTTAAAAAATGAGCTGATTTAAC

AAAAATTTAACGCGAATTTTAACAAAATATTAACGTTTACAATTTAAATAT

TTGCTTATACAATCTTCCTGTTTTTGGGGCTTTTCTGATTATCAACCGGGGT

ACATATGATTGACATGCTAGTTTTACGATTACCGTTCATCGATTCTCTTGTT

TGCTCCAGACTCTCAGGCAATGACCTGATAGCCTTTGTAGAGACCTCTCAA

AAATAGCTACCCTCTCCGGCATGAATTTATCAGCTAGAACGGTTGAATAT

CATATTGATGGTGATTTGACTGTCTCCGGCCTTTCTCACCCGTTTGAATCTT

TACCTACACATTACTCAGGCATTGCATTTAAAATATATGAGGGTTCTAAAA

ATTTTTATCCTTGCGTTGAAATAAAGGCTTCTCCCGCAAAAGTATTACAGG

GTCATAATGTTTTTGGTACAACCGATTTAGCTTTATGCTCTGAGGCTTTATT

GCTTAATTTTGCTAATTCTTTGCCTTGCCTGTATGATTTATTGGATGTTGGA

ATTCCTGATGCGGTATTTTCTCCTTACGCATCTGTGCGGTATTTCACACCG

CATATGGTGCACTCTCAGTACAATCTGCTCTGATGCCGCATAGTTAAGCCA

GCCCCGACACCCGCCAACACCCGCTGACGCGCCCTGACGGGCTTGTCTGC

TCCCGGCATCCGCTTACAGACAAGCTGTGACCGTCTCCGGGAGCTGCATG

TGTCAGAGGTTTTCACCGTCATCACCGAAACGCGCGAGACGAAAGGGCCT

CGTGATACGCCTATTTTTATAGGTTAATGTCATGATAATAATGGTTTCTTA

GACGTCAGGTGGCACTTTTCGGGGAAATGTGCGCGGAACCCCTATTTGTTT

ATTTTTCTAAATACATTCAAATATGTATCCGCTCATGAGACAATAACCCTG

ATAAATGCTTCAATAATATTGAAAAAGGAAGAGTATGAGTATTCAACATT

TCCGTGTCGCCCTTATTCCCTTTTTTGCGGCATTTTGCCTTCCTGTTTTTGCT

CACCCAGAAACGCTGGTGAAAGTAAAAGATGCTGAAGATCAGTTGGGTG

CACGAGTGGGTTACATCGAACTGGATCTCAACAGCGGTAAGATCCTTGAG

AGTTTTCGCCCCGAAGAACGTTTTCCAATGATGAGCACTTTTAAAGTTCTG

CTATGTGGCGCGGTATTATCCCGTATTGACGCCGGGCAAGAGCAACTCGG

TCGCCGCATACACTATTCTCAGAATGACTTGGTTGAGTACTCACCAGTCAC

AGAAAAGCATCTTACGGATGGCATGACAGTAAGAGAATTATGCAGTGCTG

CCATAACCATGAGTGATAACACTGCGGCCAACTTACTTCTGACAACGATC

-continued

GGAGGACCGAAGGAGCTAACCGCTTTTTTGCACAACATGGGGGATCATGT

AACTCGCCTTGATCGTTGGGAACCGGAGCTGAATGAAGCCATACCAAACG

ACGAGCGTGACACCACGATGCCTGTAGCAATGGCAACAACGTTGCGCAAA

CTATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGAC

AGATCGCTGAGATAGGTGCCTCACTGATTAAGCATTGGTAACTGTCAGAC

CAAGTTTACTCATATATACTTTAGATTGATTTAAAACTTCATTTTTAATTTA

AAAGGATCTAGGTGAAGATCCTTTTTGATAATCTCATGACCAAAATCCCTT

AACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACA

AAAAAACCACCGCTACCAGCGGTGGTTTGTTTGCCGGATCAAGAGCTACC

AACTCTTTTTCCGAAGGTAACTGGCTTCAGCAGAGCGCAGATACCAAATA

CTGTCCTTCTAGTGTAGCCGTAGTTAGGCCACCACTTCAAGAACTCTGTAG

CACCGCCTACATACCTCGCTCTGCTAATCCTGTTACCAGTGGCTGCTGCCA

GTGGCGATAAGTCGTGTCTTACCGGGTTGGACTCAAGACGATAGTTACCG

GATAAGGCGCAGCGGTCGGGCTGAACGGGGGGTTCGTGCACACAGCCCA

GCTTGGAGCGAACGACCTACACCGAACTGAGATACCTACAGCGTGAGCTA

TGAGAAAGCGCCACGCTTCCCGAAGGGAGAAAGGCGGACAGGTATCCGG

TAAGCGGCAGGGTCGGAACAGGAGAGCGCACGAGGGAGCTTCCAGGGGG

AAACGCCTGGTATCTTTATAGTCCTGTCGGGTTTCGCCACCTCTGACTTGA

GCGTCGATTTTTGTGATGCTCGTCAGGGGGGCGGAGCCTATGGAAAAACG

CCAGCAACGCGGCCTTTTTACGGTTCCTGGCCTTTTGCTGGCCTTTTGCTC

ACATGTTCTTTCCTGCGTTATCCCCTGATTCTGTGGATAACCGTATTACCG

CCTTTGAGTGAGCTGATACCGCTCGCCGCAGCCGAACGACCGAGCGCAGC

GAGTCAGTGAGCGAGGAAGCGGAAGAGCGCCCAATACGCAAACCGCCTC

TCCCCGCGCGTTGGCCGATTCATTAATG.

In certain embodiments, the recombinant AAV vector that express 31C2 antibody comprises a genomic nucleic acid sequence of SEQ ID NO: 62:

CAGCAGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCA

GAGAGGGAGTGGCCAACTCCATCACTAGGGGTTCCTTGTAGTTAATGATT

AACCCGCCATGCTACTTATCTACGTAGCCATGCTCTAGGACATTGATTATT

GACTAGTggagttccgcgttacataacttacggtaaatggcccgcctggctgaccgcccaacgacccccgcccatt gacgtcaataatgacgtatgttcccatagtaacgccaatagggactttccattgacgtcaatgggtggagtatttacggtaaac tgcccacttggcagtacatcaagtgtatcatatgccaagtacgccccctattgacgtcaatgacggtaaatggcccgcctgg cattatgcccagtacatgaccttatgggactttcctacttggcagtacatctacgtattagtcatcgctattaccatggtcgaggt -continued gagccccacgttctgcttcactctccccatctcccccccctccccacccccaattagtatttatttattattaattattagtgcag cgatgggggcgggggggggggggggcgcgcgccaggcggggcggggcggggcgaggggcggggcggggcga ggcggagaggtgcggcggcagccaatcagagcggcgcgctccgaaagtttccttttatggcgaggcggcggcggcgg cggccctataaaaagcgaagcgcgcggcgggcgggagtcgctgcgcgctgccttcgccccgtgccccgctccgccgc cgcctcgcgccgcccgccccggctctgactgaccgcgttactaaaacaggtaagtccggcctccgcgccgggttttggcg cctcccgcgggcgcccccctcctcacggcgagcgctgccacgtcagacgaagggcgcagcgagcgtcctgatccttcc gcccggacgctcaggacagcggcccgctgctcataagactcggccttagaaccccagtatcagcagaaggacattttagg acgggacttgggtgactctagggcactggttactttccagagagcggaacaggcgaggaaaagtagtcccttctcggcga ttctgcggagggatctccgtggggcggtgaacgccgatgatgcctctactaaccatgttcatgattattattactacaggtc ctgggtgacgaacagGGTACCGCCACCatggcgacgggttcaagaacttccctacttcttgcatttggcctgcttt gffTgccgtggttacaggagggctcggcaCAGGTGCAGCTGGTGCAGTCTGGGGCTGAGGT GAAGAAGCCTGGGTCGTCGGTGAAGGTCTCCTGCAAGGCTTCtGGAGGCA

CCTTCAGCAGCTATGCTATCAGCTGGGTGCGACAGGCCCCTGGACAAGGG

CTTGAGTGGATGGGAGGGATCATCCCTATCTTTGGTACAACAAACTACGC

ACAGAAGTTCCAGGGCAGAGTCACGATTACCGCGGACGAATCCACGAGC

ACAGCCTACATGGAGCTGAACAGCCTGAGATCTGAGGACACGGCCGTGTA

TTACTGTGCGGGACGTTCGGCCTACGGTGATAAAGGGTACTACTTTGATTA

CTGGGGCCAGGGAACCCTGGTCACCGTCTCCTCAAGCACCAAGGGCCCAT

CGGTCTTCCCCCTGGCACCCTCCTCCAAGAGCACCTCTGGGGGCACAGCG

GCCCTGGGCTGCCTGGTCAAGGACTACTTCCCCGAACCGGTGACGGTGTC

GTGGAACTCAGGCGCCCTGACCAGCGGCGTGCACACCTTCCCGGCTGTCC

TACAGTCCTCAGGACTCTACTCCCTCAGCAGCGTGGTGACCGTGCCCTCCA

GCAGCTTGGGCACCCAGACCTACATCTGCAACGTGAATCACAAGCCCAGC

AACACCAAGGTGGACAAGAAAGTTGAGCCCAAATCTTGTGACAAAACTC

ACACATGCCCACCGTGCCCAGCACCTGAACTCCTGGGGGGACCGTCAGTC

TTCCTCTTCCCCCCAAAACCCAAGGACACCCTCATGATCTCCCGGACCCCT

GAGGTCACATGCGTGGTGGTGGACGTGAGCCACGAAGACCCTGAGGTCA

AGTTCAACTGGTACGTGGACGGCGTGGAGGTGCATAATGCCAAGACAAA

GCCGCGGGAGGAGCAGTACAACAGCACGTACCGTGTGGTCAGCGTCCTCA

CCGTCCTGCACCAGGACTGGCTGAATGGCAAGGAGTACAAGTGCAAGGTC

TCCAACAAAGCCCTCCCAGCCCCCATCGAGAAAACCATCTCCAAAGCCAA

AGGGCAGCCCCGAGAACCACAGGTGTACACCCTGCCCCCATCCCGGGAGG

AGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACA

ACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAAcgaaaaagaagatcaggttcgggtgcgccagtaaagcagacatt aaactttgatttgctgaaacttgcaggtgatgtagagtcaaatccaggtccaatggcaacagggagccgaacctctctgctc cttgcMcgggctcctttgcctaccgtggctccaagagggctcggcagaaattgtgttgacacagtctccagccaccCTG

TCTTTGTCTCCAGGGGAAAGAGCCACCCTCTCCTGCAGGGCCAGTCAGAG

TGTTAGCAACTTCTTAGCCTGGTATCAACAGAAACCTGGCCAGGCTCCCA

GGCTCCTCATCTATGATGCATCCAACAGGGCCACTGGCATCCCAGCCAGG

TTCAGTGGCAGTGGGTCTGGGACAGACTTCACTCTCACCATCAGCAGCCT

ACAGCCTGAAGATTTTGCAGTTTATTACTGTCAGCAGCGTAGCAACTGGC

CTCCGCAAGAGACGTTCGGCCAAGGGACCAAGGTGGAAATCAAAGGTCA

GCCCAAGGCTGCCCCCTCGGTCACTCTGTTCCCGCCCTCCTCTGAGGAGCT

TCAAGCCAACAAGGCCACACTGGTGTGTCTCATAAGTGACTTCTACCCGG

GAGCCGTGACAGTGGCCTGGAAGGCAGATAGCAGCCCCGTCAAGGCGGG

AGTGGAGACCACCACACCCTCCAAACAAAGCAACAACAAGTACGCGGCC

AGCAGCTATCTGAGCCTGACGCCTGAGCAGTGGAAGTCCCACAGAAGCTA

CAGCTGCCAGGTCACGCATGAAGGGAGCACCGTGGAGAAGACAGTGGCC

CCTACAGAATGTTCATAGCtctagaggAtaatcaacctctggattacaaaatttgtgaaagattgactggt attcttaactatgttgctccttttacgctatgtggatacgctgctttaatgcctttgtatcatgctattgcttcccgtatggctttcattt tctcctccttgtataaatcctggttgctgtctctttatgaggagttgtggcccgttgtcaggcaacgtggcgtggtgtgcactgt gtttgctgacgcaacccccactggttggggcattgccaccacctgtcagctcctttccgggactttcgctttccccctccctatt gccacggcggaactcatcgccgcctgccttgcccgctgctggacaggggctcggctgttgggcactgacaattccgtggt gttgtcggggaaatcatcgtcctttccttggctgctcgcctgtgttgccacctggattctgcgcgggacgtccttctgctacgtc ccttcggccctcaatccagcggaccttccttcccgcggcctgctgccggctctgcggcctcttccgcgtcttcgccttcgccc tcagacgagtcggatctccctttgggccgcctccccgcctAAGCTTATCGATACCGTCGAGATCTA

ACTTGTTTATTGCAGCTTATAATGGTTACAAATAAAGCAATAGCATCACAA

ATTTCACAAATAAAGCATTTTTTTCACTGCATTCTAGTTGTGGTTTGTCCAA

ACTCATCAATGTATCTTATCATGTCTGGATCTCGACCTCGACTAGAGCATG

GCTACGTAGATAAGTAGCATGGCGGGTTAATCATTAACTACAAGGAACCC

CTAGTGATGGAGTTGGCCACTCCCTCTCTGCGCGCTCGCTCGCTCACTGAG

GCCGGGCGACCAAAGGTCGCCCGACGCCCGGGCTTTGCCCGGGCGGCCTC

AGTGAGCGAGCGAGCGCGCCAGCTGGCGTAATAGCGAAGAGGCCCGCAC

CGATCGCCCTTCCCAACAGTTGCGCAGCCTGAATGGCGAATGGAATTCCA

GACGATTGAGCGTCAAAATGTAGGTATTTCCATGAGCGTTTTTCCTGTTGC

AATGGCTGGCGGTAATATTGTTCTGGATATTACCAGCAAGGCCGATAGTTT

GAGTTCTTCTACTCAGGCAAGTGATGTTATTACTAATCAAAGAAGTATTGC

GACAACGGTTAATTTGCGTGATGGACAGACTCTTTTACTCGGTGGCCTCAC

TGATTATAAAAACACTTCTCAGGATTCTGGCGTACCGTTCCTGTCTAAAAT

CCCTTTAATCGGCCTCCTGTTTAGCTCCCGCTCTGATTCTAACGAGGAAAG

CACGTTATACGTGCTCGTCAAAGCAACCATAGTACGCGCCCTGTAGCGGC

GCATTAAGCGCGGCGGGTGTGGTGGTTACGCGCAGCGTGACCGCTACACT

TGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGG

TTCCGATTTAGTGCTTTACGGCACCTCGACCCCAAAAAACTTGATTAGGGT

GATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACA

-continued

ACACTCAACCCTATCTCGGTCTATTCTTTTGATTTATAAGGGATTTTGCCG

ATTTCGGCCTATTGGTTAAAAAATGAGCTGATTTAACAAAAATTTAACGC

GAATTTTAACAAAATATTAACGTTTACAATTTAAATATTTGCTTATACAAT

CTTCCTGTTTTTGGGGCTTTTCTGATTATCAACCGGGGTACATATGATTGA

CATGCTAGTTTTACGATTACCGTTCATCGATTCTCTTGTTTGCTCCAGACTC

TCAGGCAATGACCTGATAGCCTTTGTAGAGACCTCTCAAAAATAGCTACC

CTCTCCGGCATGAATTTATCAGCTAGAACGGTTGAATATCATATTGATGGT

GATTTGACTGTCTCCGGCCTTTCTCACCCGTTTGAATCTTTACCTACACATT

ACTCAGGCATTGCATTTAAAATATATGAGGGTTCTAAAAATTTTTATCCTT

GCGTTGAAATAAAGGCTTCTCCCGCAAAAGTATTACAGGGTCATAATGTT

TTTGGTACAACCGATTTAGCTTTATGCTCTGAGGCTTTATTGCTTAATTTTG

CTAATTCTTTGCCTTGCCTGTATGATTTATTGGATGTTGGAATTCCTGATGC

GGTATTTTCTCCTTACGCATCTGTGCGGTATTTCACACCGCATATGGTGCA

CTCTCAGTACAATCTGCTCTGATGCCGCATAGTTAAGCCAGCCCCGACACC

CGCCAACACCCGCTGACGCGCCCTGACGGGCTTGTCTGCTCCCGGCATCC

GCTTACAGACAAGCTGTGACCGTCTCCGGGAGCTGCATGTGTCAGAGGTT

TTCACCGTCATCACCGAAACGCGCGAGACGAAAGGGCCTCGTGATACGCC

TATTTTTATAGGTTAATGTCATGATAATAATGGTTTCTTAGACGTCAGGTG

GCACTTTTCGGGGAAATGTGCGCGGAACCCCTATTTGTTTATTTTTCTAAA

TACATTCAAATATGTATCCGCTCATGAGACAATAACCCTGATAAATGCTTC

AATAATATTGAAAAAGGAAGAGTATGAGTATTCAACATTTCCGTGTCGCC

CTTATTCCCTTTTTTGCGGCATTTTGCCTTCCTGTTTTTGCTCACCCAGAAA

CGCTGGTGAAAGTAAAAGATGCTGAAGATCAGTTGGGTGCACGAGTGGGT

TACATCGAACTGGATCTCAACAGCGGTAAGATCCTTGAGAGTTTTCGCCC

CGAAGAACGTTTTCCAATGATGAGCACTTTTAAAGTTCTGCTATGTGGCGC

GGTATTATCCCGTATTGACGCCGGGCAAGAGCAACTCGGTCGCCGCATAC

ACTATTCTCAGAATGACTTGGTTGAGTACTCACCAGTCACAGAAAAGCAT

CTTACGGATGGCATGACAGTAAGAGAATTATGCAGTGCTGCCATAACCAT

GAGTGATAACACTGCGGCCAACTTACTTCTGACAACGATCGGAGGACCGA

AGGAGCTAACCGCTTTTTTGCACAACATGGGGGATCATGTAACTCGCCTT

GATCGTTGGGAACCGGAGCTGAATGAAGCCATACCAAACGACGAGCGTG

ACACCACGATGCCTGTAGCAATGGCAACAACGTTGCGCAAACTATTAACT

GGCGAACTACTTACTCTAGCTTCCCGGCAACAATTAATAGACTGGATGGA

GGCGGATAAAGTTGCAGGACCACTTCTGCGCTCGGCCCTTCCGGCTGGCT

GGTTTATTGCTGATAAATCTGGAGCCGGTGAGCGTGGGTCTCGCGGTATC

ATTGCAGCACTGGGGCCAGATGGTAAGCCCTCCCGTATCGTAGTTATCTA

CACGACGGGGAGTCAGGCAACTATGGATGAACGAAATAGACAGATCGCT

GAGATAGGTGCCTCACTGATTAAGCATTGGTAACTGTCAGACCAAGTTTA

CTCATATATACTTTAGATTGATTTAAAACTTCATTTTTAATTTAAAAGGAT

CTAGGTGAAGATCCTTTTTGATAATCTCATGACCAAAATCCCTTAACGTGA

-continued

GTTTTCGTTCCACTGAGCGTCAGACCCCGTAGAAAAGATCAAAGGATCTT

CTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTT

TTCCGAAGGTAACTGGCTTCAGCAGAGCGCAGATACCAAATACTGTCCTT

CTAGTGTAGCCGTAGTTAGGCCACCACTTCAAGAACTCTGTAGCACCGCC

TACATACCTCGCTCTGCTAATCCTGTTACCAGTGGCTGCTGCCAGTGGCGA

TAAGTCGTGTCTTACCGGGTTGGACTCAAGACGATAGTTACCGGATAAGG

CGCAGCGGTCGGGCTGAACGGGGGGTTCGTGCACACAGCCCAGCTTGGAG

CGAACGACCTACACCGAACTGAGATACCTACAGCGTGAGCTATGAGAAA

GCGCCACGCTTCCCGAAGGGAGAAAGGCGGACAGGTATCCGGTAAGCGG

CAGGGTCGGAACAGGAGAGCGCACGAGGGAGCTTCCAGGGGGAAACGCC

TGGTATCTTTATAGTCCTGTCGGGTTTCGCCACCTCTGACTTGAGCGTCGA

TTTTTGTGATGCTCGTCAGGGGGGCGGAGCCTATGGAAAAACGCCAGCAA

CGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGT

GAGCTGATACCGCTCGCCGCAGCCGAACGACCGAGCGCAGCGAGTCAGT

GAGCGAGGAAGCGGAAGAGCGCCCAATACGCAAACCGCCTCTCCCCGCG

CGTTGGCCGATTCATTAATG.

In certain embodiments, the recombinant AAV vector that express 37G2 antibody comprises a genomic nucleic acid sequence of SEQ ID NO: 63:

CAGCAGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCA

GAGAGGGAGTGGCCAACTCCATCACTAGGGGTTCCTTGTAGTTAATGATT

AACCCGCCATGCTACTTATCTACGTAGCCATGCTCTAGGACATTGATTATT

GACTAGTggagttccgcgttacataacttacggtaaatggcccgcctggctgaccgcccaacgacccccgcccatt gacgtcaataatgacgtatgttcccatagtaacgccaatagggactttccattgacgtcaatgggtggagtatttacggtaaac tgcccacttggcagtacatcaagtgtatcatatgccaagtacgccccctattgacgtcaatgacggtaaatggcccgcctgg cattatgcccagtacatgaccttatgggactttcctacttggcagtacatctacgtattagtcatcgctattaccatggtcgaggt gagccccacgttctgcttcactctccccatctcccccccctccccacccccaattagtatttatttattattaattattagtgcag cgatgggggcgggggggggggggggcgcgcgccaggcggggcggggcggggcgaggggcggggcggggcga ggcggagaggtgcggcggcagccaatcagagcggcgcgctccgaaagtttccttttatggcgaggcggcggcggcgg cggccctataaaaagcgaagcgcgcggcgggcgggagtcgctgcgcgctgccttcgccccgtgccccgctccgccgc cgcctcgcgccgcccgccccggctctgactgaccgcgttactaaaacaggtaagtccggcctccgcgccgggttttggcg cctcccgcgggcgccccctcctcacggcgagcgctgccacgtcagacgaagggcgcagcgagcgtcctgatccttcc gcccggacgctcaggacagcggcccgctgctcataagactcggccttagaaccccagtatcagcagaaggacattttagg acgggacttgggtgactctagggcactggttactttccagagagcggaacaggcgaggaaaagtagtcccttctcggcga ttctgcggagggatctccgtggggcggtgaacgccgatgatgcctctactaaccatgttcatgttttctattattctacaggtc ctgggtgacgaacagGGTACCGCCACCatggcgacgggttcaagaacttccctacttcttgcatttggcctgcttt gtttgccgtggttacaggagggctcggcacAGGTGCAGCTGGTGCAGTCTGGGGCTGAGGT -continued

```
GAAGAAGCCTGGGTCCTCGGTGAAGGTCTCCTGCAAGGCTTCTGGAGGCA

CCTTCAGCAGCTATGCTATCACCTGGGTGCGACAGGCCCCTGGACAAGGG

CTTGAGTGGATGGGAGGGATCATCCCTATCTTTGGTACAGCAAACTTCGC

ACAGAAGTTCCAGGGCAGAGTCACGATTACCGCGGACGAATCCACGAGC

ACAGCCTACATGGAGCTGAGCAGCCTGAGATCTGAGGACACGGCCGTGTA

TTACTGTGCCCACCTAGGGGGGTTCGCTGACCCCTTTGACTACTGGGGCCA

GGGAACCCTGGTCACCGTCTCCTCAAGCACCAAGGGCCCATCGGTCTTCC

CCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTG

GGCACCCAGACCTACATCTGCAACGTGAATCACAAGCCCAGCAACACCAA

GGTGGACAAGAAAGTTGAGCCCAAATCTTGTGACAAAACTCACACATGCC

CACCGTGCCCAGCACCTGAACTCCTGGGGGGACCGTCAGTCTTCCTCTTCC

CCCCAAAACCCAAGGACACCCTCATGATCTCCCGGACCCCTGAGGTCACA

TGCGTGGTGGTGGACGTGAGCCACGAAGACCCTGAGGTCAAGTTCAACTG

GTACGTGGACGGCGTGGAGGTGCATAATGCCAAGACAAAGCCGCGGGAG

GAGCAGTACAACAGCACGTACCGTGTGGTCAGCGTCCTCACCGTCCTGCA

CCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCC

CCGAGAACCACAGGTGTACACCCTGCCCCCATCCCGGGAGGAGATGACCA

AGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGA

CCACGCCTCCCGTGCTGGACTCCGACGGCTCCTTCTTCCTCTACAGCAAGC

TCACCGTGGACAAGAGCAGGTGGCAGCAGGGGAACGTCTTCTCATGCTCC

GTGATGCATGAGGCTCTGCACAACCACTACACGCAGAAGAGCCTCTCCCT

GTCTCCGGGTAAAcgaaaaagaagatcaggttcgggtgcgccagtaaagcagacattaaactttgatttgctga

aacttgcaggtgatgtagagtcaaatccaggtccaatggcaacagggagccgaacctctctgctccttgctttcgggctcctt

tgcctaccgtggctccaagagggctcggcaGAAATTGTGTTGACACAGTCTCCAGCCACCC

TGTCTTTGTCTCCAGGGGAAAGAGCCACCCTCTCCTGCAGGGCCAGTCAG

AGTGTTAGCAACTACTTAGCCTGGTATCAACAGAAAGCTGGCCAGGCTCC

CAGGGTCCTCATCTATGATGCATTCAACAGGGCCACTGGCATCCCAGCCA

GGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTG

GCCTCCGCGGATCACCTTCGGCCAAGGGACACGACTGGAGATTAAAGGTC

AGCCCAAGGCTGCCCCCTCGGTCACTCTGTTCCCGCCCTCCTCTGAGGAGC

TTCAAGCCAACAAGGCCACACTGGTGTGTCTCATAAGTGACTTCTACCCG

GGAGCCGTGACAGTGGCCTGGAAGGCAGATAGCAGCCCCGTCAAGGCGG

GAGTGGAGACCACCACACCCTCCAAACAAAGCAACAACAAGTACGCGGC

CAGCAGCTATCTGAGCCTGACGCCTGAGCAGTGGAAGTCCCACAGAAGCT

ACAGCTGCCAGGTCACGCATGAAGGGAGCACCGTGGAGAAGACAGTGGC
```

-continued

```
CCCTACAGAATGTTCATAGCtctagaAtaatcaacctctggattacaaaatttgtgaaagattgactggtat
tcttaactatgagctccttttacgctatgtggatacgctgctttaatgccffTgtatcatgctattgcttcccgtatggctttcattttc
tcctccttgtataaatcctggttgctgtctctttatgaggagttgtggcccgttgtcaggcaacgtggcgtggtgtgcactgtgtt
tgctgacgcaacccccactggttggggcattgccaccacctgtcagctcctttccgggactttcgctttccccctccctattgc
cacggcggaactcatcgccgcctgccttgcccgctgctggacaggggctcggctgttgggcactgacaattccgtggtgtt
gtcggggaaatcatcgtcctttccttggctgctcgcctgtgttgccacctggattctgcgcgggacgtccttctgctacgtccc
ttcggccctcaatccagcggaccttccttcccgcggcctgctgccggctctgcggcctcttccgcgtcttcgccttcgccctc
agacgagtcggatctccctttgggccgcctccccgcctAAGCTTATCGATACCGTCGAGATCTAA
CTTGTTTATTGCAGCTTATAATGGTTACAAATAAAGCAATAGCATCACAAA
TTTCACAAATAAAGCATTTTTTTCACTGCATTCTAGTTGTGGTTTGTCCAAA
CTCATCAATGTATCTTATCATGTCTGGATCTCGACCTCGACTAGAGCATGG
CTACGTAGATAAGTAGCATGGCGGGTTAATCATTAACTACAAGGAACCCC
TAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCA
GTGAGCGAGCGAGCGCGCCAGCTGGCGTAATAGCGAAGAGGCCCGCACC
GATCGCCCTTCCCAACAGTTGCGCAGCCTGAATGGCGAATGGAATTCCAG
ACGATTGAGCGTCAAAATGTAGGTATTTCCATGAGCGTTTTTCCTGTTGCA
ATGGCTGGCGGTAATATTGTTCTGGATATTACCAGCAAGGCCGATAGTTTG
AGTTCTTCTACTCAGGCAAGTGATGTTATTACTAATCAAAGAAGTATTGCG
ACAACGGTTAATTTGCGTGATGGACAGACTCTTTTACTCGGTGGCCTCACT
GATTATAAAAACACTTCTCAGGATTCTGGCGTACCGTTCCTGTCTAAAATC
CCTTTAATCGGCCTCCTGTTTAGCTCCCGCTCTGATTCTAACGAGGAAAGC
ACGTTATACGTGCTCGTCAAAGCAACCATAGTACGCGCCCTGTAGCGGCG
CATTAAGCGCGGCGGGTGTGGTGGTTACGCGCAGCGTGACCGCTACACTT
GCCAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGGGT
TCCGATTTAGTGCTTTACGGCACCTCGACCCCAAAAAACTTGATTAGGGTG
ATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAA
CACTCAACCCTATCTCGGTCTATTCTTTTGATTTATAAGGGATTTTGCCGAT
TTCGGCCTATTGGTTAAAAAATGAGCTGATTTAACAAAAATTTAACGCGA
ATTTTAACAAAATATTAACGTTTACAATTTAAATATTTGCTTATACAATCT
TCCTGTTTTTGGGGCTTTTCTGATTATCAACCGGGGTACATATGATTGACA
TGCTAGTTTTACGATTACCGTTCATCGATTCTCTTGTTTGCTCCAGACTCTC
AGGCAATGACCTGATAGCCTTTGTAGAGACCTCTCAAAAATAGCTACCCT
CTCCGGCATGAATTTATCAGCTAGAACGGTTGAATATCATATTGATGGTGA
TTTGACTGTCTCCGGCCTTTCTCACCCGTTTGAATCTTTACCTACACATTAC
TCAGGCATTGCATTTAAAATATATGAGGGTTCTAAAAATTTTTATCCTTGC
GTTGAAATAAAGGCTTCTCCCGCAAAAGTATTACAGGGTCATAATGTTTTT
GGTACAACCGATTTAGCTTTATGCTCTGAGGCTTTATTGCTTAATTTTGCTA
```

-continued

```
ATTCTTTGCCTTGCCTGTATGATTTATTGGATGTTGGAATTCCTGATGCGGT

ATTTTCTCCTTACGCATCTGTGCGGTATTTCACACCGCATATGGTGCACTC

TCAGTACAATCTGCTCTGATGCCGCATAGTTAAGCCAGCCCCGACACCCG

CCAACACCCGCTGACGCGCCCTGACGGGCTTGTCTGCTCCCGGCATCCGCT

TACAGACAAGCTGTGACCGTCTCCGGGAGCTGCATGTGTCAGAGGTTTTC

ACCGTCATCACCGAAACGCGCGAGACGAAAGGGCCTCGTGATACGCCTAT

TTTTATAGGTTAATGTCATGATAATAATGGTTTCTTAGACGTCAGGTGGCA

CTTTTCGGGGAAATGTGCGCGGAACCCCTATTTGTTTATTTTTCTAAATAC

ATTCAAATATGTATCCGCTCATGAGACAATAACCCTGATAAATGCTTCAAT

AATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGC

TGGTGAAAGTAAAAGATGCTGAAGATCAGTTGGGTGCACGAGTGGGTTAC

ATCGAACTGGATCTCAACAGCGGTAAGATCCTTGAGAGTTTTCGCCCCGA

AGAACGTTTTCCAATGATGAGCACTTTTAAAGTTCTGCTATGTGGCGCGGT

ATTATCCCGTATTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGCTTTTTTGCACAACATGGGGGATCATGTAACTCGCCTTGATC

GTTGGGAACCGGAGCTGAATGAAGCCATACCAAACGACGAGCGTGACAC

CACGATGCCTGTAGCAATGGCAACAACGTTGCGCAAACTATTAACTGGCG

AACTACTTACTCTAGCTTCCCGGCAACAATTAATAGACTGGATGGAGGCG

GATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGC

AGCACTGGGGCCAGATGGTAAGCCCTCCCGTATCGTAGTTATCTACACGA

CGGGGAGTCAGGCAACTATGGATGAACGAAATAGACAGATCGCTGAGAT

AGGTGCCTCACTGATTAAGCATTGGTAACTGTCAGACCAAGTTTACTCATA

TATACTTTAGATTGATTTAAAACTTCATTTTTAATTTAAAAGGATCTAGGT

GAAGATCCTTTTTGATAATCTCATGACCAAAATCCCTTAACGTGAGTTTTC

GTTCCACTGAGCGTCAGACCCCGTAGAAAAGATCAAAGGATCTTCTTGAG

ATCCTTTTTTTCTGCGCGTAATCTGCTGCTTGCAAACAAAAAAACCACCGC

TACCAGCGGTGGTTTGTTTGCCGGATCAAGAGCTACCAACTCTTTTTCCGA

AGGTAACTGGCTTCAGCAGAGCGCAGATACCAAATACTGTCCTTCTAGTG

TAGCCGTAGTTAGGCCACCACTTCAAGAACTCTGTAGCACCGCCTACATA

CCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGC

GGTCGGGCTGAACGGGGGGTTCGTGCACACAGCCCAGCTTGGAGCGAAC

GACCTACACCGAACTGAGATACCTACAGCGTGAGCTATGAGAAAGCGCCA

CGCTTCCCGAAGGGAGAAAGGCGGACAGGTATCCGGTAAGCGGCAGGGT

CGGAACAGGAGAGCGCACGAGGGAGCTTCCAGGGGGAAACGCCTGGTAT

CTTTATAGTCCTGTCGGGTTTCGCCACCTCTGACTTGAGCGTCGATTTTTGT
```

-continued

GATGCTCGTCAGGGGGGCGGAGCCTATGGAAAAACGCCAGCAACGCGGC

CTTTTTACGGTTCCTGGCCTTTTGCTGGCCTTTTGCTCACATGTTCTTTCCT

GCGTTATCCCCTGATTCTGTGGATAACCGTATTACCGCCTTTGAGTGAGCT

GATACCGCTCGCCGCAGCCGAACGACCGAGCGCAGCGAGTCAGTGAGCG

AGGAAGCGGAAGAGCGCCCAATACGCAAACCGCCTCTCCCCGCGCGTTGG

CCGATTCATTAATG.

The AAV can be purified using any conventional methods known in the art. For example, the AAV can be purified from packaging cells and/or the supernatant of the packaging cells by separation method using a density gradient centrifugation (e.g. CsCl, iodixanol or sucrose gradient) and/or chromatography (e.g. heparin column, anion exchange or hydroxyapatite chromatography).

In certain embodiments, the packaging cell is mammalian cell. In certain embodiments, the packaging cell is HEK293 cell.

Pharmaceutical Composition and Method of Administration

The present disclosure further provides pharmaceutical compositions comprising recombinant expression vectors expressing the neutralizing antibodies against SARS-CoV-2 or antigen-binding fragments thereof provided herein and one or more pharmaceutically acceptable carriers.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The pharmaceutically acceptable carriers for use in the pharmaceutical compositions of the present disclosure may include, but are not limited to, for example, pharmaceutically acceptable liquids, gels, or solid carriers, aqueous vehicles (e.g., sodium chloride injection, Ringer's injection, isotonic glucose injection, sterile water injection, or Ringer's injection of glucose and lactate), non-aqueous vehicles (e.g., fixed oils of vegetable origin, cottonseed oil, corn oil, sesame oil, or peanut oil), antimicrobial agents, isotonic agents (such as sodium chloride or dextrose), buffers (such as phosphate or citrate buffers), antioxidants (such as sodium bisulfate), anesthetics (such as procaine hydrochloride), suspending/dispending agents (such as sodium carboxymethylcellulose, hydroxypropyl methylcellulose, or polyvinylpyrrolidone), chelating agents (such as EDTA (ethylenediamine tetraacetic acid) or EGTA (ethylene glycol tetraacetic acid)), emulsifying agents (such as Polysorbate 80 (Tween-80)), diluents, adjuvants, excipients, or non-toxic auxiliary substances, other components known in the art, or various combinations thereof. Suitable components may include, for example, fillers, binders, disintegrants, buffers, preservatives, lubricants, flavorings, thickeners, coloring agents, or emulsifiers.

In certain embodiments, the pharmaceutical composition is an oral formulation. The oral formulations include, but are not limited to, capsules, cachets, pills, tablets, troches (for taste substrates, usually sucrose and acacia or tragacanth), powders, granules, or aqueous or non-aqueous solutions or suspensions, or water-in-oil or oil-in-water emulsions, or elixirs or syrups, or confectionery lozenges (for inert bases, such as gelatin and glycerin, or sucrose or acacia) and/or mouthwash and its analogs.

In certain embodiments, the pharmaceutical composition may be an injectable formulation, including sterile aqueous solutions or dispersions, suspensions or emulsions. In all cases, the injectable formulation should be sterile and should be liquid to facilitate injections. It should be stable under the conditions of manufacture and storage, and should be resistant to the infection of microorganisms (such as bacteria and fungi). The carrier may be a solvent or dispersion medium containing, for example, water, ethanol, polyols (e.g., glycerol, propylene glycol, and liquid polyethylene glycols, etc.) and suitable mixtures and/or vegetable oils thereof. The injectable formulation should maintain proper fluidity, which may be maintained in a variety of ways, for example, using a coating such as lecithin, using a surfactant, etc. Antimicrobial contamination can be achieved by the addition of various antibacterial and antifungal agents (e.g., parabens, chlorobutanol, phenol, sorbic acid, thimerosal, etc.).

In certain embodiments, unit-dose parenteral preparations are packaged in an ampoule, a vial or a syringe with a needle. All preparations for parenteral administration should be sterile and not pyretic, as is known and practiced in the art.

Methods of Treatment

Administration of the recombinant expression vectors of the present disclosure to the cell can be by any means, including contacting the recombinant expression vector with the cell. For such in vitro method, the vector can be administered to the cell by standard transduction methods. (See e.g., Sambrook, Supra.) The cells being transduced can be derived from a human, and other mammals such as primates, horse, sheep, goat, pig, dog, rat, and mouse. Cell types and tissues that can be targeted include, but are not limited to, adipocytes, adenocyte, adrenal cortex, amnion, aorta, ascites, astrocytes, bladder, bone, bone marrow, brain, breast, bronchus, cells of the central nervous system (CNS), cardiac muscle, cecum, cervix, chorion, colon, conjunctiva, connective tissue, cornea, dermis, duodenum, endometrium, endothelium, epithelial tissue, epidermis, ependymal, esophagus, eye, fascia, fibroblasts, foreskin, gastric, glial cells, glioblast, gonad, hepatic cells, histocyte, ileum, intestine, small intestine, jejumim, keratinocytes, kidney, larynx, leukocytes, lipocyte, liver, lung, lymph node, lymphoblast, lymphocytes, macrophages, mammary alveolar nodule, mammary gland, mastocyte, maxilla, melanocytes, monocytes, mouth, microglia, myelin, nervous tissue, neural cells, neuroblast, neurons, neuroglia, oligodendrocytes, osteoblasts, osteogenic cells, ovary, palate, pancreas, papilloma, cells of the peripheral nervous system, peritoneum, pituicytes, pharynx, placenta, plasma cells, pleura, prostate, rectum, salivary gland, skeletal muscle, skin, smooth muscle, somatic, spleen, squamous, stomach, submandibular gland, submaxillary gland, synoviocytes, testis, thymus, thyroid, trabeculae, trachea, turbinate, umbilical cord, ureter, and uterus. In a preferred embodiment, the cells are muscle cells.

In one aspect, the present disclosure also provides methods of treating or preventing SARS-CoV-2 infection in a subject, comprising administering to the subject an effective amount of the recombinant expression vector provided herein, and/or the pharmaceutical composition provided herein.

In another aspect, the present disclosure also provides methods for neutralizing SARS-CoV-2 in a subject, comprising administering the recombinant expression vector provided herein or the pharmaceutical composition provided herein to the subject.

In another aspect, the present disclosure also provides methods for preventing, inhibiting progression of, and/or delaying the onset of SARS-CoV-2 infection or an SARS-CoV-2-associated condition in a subject, comprising administering to the subject an effective amount of the recombinant expression vector provided herein, and/or the pharmaceutical composition provided herein.

In another aspect, the present disclosure also provides methods for preventing or reducing transmission of SARS-CoV-2 by a SARS-CoV-2 infected subject, comprising administering to the subject an effective amount of the recombinant expression vector provided herein, and/or the pharmaceutical composition provided herein.

In some embodiments, the present disclosure also provides methods for reducing viral load in a SARS-CoV-2 infected subject, comprising administering to the subject an effective amount of the recombinant expression vector provided herein, and/or the pharmaceutical composition provided herein.

In certain embodiments, the subject is human.

In certain embodiments, the subject is a human with or at risk for SARS-CoV-2 infection. SARS-CoV-2 infection can include, for example, infection of SARS-CoV-2 at respiratory tract, including nasal cavity infection, lower respiratory tract infection, or lung infection.

In certain embodiments, the subject is human exposed to or suspected of having exposure to SARS-CoV-2. The term "SARS-CoV-2 exposure" means being exposed to an environment where a SARS-CoV-2 carrier is present or has appeared. A "SARS-CoV-2 carrier" refers to any living or non-living subject with transmissible SARS-CoV-2 on or in it. "Transmissible SARS-CoV-2" refers to SARS-CoV-2 capable of spreading from one living or non-living subject to another living or non-living subject.

The term "effective amount" as used herein refers to a dosage of a medicament which can significantly eliminating, ameliorating or improving the symptoms associated with a disease or abnormal condition or which can produce the desired effect of preventing onset of symptoms associated with a disease or abnormal condition or even preventing the development of a disease or abnormal condition. The disease or abnormal condition can be associated with viral infection, such as SARS-CoV-2 infection. The effective amount of the recombinant expression vector of the present disclosure means the dosage thereof that can result in eliminating, ameliorating or improving symptoms associated with onset of SARS-CoV-2 infection symptoms, including but is not limited to, fever or chills, cough, shortness of breath or difficulty breathing, fatigue, muscle or body aches, headache, new loss of taste or smell, sore throat, congestion or runny nose, nausea or vomiting, and diarrhea; the effective amount of the antibodies or antigen binding fragment thereof of the present disclosure also means the dosage thereof that can effectively prevent SARS-CoV-2 infection or effectively prevent onset of SARS-CoV-2 infection symptoms.

The effective amount of a recombinant expression vector provided herein will depend on various factors known in the art, such as body weight, age, past medical history, present medications, state of health of the subject and potential for cross-reaction, allergies, sensitivities and adverse side-effects, as well as the administration route and extent of disease development. Dosages may be proportionally reduced or increased by a person skilled in the art (e.g. physician or veterinarian) as indicated by these and other circumstances or requirements.

In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g. a therapeutic response). For example, a single dose may be administered, or several divided doses may be administered over time.

In certain embodiments, the recombinant expression vector and the pharmaceutical composition may be administered at a therapeutically effective dosage of about $10^4$ vector genomes (VG) to about $10^{14}$ VG (e.g., about $10^4$ VG, about $2*10^4$ VG, about $5*10^4$ VG, about $10^5$ VG, about $2*10^5$ VG, about $5*10^5$ VG, about $10^6$ VG, about $2*10^6$ VG, about $5*10^6$ VG, about $10^7$ VG, about $2*10^7$ VG, about $5*10^7$ VG, about $10^8$ VG, about $2*10^8$ VG, about $5*10^8$ VG, about $10^9$ VG, about $2*10^9$ VG, about $5*10^9$ VG, about $10^{10}$ VG, about $2*10^{10}$ VG, about $5*10^{10}$ VG, about $10^{11}$ VG, about $2*10^{11}$ VG, about $5*10^{11}$ VG, about $10^{12}$ VG, about $2*10^{12}$ VG, about $5*10^{12}$ VG, about $10^{13}$ VG, about $2*10^{13}$ VG, about $5*10^{13}$ VG, or about $10^{14}$ VG). In certain of these embodiments, the recombinant expression vector and the pharmaceutical composition is administered at a dosage of about $8*10^{11}$ VG or less. In certain of these embodiments, the dosage is $5*10^{11}$ VG or less, $4*10^{11}$ VG or less, $3*10^{11}$ VG or less, $2*10^{11}$ VG or less, $1*10^{11}$ VG or less, $5*10^{10}$ VG or less, $4*10^{10}$ VG or less, $3*10^{10}$ VG or less, $2*10^{10}$ VG or less, $10^{10}$ VG or less, $5*10^9$ VG or less, $4*10^9$ VG or less, $3*10^9$ VG or less, $2*10^9$ VG or less, $10^9$ VG or less. A particular dosage can be divided and administered multiple times separated by interval, e.g., once every day, twice or more every day, twice or more every month, once every week, once every two weeks, once every three weeks, once a month, once every two months, once every three months, once every four months, once every five months, once every six months or more. In certain embodiments, the administered dosage may vary over the course of treatment. For example, in certain embodiments, the initially administered dosage can be higher than subsequently administered dosages. In certain embodiments, the administered dosages are adjusted in the course of treatment depending on the response of the administration subject.

Dosage regimens may be adjusted to provide the optimum desired response (e.g., a therapeutic response). For example, a single dose may be administered, or several divided doses may be administered over time.

The recombinant expression vector provided herein may be administered by any route known in the art, such as for example parenteral (e.g. subcutaneous, intraperitoneal, intravenous, including intravenous infusion, intramuscular, intravaginal, epicutaneous, transdermal or intradermal injection) or non-parenteral (e.g. oral, intranasal, mucosal, intraocular, sublingual, rectal, or topical) routes. In certain embodiments, the rout of administration is intramuscular injection.

Combination

In some embodiments, the recombinant expression vector provided herein may be administered alone or in combination with a therapeutically effective amount of a second therapeutic agent. For example, the recombinant expression vector disclosed herein may be administered in combination with a second therapeutic agent, for example, an antiviral agent such as a second recombinant expression vector expressing a second SARS-CoV-2 neutralizing antibody, a second SARS-CoV-2 neutralizing antibody, RNA dependent RNA polymerase inhibitor, a nucleoside analog, antiviral cytokines (such as interferons), immunostimulatory agents, and other antiviral agents.

In certain of these embodiments, the recombinant expression vector provided herein that is administered in combination with one or more additional therapeutic agents may be administered simultaneously with the one or more additional therapeutic agents, and in certain of these embodiments the recombinant expression vector and the additional therapeutic agent(s) may be administered as part of the same pharmaceutical composition. However, the recombinant expression vector administered "in combination" with another therapeutic agent does not have to be administered simultaneously with or in the same composition as the agent. A recombinant expression vector thereof administered prior to or after another agent is considered to be administered "in combination" with that agent as the phrase is used herein, even if the recombinant expression vector and the second agent are administered via different routes. Where possible, additional therapeutic agents administered in combination with the recombinant expression vector thereof disclosed herein are administered according to the schedule listed in the product information sheet of the additional therapeutic agent, or according to the Physicians' Desk Reference 2003 (Physicians' Desk Reference, $57^{th}$ Ed; Medical Economics Company; ISBN: 1563634457; $57^{th}$ edition (November 2002)) or protocols well known in the art.

Kits

In certain embodiments, the present disclosure provides a kit comprising the recombinant expression vector provided herein and/or the pharmaceutical composition provided herein. In certain embodiments, the present disclosure provides a kit comprising the recombinant expression vector provided herein, and a second therapeutic agent. The second therapeutic agent can be an antiviral agent, such as a second SARS-CoV-2 neutralizing antibody, a second recombinant expression vector expressing a second SARS-CoV-2 neutralizing antibody, a RNA dependent RNA polymerase inhibitor, a nucleoside analog, antiviral cytokines (such as interferons), immunostimulatory agents, and other antiviral agents.

In certain embodiments, the second therapeutic agent is selected from the group consisting of Ivermectin, Colcrys (colchicine), Avigan (favipiravir) and other antiviral medications, Tamiflu (oseltamivir), Kaletra (lopinavir/ritonavir), Actemra (tocilizumab), Convalescent plasma, Azithromycin, Hydroxychloroquine and chloroquine, Dexamethasone, Remdesivir, Fluvoxamine, Bevacizumab, sarilumab, Tocilizumab, Corticosteroids, Nitazoxanide, Umifenovir, Famotidine, camostat, and Nafamostat.

Such kits can further include, if desired, one or more of various conventional pharmaceutical kit components, such as, for example, containers with one or more pharmaceutically acceptable carriers, additional containers etc., as will be readily apparent to a person skilled in the art. Instructions, either as inserts or a labels, indicating quantities of the components to be administered, guidelines for administration, and/or guidelines for mixing the components, can also be included in the kit.

In another aspect, the present disclosure provides kits comprising the recombinant expression vector thereof provided herein and/or the pharmaceutical composition provided herein, optionally with a detectable entity, which is useful in detecting SARS-CoV-2 virus. The kits may further comprise instructions for use.

Medical Usage

In another aspect, the present disclosure also provides use of the recombinant expression vector provided herein and/or the pharmaceutical composition provided herein in the manufacture of a medicament for treating or preventing SARS-CoV-2 infection in a subject; or for preventing, inhibiting progression of, and/or delaying the onset of SARS-CoV-2 infection or an SARS-CoV-2-associated condition in a subject; or for preventing or reducing transmission of SARS-CoV-2 by a SARS-CoV-2 infected subject; or for reducing viral load in a SARS-CoV-2 infected subject.

In another aspect, the present disclosure also provides use of the recombinant expression vector provided herein and/or the pharmaceutical composition provided herein in the manufacture of a diagnostic reagent for diagnosing SARS-CoV-2 infection.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. A person skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Anti-SARS-CoV-2 Neutralizing Antibody

Materials and Methods

Human Samples

Peripheral blood mononuclear cells (PBMCs) from healthy control donors were collected from the Centre Hospitalier Universitaire of Université Laval (CHU-Université Laval), while PBMCs from COVID-19 survivors were obtained from SunnyBrook Hospital in Toronto. Ethical approval from ethic boards from both institutions were obtained prior to the sample collection and all participants signed an individual inform consent.

Fluorescent Cell Sorting

SARS-CoV-2 virus-like particles (VLP) (Medicago, Quebec, Canada) were biotinylated using EZ-Link™ Sulfo-NHS-Biotin according to the manufacturer's instruction (ThermoFisher scientific, Burlington, Canada).

PBMCs from COVID-19 survivors were thawed and rested for 30 minutes prior to staining using 1 μg of biotinylated SARS-CoV-2 VLP. Samples were then stained using a viability dye (Fixable Viability Dye eFluor, ThermoFisher), A488 coupled streptavidin (Biolegend, San Jose, Calif.), and a combination of lineage markers against CD14 (M5E2), CD3 (SP34-2), CD19 (HIB19), IgG (G18-145) and IgM (G20-127), all from BD Biosciences (San Jose, Calif.). After extensive washing of the samples, SARS-CoV-2 specific B cells were individually sorted using a FACSARIA Fusion (BD Biosciences). Sorted B cells were cultured for 2 weeks using feeder cells as previously described (Cox et al. mAbs 8:1, 129-140; 2016). Both supernatant and cells from SARS-CoV-2 specific B cell culture was collected for further analysis.

SARS-CoV-2 Specific Enzyme-Linked Immunosorbent Assay (ELISA)

Wells of a 96 well plate were coated overnight with 100 ng of SARS-CoV-2 VLP (Medicago). After extensive washing and blocking with PBS, 5% milk, wells were incubated with culture supernatant for 1 hour at 37° C. Following additional washes, wells were incubated with 15 ng of horseradish peroxidase (HRP) conjugated goat anti-human IgG (Mandel scientific, Guelph, Canada). After a final set of washes, wells were incubated with 2,2'-Azinobis [3-ethylbenzothiazoline-6-sulfonic acid]-diammonium salt (ABTS) substrate (Mandel scientific) and the absorbance was read at 405 nm.

Recovery of Antibody Sequences

Antibody sequences were obtained as previously described (Cox et al. mAbs 8:1, 129-140; 2016). RNA was extracted from single cell-sorted B-cell cultures with Qiagen RNeasy Micro Kit (Qiagen) following manufacturer's instruction. The human antibody genes were amplified using Qiagen One-step RT-PCR kit (Qiagen, Cat. no: 210212). The RT-PCR primers were designed based on published sets (see Smith et al., Rapid generation of fully human monoclonal antibodies specific to a vaccinating antigen. Nat Proto 2009; 4:372-84). The RT-PCR products were used as templates in nested-PCR to amplify antibody variable regions with Invitrogen pfx50 DNA polymerase, the design for forward and reverse nested-PCR primers were based on sequences at the start of framework 1 region of human IgG heavy and light chain variable regions as described earlier (see Collarini et al., Potent high-affinity antibodies for treatment and prophylaxis of respiratory syncytial virus derived from B cells of infected patients. J Immunol 2009; 183:6338-45). The nested-PCR products were then used as templates in overlapping PCR to connect antibody light and heavy chain PCR products with a linker sequence and were cloned with infusion HD cloning kit (Clontech, Cat no: 639649) into a plasmid vector for sequencing.

SARS-CoV-2 Neutralization Assay

Test antibodies were recombinantly expressed in IgG1 form using HEK293 transient expression system (Sino Biological) for further assays. Vero-E6 cells were inoculated in 96-well cell culture plates (20,000 cells per well) with DMEM (Gibco) supplemented with 10% fetal bovine serum and grown overnight at 37° C. Antibodies with indicated concentration were mixed with 100 TCID50 SARS-CoV-2. The mixture was moved to the wells containing Vero-E6 cells and incubated at 37° C. for 1 hour. Following removing the supernatants, 200 μL cell culture medium were added and the plates were then incubated at 37° C. with 5% $CO_2$ for 3 days. Cells were stained with crystal violet and absorbance at 570 nm/630 nm were measured. Neutralization was defined as percentage reduction compared to positive controls. Neutralization titers of two replicates were calculated using a non-linear regression analysis in GraphPad Prism 7.

S Protein-Specific ELISA

Polystyrene microplates (Corning) were coated overnight with 0.1 or 1 μg/mL of SARS-CoV-2 S, S1 or RBD protein (Sino Biological). After washing with PBS containing 0.2% Tween 20, the plates were blocked using 2% BSA (Sigma Aldrich) in PBST for 1 hour at 37° C. Following washing with PBST, testing antibodies (1 ug/mL) were added to each well and incubated at 37° C. for 1 hour. After washing with PBST, HRP-conjugated goat anti-human IgG antibody was added at the dilution of 1:5000 and incubated at 37° C. for 1 hour. After washing, 3,3',5,5'-Tetramethylbenzidine (TMB) substrate solution was added to the microplate and incubated at room temperature for 6 min, followed by adding 2M $H_2SO_4$ to stop the reaction. The absorbance was detected at 450 nm.

Example 2: Characterization of the Antibodies

After screening all obtained antibodies by SARS-CoV-2 specific binding assay (data not shown), three best antibodies (i.e., 37G2, 31C2, and 15A7) were obtained. The SARS-CoV-2 specific binding activities of the three antibodies are shown in FIG. 1. The CDR regions of the antibodies were sequenced and listed in Table 1.

Figure 2:
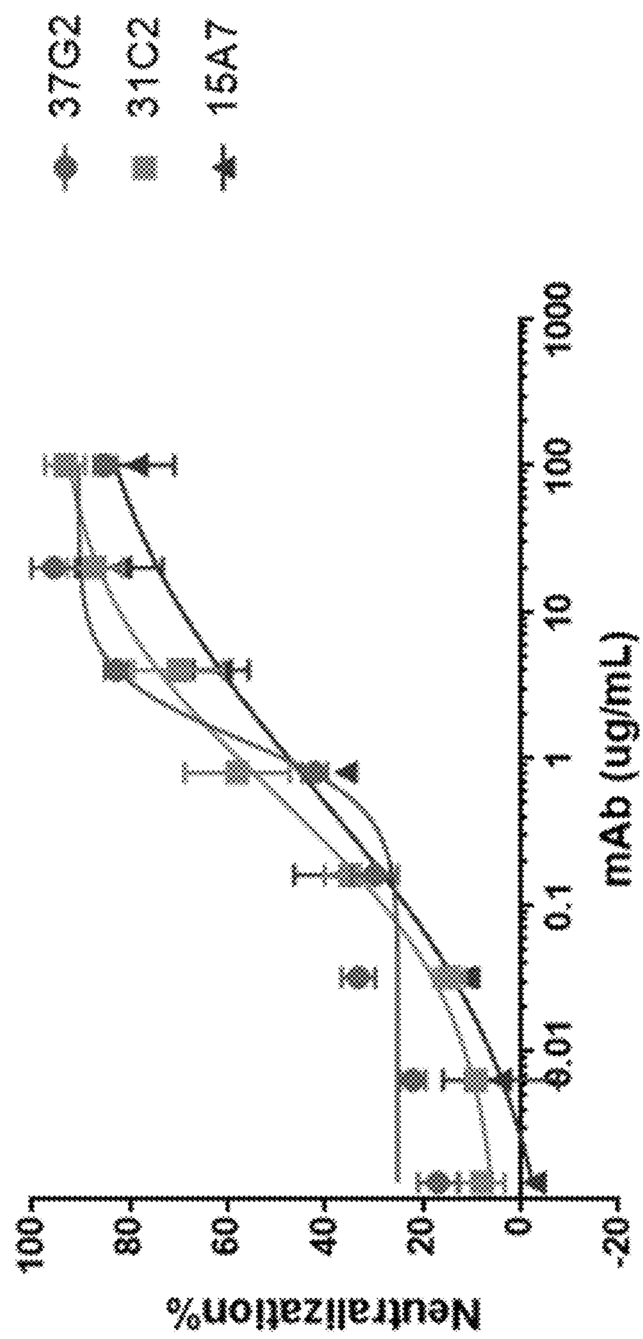
FIG. 2 shows neutralization of the antibodies provided in the disclosure to authentic SARS-CoV-2 in Vero-E6 cells.

These 3 antibodies were recombinantly expressed and subjected to an in vitro neutralizing assay using live virus in Vero-E6 cells. As shown in FIG. 2, all antibodies exhibit obvious neutralizing capacity against SARS-CoV-2 infection. The calculated $EC_{50}$ for 37G2, 31C2, and 15A7 are 1.37, 0.57, and 0.61 μg/mL, respectively.

Figure 3:
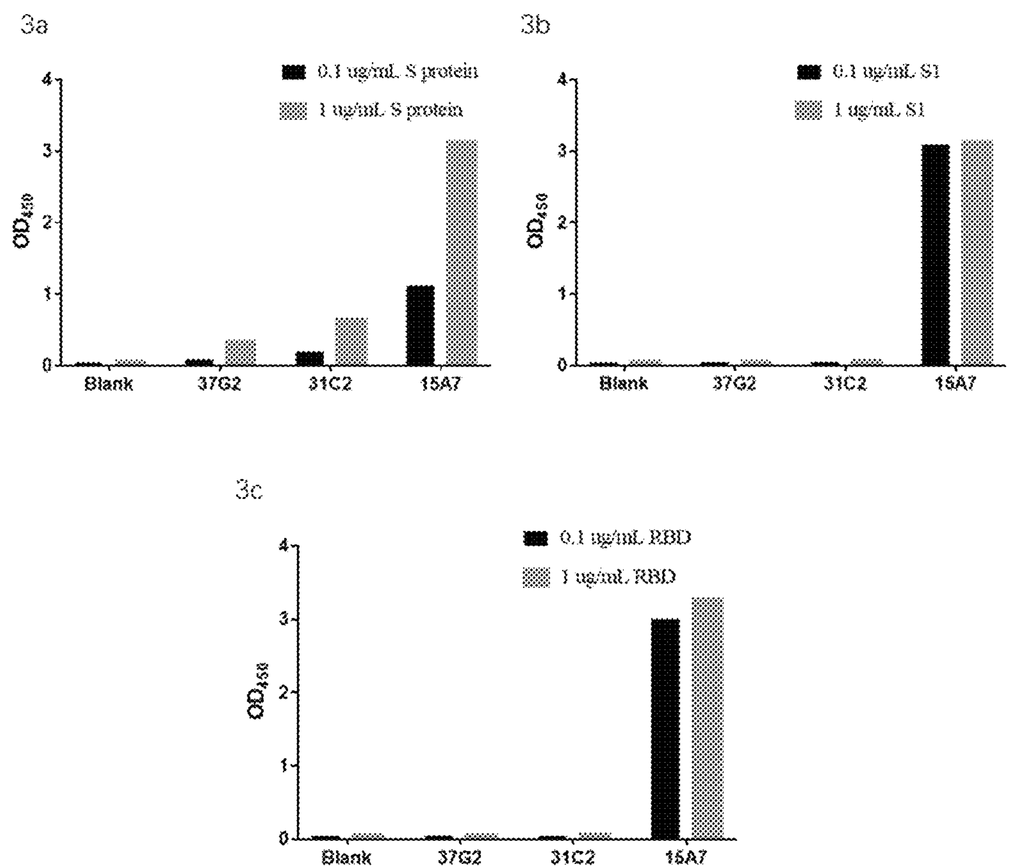
FIG. 3 shows binding profile of the antibodies provided in the disclosure with S protein (3a), S1 subunit (3b), and RBD (3c), as determined by ELISA.

We tested the binding properties of the antibodies with spike protein (S protein), S1 subunit, and RBD domain. As shown in FIG. 3, 15A7 binds to S protein, S1 subunit and RBD domain, suggesting that the antibody 15A7 blocks the interaction between SARS-CoV-2 and ACE2. The other two antibodies, 37G2 and 31C2, bind to S protein, but not to S1 subunit or RBD domain, suggesting that their binding site might be on S2 subunit of S protein.

Example 3: AAV-Mediated Antibody Gene Delivery

The experiment is designed to test the effect of AAV-mediated antibody gene transfer to protect against SARS-CoV-2 virus challenge in mice.

AAV-mAb Vector Construction

Antibody expression cassette preparation: Monoclonal antibody expression cassettes were synthesized by Genscript and contain a signal peptide, the variable heavy domain, the human IgG1 constant domain followed by a self-cleaving 2A peptide sequence, a signal peptide, the variable light domain and the human lambda constant domain. The antibody heavy chain and light chain nucleic acid sequences were codon optimized by Genscript. Each antibody expression cassette was amplified by PCR using Taq polymerase and the PCR products were gel purified and the bands on interest were also excised and purified using a gel extraction kit.

AAV vector preparation: The pAVA-00200 plasmid backbone contains the CASI promoter (Alejandro B. Balazs et al. Antibody-based Protection Against HIV Infection by Vectored ImmunoProphylaxis. Nature. 2012 Jan. 5; 481(7379): 81-84.), multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit.

AAV-mAb vector preparation: These PCR products contain the antibody expression cassettes in addition to 15 base pair 5' and 3' overhangs that align with the ends of the linearized pAVA-00200 backbone. Using in-fusion cloning (Andrea L. Throop et al. Recombinational Cloning Using Gateway and In-Fusion Cloning Schemes. Curr Protoc Mol Biol. 2015; 110: 3.20.1-3.20.23.), the amplified antibody expression cassettes are integrated with the pAVA-00200 backbone via homologous recombination. The resulting plasmids contain the following 5' ITR, CASI promoter, monoclonal antibody expression cassette, WPRE, SV40 polyA and ITR 3'.

Propagation, packaging and purification of recombinant mAb expression AAV vectors: AAV-mAb vector genomes encoding the variable heavy and light chains of 15A7 and FVM04 were prepared as described above. AAV genome and packaging plasmids were propagated in the SURE® 2 (Agilent) strain of *Escherichia coli*. AAV vectors were produced by co-transfection of HEK293 cells with genome and packaging plasmids. Vectors pseudotyped with AAV6.2FF were purified by heparin column (see published US application US 20190216949). AAV vector titers were determined by quantitative PCR.

Figure 4:
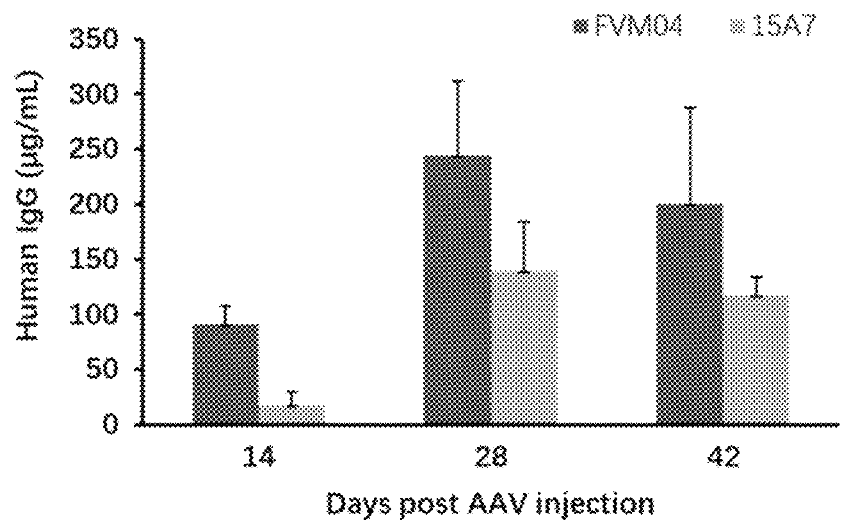
FIG. 4 shows AAV6.2FF-mediated sustained expression of antibody 15A7 or FVM04 in BALB/c mice after a single IM injection.

Protective Effect of AAV6.2FF-15A7 Against Authentic SARS-CoV-2 in Human hACE2-Transduced Mice 6-8 week-old BALB/c mice were intranasally administered $1\times10^{11}$ vector genomes (VG) of AAV6.2FF-human ACE2 (that express human ACE2) to render the animals susceptible to SARS-CoV-2 infection. Simultaneously, the animals were injected intramuscularly with $8\times10^{11}$ VG of AAV6.2FF-15A7 (SEQ ID NO: 61) or AAV6.2FF-FVM04 vector (prepared according the method described above). Notably, antibody 15A7 binds SARS-CoV-2 spike protein while FVM04 is an Ebola virus antibody and serves as a negative control. Blood samples were collected by saphenous bleed on day 0, 14, 28 and 42 of administration of the antibody AAV vector and analyzed for human IgG expression using a commercially available kit (Abcam 195215) (see FIG. 4). The sera at day 42 from all the mice in each group were pooled for testing the binding with SARS-CoV-2 Spike protein (Spike S1+S2 ECD-His Recombinant Protein from SinoBiological) and for determining the neutralization potency using a SARS-CoV-2 Surrogate Virus Neutralization Test (sVNT) Kit (RUO) from Genscript. SARS-CoV-2 specific Enzyme-linked immunosorbent assay (ELISA) (see Table 4 and Table 5).

TABLE 4

Binding affinity of pooled sera with SARS-Cov-2 S protein

| | OD450 nm | |
|---|---|---|
| Dilution | FVM04 (mock) | 15A7 |
| 50 | 0.0119 | 1.4454 |
| 100 | 0.0034 | 1.4812 |
| 200 | 0.0055 | 1.4175 |
| 400 | 0 | 1.1853 |
| 800 | 0 | 1.1122 |
| 1600 | 0 | 0.7729 |
| 3200 | 0 | 0.4998 |

TABLE 5

Neutralization potency of pooled sera

| | % inhibition | |
|---|---|---|
| Dilution | FVM04 (mock) | 15A7 |
| 10 | 13 | 62 |
| 20 | 7 | 43 |
| 40 | 8 | 26 |
| 80 | 1 | 14 |
| 160 | 0 | 3 |

Eight weeks following the vector administration, the mice were shipped to the Public Health Agency of Canada and challenged with $10^5$ $TCID_{50}$ of SARS-CoV-2 (SARS-CoV-2; hCoV-19/Canada/ON-VIDO-01/2020, GISAID accession #EPI_ISL_425177) in a volume of 50 μL by an intranasal route. Mice were weighted and monitored daily for clinical signs of infection throughout the course of the experiment. Cohorts of mice were sacrificed at day 4 post challenge and the lungs were collected for quantification of SARS-CoV-2 by $TCID_{50}$.

Figure 5:
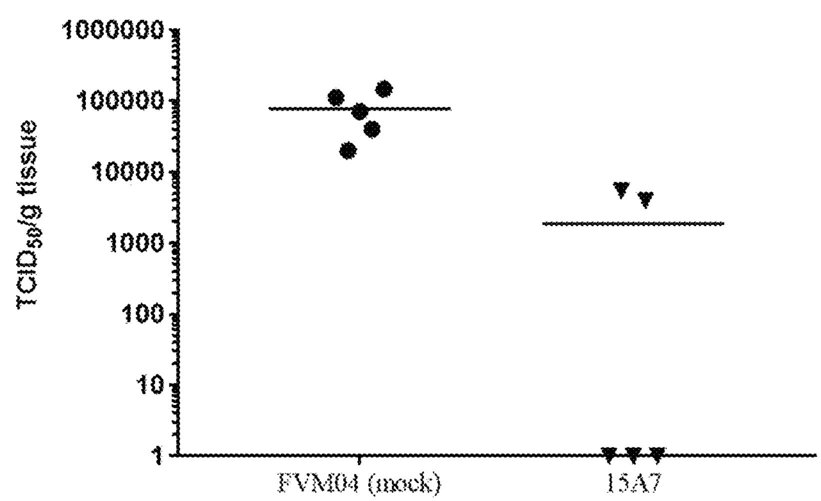
FIG. 5 shows AAV6.2FF-mediated antibody 15A7 expression protects human ACE2 transduced BALB/c mice against SARS-Cov-2 challenge. The mice received an IM injection of $8\times10^{11}$ VG of AAV6.2FF-15A7 or AAV6.2FF-FVM04 vector 8 weeks prior to intranasal challenge with $10^5$ $TCID_{50}$ of SARS-CoV-2. The mice were sacrificed 4 days post infection and the lungs were collected for quantification of SARS-CoV-2 by $TCID_{50}$.

For $TCID_{50}$ assays, the lung tissue samples were thawed, weighed, then immersed in 1 ml of MEM supplemented with 1% heat-inactivated FBS, 1× L-glutamine, and 2× penicillin-streptomycin. Samples were then homogenized with a stainless steel bead in a Bead Ruptor Elite Bead Mill Homogenizer (Omni International) at 4 m/s for 30 seconds then clarified by centrifugation at 1500×g for 6 minutes. Tissue homogenates were serially diluted 10-fold in the same medium. One hundred microliter volumes of the diluted samples were added to 96-well plates of 95% confluent Vero cells in replicates of three and incubated for 5 days at 37° C. with 5% $CO_2$. Five days following infection the wells were scored for the presence of cytopathic effect (see FIG. 5).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A recombinant expression vector comprising an expression cassette comprising a nucleic acid sequence encoding an anti-SARS-COV-2 neutralizing antibody or antigen-binding fragments thereof, wherein the anti-SARS-COV-2 neutralizing antibody or the antigen-binding fragments thereof comprises heavy chain CDR (HCDR)1, HCDR2 and HCDR3, and light chain CDR (LCDR)1, LCDR2 and LCDR3 wherein:
HCDR1 is the amino acid sequence of SEQ ID No: 1,
HCDR2 is the amino acid sequence of SEQ ID No: 2,
HCDR3 is the amino acid sequence of SEQ ID No: 3,
LCDR1 is the amino acid sequence of SEQ ID No: 4,
LCDR2 is the amino acid sequence of SEQ ID No: 5,
LCDR3 is the amino acid sequence of SEQ ID No: 6, and
wherein the anti-SARS-COV-2 neutralizing antibody or the antigen-binding fragments thereof further comprises a heavy chain variable region (VH) comprising the amino acid sequence of SEQ ID NO: 7 and a light chain variable region (VL) comprising the amino acid sequence of SEQ ID NO: 8.

2. The recombinant expression vector of claim 1, wherein the VH comprising the amino acid sequence of SEQ ID NO: 7 is encoded by nucleic acid sequence of SEQ ID NO: 9.

3. The recombinant expression vector of claim 1, wherein the VL comprising the amino acid sequence of SEQ ID NO: 8 is encoded by nucleic acid sequence of SEQ ID NO: 10.

4. The recombinant expression vector of claim 1, wherein the anti-SARS-COV-2 neutralizing antibody further comprises a heavy chain constant region and/or a light chain constant region.

5. The recombinant expression vector of claim 4, wherein the heavy chain constant region is from human IgG1.

6. The recombinant expression vector of claim 4, wherein the light chain constant region is from human lambda light chain.

7. The recombinant expression vector of claim 1, wherein a first signal peptide is operably linked to the anti-SARS-COV-2 neutralizing antibody VH at the N-terminal of the VH, and a second signal peptide is operably linked to the anti-SARS-COV-2 neutralizing antibody VL at the N-terminal of the VL.

8. The recombinant expression vector of claim 1, wherein the recombinant expression vector is an adeno-associated virus (AAV) vector.

9. The recombinant expression vector of claim 8, wherein the expression cassette comprises in an orientation from 5' to 3' of the sense strand: a 5' AAV inverted terminal repeat (ITR)1-a promoter-the nucleic acid sequence encoding the anti-SARS-COV-2 neutralizing antibody-WPRE-a polyA signal sequence-a 3' AAV ITR2.

10. The recombinant expression vector of claim 9, wherein the nucleic acid sequence encoding the anti-SARS-COV-2 neutralizing antibody comprises encoding sequences of: the first signal peptide-the anti-SARS-COV-2 neutralizing antibody heavy chain variable region-a human IgG1 constant region-2A self-cleaving peptide-the second signal peptide-the anti-SARS-COV-2 neutralizing antibody light chain variable region-a human lambda light chain constant region, in an orientation from 5' to 3' of the sense strand.

11. The recombinant expression vector of claim 9, wherein the promoter is CASI promoter and the polyA signal sequence is SV40 polyA.

12. The recombinant expression vector of claim 9, wherein the AAV ITR1 and AAV ITR2 are AAV2 ITRs.

13. The recombinant expression vector of claim 8, wherein the AAV vector is pseudotyped with a mutated AAV6 capsid.

14. The recombinant expression vector of claim 1, comprises a nucleic acid sequence of SEQ ID NO: 61.

15. A genetically modified host cell comprising the recombinant expression vector of claim 1.

16. A pharmaceutical composition comprising the recombinant expression vector of claim 1 and a pharmaceutically acceptable carrier.

17. A method of treating or preventing SARS-CoV-2 infection in a subject, comprising administering to the subject an effective amount of the recombinant expression vector of claim 1.

18. The method of claim 17, wherein the subject has been identified as having SARS-CoV-2 infection, or is suspected of having SARS-CoV-2 infection, or is at risk of exposure to SARS-CoV-2.

* * * * *